(12) United States Patent
Reuber et al.

(10) Patent No.: US 9,676,831 B2
(45) Date of Patent: Jun. 13, 2017

(54) G748 TRANSCRIPTION FACTER FOR IMPROVING PLANT GROWTH

(75) Inventors: T. Lynne Reuber, San Mateo, CA (US); Oliver J. Ratcliffe, Oakland, CA (US); Frederick D. Hempel, Sunol, CA (US); Luc J. Adam, Hayward, CA (US); Cai-Zhong Jiang, Davis, CA (US); Robert A. Creelman, Castro Valley, CA (US); Jose Luis Riechmann, Barcelona (ES); Jacqueline E. Heard, Wenham, MA (US); Raymond R. Samaha, Soquel, CA (US); Pierre E. Broun, Notre-Dame D'Oe (FR); Magnus Hertzberg, Umeå (SE); Torgny Näsholm, Holmsund (SE)

(73) Assignees: SweTree Technologies AB, Umeå (SE); Mendel Biotechnology, Inc., Hayward, CA (US)

(*) Notice: Subject to any disclaimer, the term of this patent is extended or adjusted under 35 U.S.C. 154(b) by 609 days.

(21) Appl. No.: 13/582,046

(22) PCT Filed: Mar. 3, 2011

(86) PCT No.: PCT/US2011/027091
§ 371 (c)(1),
(2), (4) Date: Nov. 14, 2012

(87) PCT Pub. No.: WO2011/109661
PCT Pub. Date: Sep. 9, 2011

(65) Prior Publication Data
US 2013/0061345 A1  Mar. 7, 2013

Related U.S. Application Data

(60) Continuation-in-part of application No. 13/244,288, filed on Sep. 24, 2011, now abandoned, which is a continuation-in-part of application No. 12/077,535, filed on Mar. 17, 2008, now Pat. No. 8,030,546, application No. 13/582,046, which is a continuation-in-part of application No. 13/367,257, filed on Feb. 6, 2012, now Pat. No. 8,796,510, which is a division of application No. 12/338,024, filed on Dec. 18, 2008, now Pat. No. 8,110,725, which is a division of application No. 10/374,780, filed on Feb. 25, 2003, now Pat. No. 7,511,190, application No. 13/582,046, which is a continuation-in-part of application No. 12/702,109, filed on Feb. 8, 2010, now Pat. No. 8,426,678, which is a continuation-in-part of application No. 10/546,266, filed as application No. PCT/US2004/005654 on Feb. 25, 2004, now Pat. No. 7,659,446, application No. 13/582,046, which is a continuation-in-part of application No. 12/638,750, filed on Dec. 15, 2009, now Pat. No. 8,426,685, which is a continuation-in-part of application No. 11/728,567, filed on Mar. 26, 2007, now Pat. No. 7,635,800, which is a division of application No. 10/225,066, filed on Aug. 9, 2002, now Pat. No. 7,238,860, application No. 13/582,046, which is a continuation-in-part of application No. 12/577,662, filed on Oct. 12, 2009, now abandoned, which is a continuation-in-part of application No. 11/725,235, filed on Mar. 16, 2007, now Pat. No. 7,601,893, which is a division of application No. 10/225,068, filed on Aug. 9, 2002, now Pat. No. 7,193,129.

(60) Provisional application No. 61/310,372, filed on Mar. 4, 2010, provisional application No. 60/961,403, filed on Jul. 20, 2007, provisional application No. 60/336,049, filed on Nov. 19, 2001.

(51) Int. Cl.
C12N 15/82 (2006.01)
A01H 5/00 (2006.01)
C07K 14/415 (2006.01)

(52) U.S. Cl.
CPC ........ C07K 14/415 (2013.01); C12N 15/8261 (2013.01)

(58) Field of Classification Search
None
See application file for complete search history.

(56) References Cited

U.S. PATENT DOCUMENTS

2003/0121070 A1* 6/2003 Adam et al. .................. 800/278
2003/0217383 A1* 11/2003 Reuber et al. ................ 800/279
(Continued)

FOREIGN PATENT DOCUMENTS

WO  PCT/US2011/027091      7/2011

OTHER PUBLICATIONS

Broun, 2004, Curr. Opin. Plant Biol. 7: 202-209.*
(Continued)

*Primary Examiner* — Amjad Abraham
*Assistant Examiner* — Bratislav Stankovic
(74) *Attorney, Agent, or Firm* — Cooley LLP

(57) ABSTRACT

Transcription factor polynucleotides and polypeptides incorporated into nucleic acid constructs, including expression vectors, have been introduced into plants and were ectopically expressed. Transgenic plants transformed with many of these constructs have been shown to have increased tolerance to an abiotic stress (in some cases, to more than one abiotic stress), increased growth, and/or increased biomass. The abiotic stress may include, for example, salt, hyperosmotic stress, water deficit, heat, cold, drought, and/or low nutrient conditions.

7 Claims, 3 Drawing Sheets

(56) References Cited

U.S. PATENT DOCUMENTS

Figure 1:
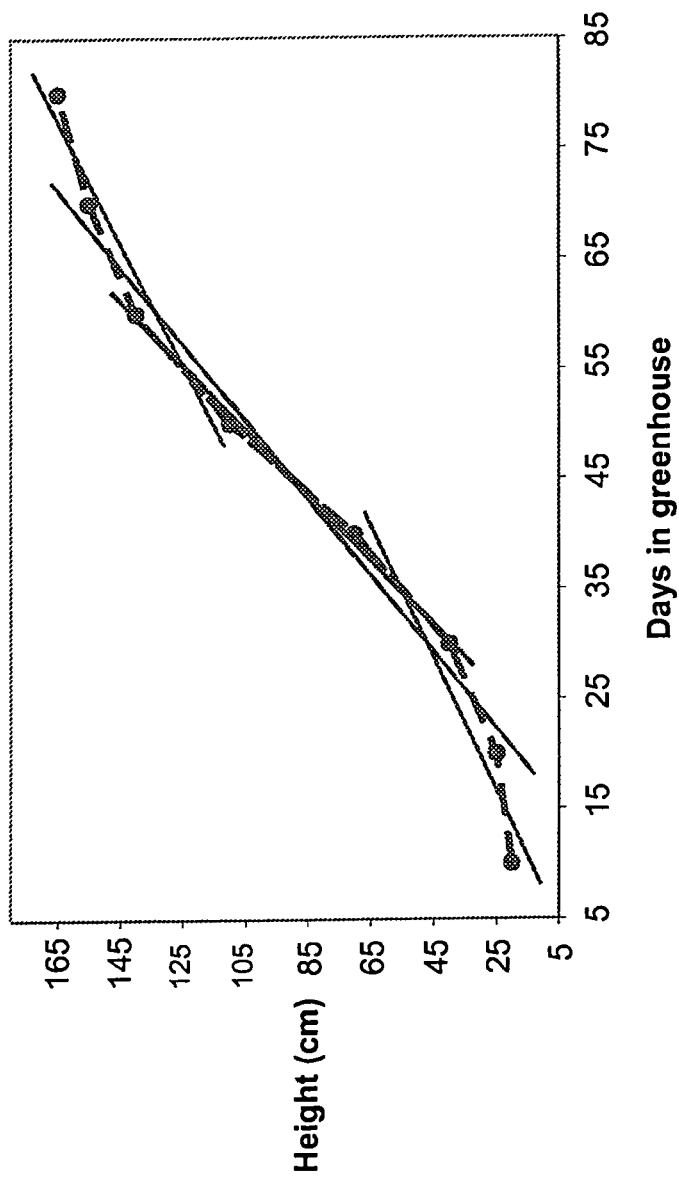

2006/0195944 A1* 8/2006 Heard .................. C07K 14/415
800/287
2007/0022495 A1* 1/2007 Reuber et al. ................ 800/279

OTHER PUBLICATIONS

Maniatis et al., Molecular Cloning: A Laboratory Manual, Cold Spring Harbor Laboratory, 1982; see in particular, pp. 387-389.*
Guo et al., 2004, Proceedings of the National Academy of Sciences USA 101: 9205-9210.*
Yang et al., 2006, Plant Physiology 142: 820-830.*
Cseke et al., 2007, Plant Cell Reports 26: 1529-1538.*
Egea-Cortines and Weiss, 2001, Nature Biotechnology 19: 215-216.*
NCBI Accession No. AK318629 (GI:227202541) (Apr. 21, 2009); Iida, K., et al.; Arabidopsis thaliana AT5G05550 mRNA, complete cds, clone: RAFL09-36-C21.
NCBI Accession No. AB005241 (GI:2264313) (Jul. 17, 1997); Nakamura, Y.; Arabidopsis thaliana genomic DNA, chromosome 5, P1 clone:MOP10.
NCBI Accession No. NM_111947 (GI:18399117) (Jan. 30, 2002); Town, C.D., et al.; expressed protein.
NCBI Accession No. AK118084 (GI:26451220) (Dec. 6, 2002); Seki, M., et al.; Arabidopsis thaliana At3g58630 mRNA for unknown protein, complete cds, clone: RAFL19-33-K15.
NCBI Accession No. ACF87523 (GI:194706878) (Jul. 30, 2008); Yu,Y., et al.; unknown [Zea mays].
NCBI Accession No. ACG44857 (GI:195650779) (Oct. 29, 2008); Alexandrov, N.N., et al.; unknown [Zea mays].
NCBI Accession No. ACN35531 (GI:224032911) (Feb. 25, 2009); Yu, Y., et al.; unknown [Zea mays].
NCBI Accession No. NP_001142041 (GI:226502891) (Apr. 10, 2009); hypothetical protein LOC100274197 [Zea mays].
NCBI Accession No. NP_001151900 (GI:226498750) (Apr. 10, 2009); Alexandrov, N. N., et al.; 6b-interacting protein 1 [Zea mays].
NCBI Accession No. JB225331 (GI:484319105) (Apr. 28, 2013); Reuber, T.L., et al.; Sequence 313 from Patent EP2542563.
NCBI Accession No. JB225333 (GI:484319106) (Apr. 28, 2013); Reuber, T. L., et al.; Sequence 315 from Patent EP2542563.
NCBI Accession No. JB225335 (GI:484319107) (Apr. 28, 2013); Reuber, T. L., et al.; Sequence 317 from Patent EP2542563.
NCBI Accession No. CAN72489 (GI:147838982) (May 18, 2007); Velasco, R., et al.; hypothetical protein [Vitis vinifera].
NCBI Accession No. CAO41403 (GI:157351216) (Aug. 29, 2007); Jaillon, O., et al.; unnamed protein product [Vitis vinifera].
NCBI Accession No. XP_002270392 (GI:225439493) (Mar. 20, 2009); Predicted: hypothetical protein [Vitis vinifera].
NCBI Accession No. XP_002272959 (GI:225448501) (Mar. 20, 2009); Predicted: hypothetical protein [Vitis vinifera].
NCBI Accession No. XP_002280689 (GI:225446617) (Mar. 20, 2009); Predicted: hypothetical protein [Vitis vinifera].
Coruzzi, G. and Bush, D.R. (2001) "Nitrogen and Carbon Nutrient and Metabolite Signaling in Plants"; Plant Physiology, 125: 61-64.
Stitt, M. (1999) "Nitrate Regulation of Metabolism and Growth"; Current Opinion in Plant Biology, 2: 178-186.
Shuichi Yangagisawa, "Dof Domain Proteins: Plant-Specific Transcription Factors Associated with Diverse Phenomena Unique to Plants", Plant Cell Physiol., 2004, pp. 386-391, vol. 45, No. 4.
N. Gonzalez, "Structure and function of wood in mangroves", The University of Queensland, 2012, pp. 1-139.
Broun, Pierre. "Transcription factors as tools for metabolic engineering in plants." Current opinion in plant biology 7(2): 202-209 (Apr. 2004).

* cited by examiner

G748 TRANSCRIPTION FACTER FOR IMPROVING PLANT GROWTH

CROSS-REFERENCE TO RELATED APPLICATIONS

This application is a U.S. National Phase of PCT Application No. PCT/US2011/027091, filed Mar. 3, 2011 (expired), which claims the benefit of U.S. provisional application No. 61/310,372, filed Mar. 4, 2010. This application is also a continuation-in-part of U.S. patent application Ser. No. 13/244,288, filed Sep. 24, 2011 (pending), which is a continuation-in-part of U.S. patent application Ser. No. 12/077,535, filed Mar. 17, 2008 (issued as U.S. Pat. No. 8,030,546), which claims priority from provisional U.S. patent application No. 60/961,403 filed Jul. 20, 2007. This application is also a continuation-in-part of U.S. patent application Ser. No. 13/367,257, filed Feb. 6, 2012 (pending), which is a division of U.S. patent application Ser. No. 12/338,024, filed Dec. 18, 2008 (issued as U.S. Pat. No. 8,110,725), which is a division of U.S. patent application Ser. No. 10/374,780, filed Feb. 25, 2003 (issued as U.S. Pat. No. 7,511,190). This application is also a continuation-in-part of U.S. patent application Ser. No. 12/702,109, filed Feb. 8, 2010 (pending), which is a continuation-in-part of U.S. patent application Ser. No. 10/546,266, filed Aug. 19, 2005 (issued as U.S. Pat. No. 7,659,446), which is a National Stage entry of PCT patent application no. PCT/US04/05654, filed Feb. 25, 2004 (expired). This application is also a continuation-in-part of U.S. patent application Ser. No. 12/638,750, filed Dec. 15, 2009 (pending), which is a continuation-in-part of U.S. patent application Ser. No. 11/728,567, filed Mar. 26, 2007 (issued as U.S. Pat. No. 7,635,800), which is a division of U.S. patent application Ser. No. 10/225,066, filed Aug. 9, 2002 (issued as U.S. Pat. No. 7,238,860), which claims priority from provisional U.S. patent application No. 60/336,049, filed Nov. 19, 2001. This application is also a continuation-in-part of U.S. patent application Ser. No. 12/577,662, filed Oct. 12, 2009 (pending), which is a continuation-in-part of U.S. patent application Ser. No. 11/725,235, filed Mar. 16, 2007 (issued as U.S. Pat. No. 7,601,893), which is a division of U.S. patent application Ser. No. 10/225,068, filed Aug. 9, 2002 (issued as U.S. Pat. No. 7,193,129), which claims priority from provisional U.S. patent application No. 60/336,049, filed Nov. 19, 2001. The entire contents of each of these applications are hereby incorporated by reference.

FIELD OF THE INVENTION

The present invention relates to plant genomics and plant improvement.

BACKGROUND OF THE INVENTION

The Effects of Various Factors on Plant Yield

Yield of commercially valuable species in the natural environment is sometimes suboptimal since plants often grow under unfavorable conditions. These conditions may include an inappropriate temperature range, or a limited supply of soil nutrients, light, or water availability. More specifically, various factors that may affect yield, crop quality, appearance, or overall plant health include the following.

Nutrient Limitation and Carbon/Nitrogen Balance (C/N) Sensing

Nitrogen (N) and phosphorus (P) are critical limiting nutrients for plants. Phosphorus is second only to nitrogen in its importance as a macronutrient for plant growth and to its impact on crop yield.

Nitrogen and carbon metabolism are tightly linked in almost every biochemical pathway in the plant. Carbon metabolites regulate genes involved in N acquisition and metabolism, and are known to affect germination and the expression of photosynthetic genes (Coruzzi et al., 2001) and hence growth. Gene regulation by C/N (carbon-nitrogen balance) status has been demonstrated for a number of N-metabolic genes (Stitt, 1999; Coruzzi et al., 2001). A plant with altered carbon/nitrogen balance (C/N) sensing may exhibit improved germination and/or growth under nitrogen-limiting conditions.

Hyperosmotic Stresses, and Cold, and Heat

In water-limited environments, crop yield is a function of water use, water use efficiency (WUE; defined as aerial biomass yield/water use) and the harvest index [HI; the ratio of yield biomass (which in the case of a grain-crop means grain yield) to the total cumulative biomass at harvest]. WUE is a complex trait that involves water and $CO_2$ uptake, transport and exchange at the leaf surface (transpiration). Improved WUE has been proposed as a criterion for yield improvement under water limiting conditions and drought. Water deficit can also have adverse effects in the form of increased susceptibility to disease and pests, reduced plant growth and reproductive failure. Genes that improve WUE and tolerance to water deficit thus promote plant growth, fertility, and disease resistance.

Yield may also be limited by a plant's intrinsic growth rate. A faster growth rate at the seedling stage could allow a crop to become established faster. This would minimize exposure to stress conditions at early stages of growth when the plants are most sensitive. Additionally, it could allow a crop to grow faster than competing weed species. Accelerating plant growth overall would also improve yield per acre or reduce time to harvest. For example, this would be particularly desirable in forestry: an important aim in tree-breeding programs around the world is to produce plants with increased growth rates and stem volumes, and shorter rotation times.

Perennial Plants and Annual Crops

Perennial plants such as long-lived trees have a life style considerably different from annual plants such as *Arabidopsis* in that perennial plants such as trees have an indeterminate growth pattern, whereas plants like *Arabidopsis* eventually stop growth after the plant flowers and sets seed. The final size of an *Arabidopsis* plant is in many ways dependent on the developmental program from germination to flowering and seed set. Therefore, any change in the timing of these events can drastically change the size of the plant.

Perennial plants also may cycle between periods of active growth and dormancy. During active growth leaves perform photosynthesis to capture energy which then used to drive various cellular processes. The fixed carbon which converted to sucrose is transferred to storage tissues where it is stored during the dormant state. As growth reinitiates after release from dormancy, the fixed carbon is translocated to actively growing tissues. Similarly for nitrogen, amino acids are translocated also to storage tissues and stored as storage proteins during dormancy, and broken down as growth starts. Thus the life cycle of long lived trees differs significantly from annual crops. Due to these differences between annual crops and perennial plants such as trees, determinants of yield and the ability to measure them are likely to considerably different. For example for annual crops, seed size/yield has been proposed to be a measure of plant size and productivity, but this is unlikely to be the case since perennial plants such as trees take several years to flower and thus seed yield, if at all, is only an indicator of growth conditions that prevail during the year the plant flowered. Actually, in many instances a model system such as *Populus tremulaxtremuloides* is much better for reliably confirming genes that can be used for increasing biomass production. Also the important biomass of trees is usually the wood, this being a tissue not present in many of the commonly used plants model systems such as *Arabidopsis*. Thus, poplar, which has a small, fully sequenced genome and is phylogenetically related to *Arabidopsis*, provides an excellent model for studying traits that are unique in woody perennials, giving unique insights into useful trait genes for biomass production and wood quality. A plant's traits, including its biochemical, developmental, or phenotypic characteristics that enhance yield or tolerance to various abiotic stresses, may be controlled through a number of cellular processes. One important way to manipulate that control is through transcription factors—proteins that influence the expression of a particular gene or sets of genes. Transformed and transgenic plants that comprise cells having altered levels of at least one selected transcription factor, for example, possess advantageous or desirable traits. Strategies for manipulating traits by altering a plant cell's transcription factor content can therefore result in plants and crops with commercially valuable properties.

We have thus identified important polynucleotide and polypeptide sequences for producing commercially valuable plants as well as the methods for making them and using them. Other aspects and embodiments of the instant claims are described below and can be derived from the teachings of this disclosure as a whole.

SUMMARY OF THE INVENTION

The present disclosure pertains to expression vectors, transgenic plants comprising the expression vectors of the disclosure, and methods for making and using the transgenic plants of the disclosure. The expression vectors and transgenic plants each comprise a recombinant polynucleotide of the disclosure that encodes a transcription factor polypeptide. The polypeptide is encompassed by the present disclosure in that it shares an amino acid percent identity with any of SEQ ID NOs: 298, 120, 175, 226, 330, 400, 436, 514, or 606, and said percent identity may be at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100%; or the recombinant nucleic acid sequence the encodes the polypeptide specifically hybridizes to the complement of a DNA sequence set forth in the Sequence Listing, such as SEQ ID NOs: 297, 119, 174, 225, 329, 399, 435, 513, or 605, under stringent conditions comprising two wash steps at least as stringent as 6×SSC at 65° C. of 10-30 minutes for each wash step; or 0.2× to 2×SSC and 0.1% SDS at 50° C. to 65° C. for 10-30 minutes per wash step.

When the polypeptide is overexpressed in a plant, the polypeptide is capable of regulating transcription in the plant and confers to the plant at least one regulatory activity. This results in the plant having an altered trait, as compared to a control plant (e.g., a wild-type plant of the same species, or a non-transformed plant, or a plant transformed with an "empty vector" that does not comprise a recombinant nucleic acid sequence encoding a polypeptide of the instant disclosure). The altered trait that is conferred to the plant as a result of expressing the polypeptide may be one (or more) of the following: increased biomass, altered sugar sensing, altered tolerance to abiotic stress, altered water use efficiency for increased biomass production in dry climates, altered development and morphology, altered flowering time, altered biochemistry or hormone sensitivity, altered wood quality.

The altered tolerance to abiotic stress conferred by the polypeptides of the instant disclosure may be one (or more) of the following: increased tolerance to water deprivation, as indicated by reduced .sup.13C discrimination, increased time to wilting, increased tolerance to dehydration, increased tolerance to soil drought, lower soil water content at wilting, increased time to wilting; increased tolerance to hyperosmotic stress, as indicated by increased tolerance to sodium chloride and sucrose; increased nutrient uptake, as indicated by altered C/N sensing; increased tolerance to low nutrient conditions as indicated by increased tolerance to low nitrogen condition, increased tolerance to phosphate-free medium; or increased cold tolerance.

The altered development and morphology may be characterized by one or more of the following traits, including fruit traits, and more specifically including: increased fruit weight; increased growth, increased diameter, increased growth rate, increased height, increased dry weight, increased leaf area, increased specific leaf area, increased internode length, decreased "Root/Shoot" ratio, increased leaf dry weight, decreased biomass; increased wood density, increased density of trichome; altered light response, such as reduced shade avoidance indicated by altered leaf orientation; increased root mass; short root; darker green leaves; larger leaves; increased biomass; increased petiole length; late senescence; increased vascular bundles in stem; increased seedling vigor; and increased flower size and number relative to a control plant.

The altered flowering time is early or late flowering.

The altered leaf biochemistry is indicated by increased leaf glucosinolate M39480 level, The altered hormone sensitivity is measured by decreased sensitivity to ABA, higher seed lutein content.

This instant disclosure also provides a method to confer an altered trait to plants. The method steps comprise transforming a plant with at least one expression vector of the instant disclosure to produce a transgenic plant that has the altered trait as compared to a control plant.

BRIEF DESCRIPTION OF THE SEQUENCE LISTING AND DRAWINGS

The Sequence Listing provides exemplary polynucleotide and polypeptide sequences of the instant disclosure. The traits associated with the use of the sequences are included in the Examples.

Incorporation of the Sequence Listing The copy of the Sequence Listing, being submitted electronically with this patent application, provided under 37 CFR .sctn.1.821-1.825, is a read-only memory computer-readable file in ASCII text format. The Sequence Listing is named "MBI-0094PCT_ST25.txt". The electronic file of the Sequence Listing was created on Feb. 7, 2011, and is 1,887,615 bytes in size (1.79 metabytes measured in MS-WINDOWS). The Sequence Listing is herein incorporated by reference in its entirety.

FIG. 1 shows an exemplary growth curve of a poplar plant. The height growth rate increased during the first part of growth, then the plants reached their maximum height growth rate, and then the growth rate declined as the plants became larger. A height growth rate value was calculated as the slope of a linear function fitted over four consecutive height data points, e.g. for data point 1-4, data point 2-5 etc. in a step-wise manner. A maximum height growth rate, defined as the maximum value produced from step-wise linear regression analysis, was computed for each plant.

Figure 2:
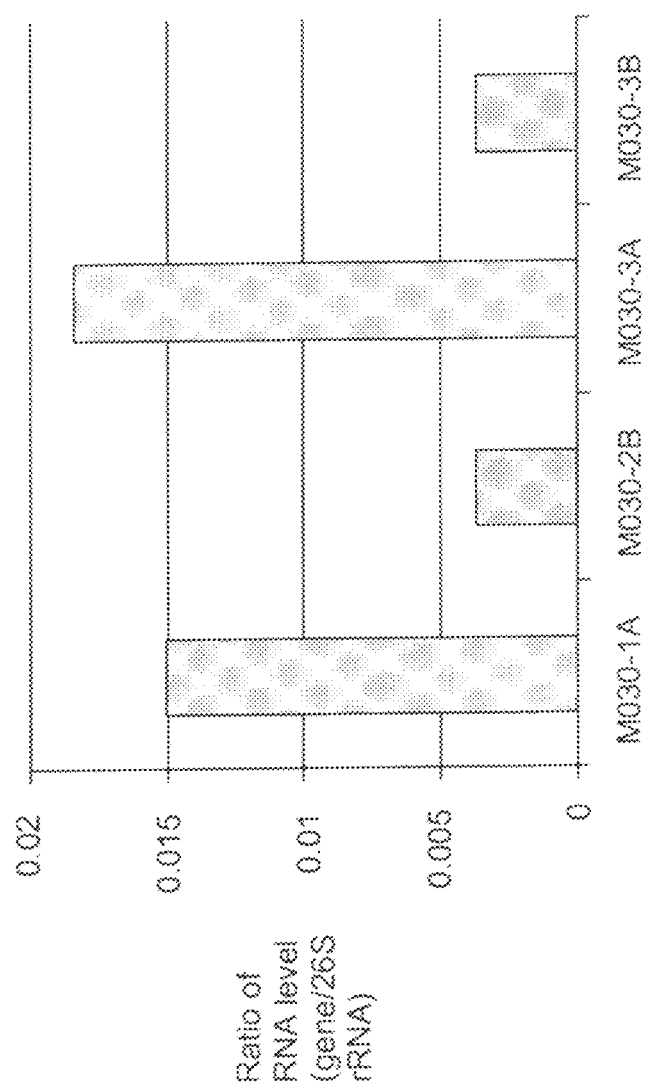

FIG. 2 shows the result of a Q-PCR analysis of the M030 construct group, which represents transgenic plants overexpressing G2552. Q-PCR experiments were performed on tissue culture materials obtained from one leaf of a plant from each transgenic line. The X axis represents various transgenic lines of the construct group M030. The Y axis represents the ratio of the mRNA level of G2552 over the mRNA level of ribosomal subunit 26S rRNA gene. The results suggested that the expression levels of G2552 in M030-1A and M030-3A lines were higher than expression level in line M030-2B. The result correlated well to the increased growth observed in plants of M030-1A and M030-3A lines.

Figure 3:
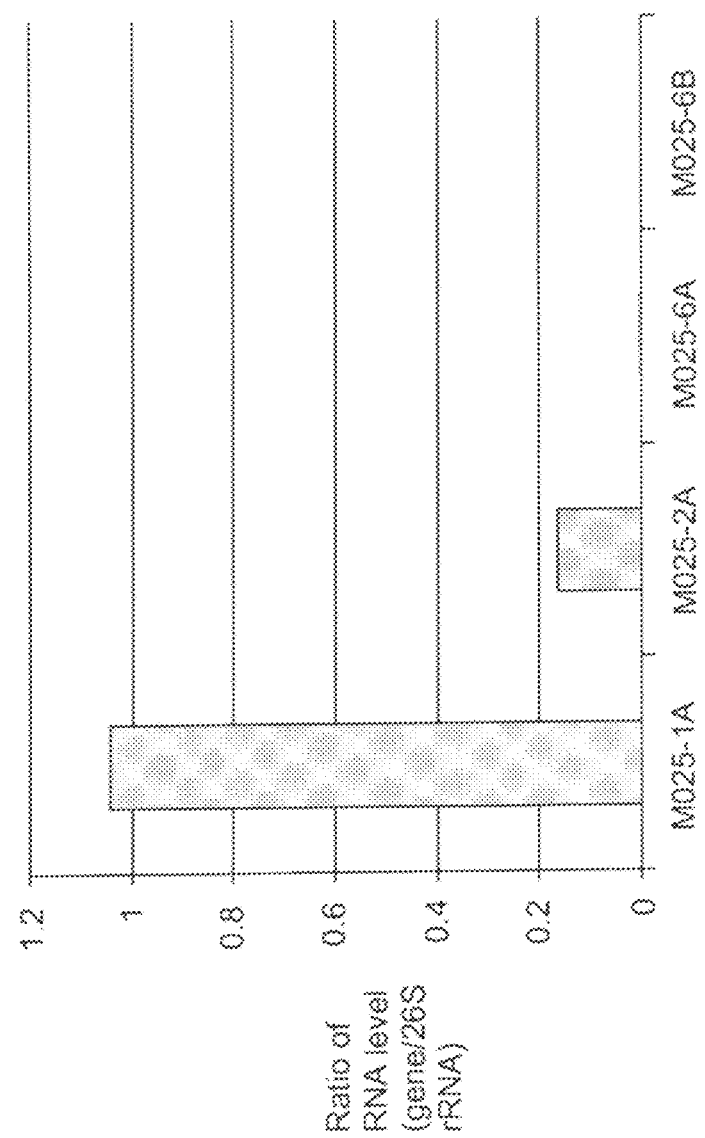

FIG. 3 shows the result a Q-PCR analysis on the M025 construct group, which represents transgenic plants overexpressing G2724. Q-PCR experiments were performed on tissue culture materials obtained from one leaf of a plant from each transgenic line. The X axis represents various transgenic lines of the construct group M025. The Y axis represents the ratio of the mRNA level of G2724 over the mRNA level of ribosomal subunit 26S rRNA gene. The gene/26s-ratio of line M025-1A suggests that the expression level in this line was 6 times higher than expression level of line M025-2A and 260 times higher than expression level of line M025-6A. These differences in expression levels in parallel with the growth studies confirmed that this gene affects growth.

DETAILED DESCRIPTION OF THE INVENTION

The present disclosure relates to polynucleotides and polypeptides for modifying phenotypes of plants, particularly those associated with greater biomass, greater tolerance to hyperosmotic stress, and/or greater abiotic stress tolerance. Throughout this disclosure, various information sources are referred to and/or are specifically incorporated. The information sources include scientific journal articles, patent documents, textbooks, and World Wide Web browser-inactive page addresses. While the reference to these information sources clearly indicates that they can be used by one of skill in the art, each and every one of the information sources cited herein are specifically incorporated in their entirety, whether or not a specific mention of "incorporation by reference" is noted. The contents and teachings of each and every one of the information sources can be relied on and used to make and use embodiments of the instant disclosure.

As used herein and in the appended claims, the singular forms "a", "an", and "the" include the plural reference unless the context clearly dictates otherwise. Thus, for example, a reference to "a host cell" includes a plurality of such host cells, and a reference to "a stress" is a reference to one or more stresses and equivalents thereof known to those skilled in the art, and so forth.

DEFINITIONS

"Nucleic acid molecule" refers to an oligonucleotide, polynucleotide or any fragment thereof. It may be DNA or RNA of genomic or synthetic origin, double-stranded or single-stranded, and combined with carbohydrate, lipids, protein, or other materials to perform a particular activity such as transformation or form a useful composition such as a peptide nucleic acid (PNA).

"Polynucleotide" is a nucleic acid molecule comprising a plurality of polymerized nucleotides, e.g., at least about 15 consecutive polymerized nucleotides. A polynucleotide may be a nucleic acid, oligonucleotide, nucleotide, or any fragment thereof. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like. The polynucleotide can be single-stranded or double-stranded DNA or RNA. The polynucleotide optionally comprises modified bases or a modified backbone. The polynucleotide can be, e.g., genomic DNA or RNA, a transcript (such as an mRNA), a cDNA, a PCR product, a cloned DNA, a synthetic DNA or RNA, or the like. The polynucleotide can be combined with carbohydrate, lipids, protein, or other materials to perform a particular activity such as transformation or form a useful composition such as a peptide nucleic acid (PNA). The polynucleotide can comprise a sequence in either sense or antisense orientations. "Oligonucleotide" is substantially equivalent to the terms amplimer, primer, oligomer, element, target, and probe and is preferably single-stranded.

"Gene" or "gene sequence" refers to the partial or complete coding sequence of a gene, its complement, and its 5' or 3' untranslated regions. A gene is also a functional unit of inheritance, and in physical terms is a particular segment or sequence of nucleotides along a molecule of DNA (or RNA, in the case of RNA viruses) involved in producing a polypeptide chain. The latter may be subjected to subsequent processing such as chemical modification or folding to obtain a functional protein or polypeptide. A gene may be isolated, partially isolated, or found with an organism's genome. By way of example, a transcription factor gene encodes a transcription factor polypeptide, which may be functional or require processing to function as an initiator of transcription.

Operationally, genes may be defined by the cis-trans test, a genetic test that determines whether two mutations occur in the same gene and that may be used to determine the limits of the genetically active unit (Rieger et al. (1976)). A gene generally includes regions preceding ("leaders"; upstream) and following ("trailers"; downstream) the coding region. A gene may also include intervening, non-coding sequences, referred to as "introns", located between individual coding segments, referred to as "exons". Most genes have an associated promoter region, a regulatory sequence 5' of the transcription initiation codon (there are some genes that do not have an identifiable promoter). The function of a gene may also be regulated by enhancers, operators, and other regulatory elements.

A "recombinant polynucleotide" is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a vector, or otherwise recombined with one or more additional nucleic acid.

An "isolated polynucleotide" is a polynucleotide, whether naturally occurring or recombinant, that is present outside the cell in which it is typically found in nature, whether purified or not. Optionally, an isolated polynucleotide is subject to one or more enrichment or purification procedures, e.g., cell lysis, extraction, centrifugation, precipitation, or the like.

A "polypeptide" is an amino acid sequence comprising a plurality of consecutive polymerized amino acid residues e.g., at least about 15 consecutive polymerized amino acid residues. In many instances, a polypeptide comprises a polymerized amino acid residue sequence that is a transcription factor or a domain or portion or fragment thereof. Additionally, the polypeptide may comprise: (i) a localization domain; (ii) an activation domain; (iii) a repression domain; (iv) an oligomerization domain; (v) a DNA-binding domain; or the like. The polypeptide optionally comprises modified amino acid residues, naturally occurring amino acid residues not encoded by a codon, non-naturally occurring amino acid residues.

"Protein" refers to an amino acid sequence, oligopeptide, peptide, polypeptide or portions thereof whether naturally occurring or synthetic.

"Portion", as used herein, refers to any part of a protein used for any purpose, but especially for the screening of a library of molecules which specifically bind to that portion or for the production of antibodies.

A "recombinant polypeptide" is a polypeptide produced by translation of a recombinant polynucleotide. A "synthetic polypeptide" is a polypeptide created by consecutive polymerization of isolated amino acid residues using methods well known in the art. An "isolated polypeptide," whether a naturally occurring or a recombinant polypeptide, is more enriched in (or out of) a cell than the polypeptide in its natural state in a wild-type cell, e.g., more than about 5% enriched, more than about 10% enriched, or more than about 20%, or more than about 50%, or more, enriched, i.e., alternatively denoted: 105%, 110%, 120%, 150% or more, enriched relative to wild type standardized at 100%. Such an enrichment is not the result of a natural response of a wild-type plant. Alternatively, or additionally, the isolated polypeptide is separated from other cellular components with which it is typically associated, e.g., by any of the various protein purification methods herein.

"Homology" refers to sequence similarity between a reference sequence and at least a fragment of a newly sequenced clone insert or its encoded amino acid sequence.

"Identity" or "similarity" refers to sequence similarity between two polynucleotide sequences or between two polypeptide sequences, with identity being a more strict comparison. The phrases "percent identity" and "% identity" refer to the percentage of sequence similarity found in a comparison of two or more polynucleotide sequences or two or more polypeptide sequences. Closely-related polynucleotides of the instant disclosure encode regulatory proteins, e.g., m transcription factors, that will have at least about 38% sequence identity including conservative substitutions, or at least about 55% sequence identity, or at least about 56%, or at least about 57%, or at least about 58%, or at least about 59%, or at least about 60%, or at least about 61%, or at least about 62% sequence identity, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%, or 100% amino acid residue sequence identity, to a polypeptide listed in the Sequence Listing or in Tables 1 or 16.

"Sequence similarity" refers to the percent similarity in base pair sequence (as determined by any suitable method) between two or more polynucleotide sequences. Two or more sequences can be anywhere from 0-100% similar, or any integer value there between. Identity or similarity can be determined by comparing a position in each sequence that may be aligned for purposes of comparison. When a position in the compared sequence is occupied by the same nucleotide base or amino acid, then the molecules are identical at that position. A degree of similarity or identity between polynucleotide sequences is a function of the number of identical, matching or corresponding nucleotides at positions shared by the polynucleotide sequences. A degree of identity of polypeptide sequences is a function of the number of identical amino acids at corresponding positions shared by the polypeptide sequences. A degree of homology or similarity of polypeptide sequences is a function of the number of amino acids at corresponding positions shared by the polypeptide sequences.

"Alignment" refers to a number of nucleotide bases or amino acid residue sequences aligned by lengthwise comparison so that components in common (i.e., nucleotide bases or amino acid residues at corresponding positions) may be visually and readily identified. The fraction or percentage of components in common is related to the homology or identity between the sequences. Alignments may be used to identify conserved domains and relatedness within these domains. An alignment may suitably be determined by means of computer programs known in the art, such as MACVECTOR software (1999) and Accelrys Gene v2.5 (2006) (Accelrys, Inc., San Diego, Calif.).

Two or more sequences may be "optimally aligned" with a similarity scoring method using a defined amino acid substitution matrix such as the BLOSUM62 scoring matrix. The preferred method uses a gap existence penalty and gap extension penalty that arrives at the highest possible score for a given pair of sequences. See, for example, Dayhoff et al. (1978) and Henikoff and Henikoff (1992). The BLOSUM62 matrix is often used as a default scoring substitution matrix in sequence alignment protocols such as Gapped BLAST® 2.0. The gap existence penalty is imposed for the introduction of a single amino acid gap in one of the aligned sequences, and the gap extension penalty is imposed for each additional empty amino acid position inserted into an already opened gap. The alignment is defined by the amino acids positions of each sequence at which the alignment begins and ends, and optionally by the insertion of a gap or multiple gaps in one or both sequences, so as to arrive at the highest possible score. Optimal alignment may be accomplished manually or with a computer-based alignment algorithm, such as gapped BLAST® 2.0 (Altschul et al, (1997); or at www.ncbi.nlm.nih.gov. See U.S. Patent Application US20070004912.

A "conserved domain" or "conserved region" as used herein refers to a region in heterologous polynucleotide or polypeptide sequences where there is a relatively high degree of sequence identity between the distinct sequences. For example, an "AT-hook" domain", such as is found in a polypeptide member of AT-hook transcription factor family, is an example of a conserved domain. An" AP2" domain", such as is found in a polypeptide member of AP2 transcription factor family, is another example of a conserved domain. With respect to polynucleotides encoding presently disclosed transcription factors, a conserved domain is preferably at least nine base pairs (bp) in length. A conserved domain with respect to presently disclosed polypeptides refers to a domain within a transcription factor family that exhibits a higher degree of sequence homology, such as at least about 38% amino acid sequence identity including conservative substitutions, or at least about 42% sequence identity, or at least about 45% sequence identity, or at least about 48% sequence identity, or at least about 50% sequence identity, or at least about 51% sequence identity, or at least about 52% sequence identity, or at least about 53% sequence identity, or at least about 54% sequence identity, or at least about 55% sequence identity, or at least about 56% sequence identity, or at least about 57% sequence identity, or at least about 58% sequence identity, or at least about 59% sequence identity, or at least about 60% sequence identity, or at least about 61% sequence identity, or at least about 62% sequence identity, or at least about 63% sequence identity, or at least about 64% sequence identity, or at least about 65% sequence identity, or at least about 66% sequence identity, or at least about 67% sequence identity, or at least about 68% sequence identity, or at least about 69% sequence identity, or at least about 70% sequence identity, or at least about 71% sequence identity, or at least about 72% sequence identity, or at least about 73% sequence identity, or at least about 74% sequence identity, or at least about 75% sequence identity, or at least about 76% sequence identity, or at least about 77% sequence identity, or at least about 78% sequence identity, or at least about 79% sequence identity, or at least about 80% sequence identity, or at least about 81% sequence identity, or at least about 82% sequence identity, or at least about 83% sequence identity, or at least about 84% sequence identity, or at least about 85% sequence identity, or at least about 86% sequence identity, or at least about 87% sequence identity, or at least about 88% sequence identity, or at least about 89% sequence identity, or at least about 90% sequence identity, or at least about 91% sequence identity, or at least about 92% sequence identity, or at least about 93% sequence identity, or at least about 94% sequence identity, or at least about 95% sequence identity, or at least about 96% sequence identity, or at least about 97% sequence identity, or at least about 98% sequence identity, or at least about 99% sequence identity, or 100% amino acid residue sequence identity, to a conserved domain of a polypeptide of the instant disclosure, such as those listed in the present tables or Sequence Listing. Sequences that possess or encode for conserved domains that meet these criteria of percentage identity, and that have comparable biological activity to the present transcription factor sequences, thus being members of a clade of transcription factor polypeptides, are envisioned by the instant disclosure. A fragment or domain can be referred to as outside a conserved domain, outside a consensus sequence, or outside a consensus DNA-binding site that is known to exist or that exists for a particular transcription factor class, family, or sub-family. In this case, the fragment or domain will not include the exact amino acids of a consensus sequence or consensus DNA-binding site of a transcription factor class, family or sub-family, or the exact amino acids of a particular transcription factor consensus sequence or consensus DNA-binding site. Furthermore, a particular fragment, region, or domain of a polypeptide, or a polynucleotide encoding a polypeptide, can be "outside a conserved domain" if all the amino acids of the fragment, region, or domain fall outside of a defined conserved domain(s) for a polypeptide or protein. Sequences having lesser degrees of identity but comparable biological activity are considered to be equivalents.

As one of ordinary skill in the art recognizes, conserved domains may be identified as regions or domains of identity to a specific consensus sequence (see, for example, Riechmann et al. (2000a, 2000b)). One of ordinary skill in the art would also recognize that the presence of any of the conserved domains provided in Table 1 in a polypeptide is highly correlated with the function of the polypeptide in which these domains are found. By using alignment methods well known in the art, the conserved domains of the plant transcription factors, for example, for the AT-hook proteins (Reeves and Beckerbauer (2001); and Reeves (2001)), may be determined The conserved domains for many of the polypeptide sequences of the claims are listed in Table 1. Also, the polypeptides of Table 1 or 16 have conserved domains specifically indicated by amino acid coordinate start and stop sites. A comparison of the regions of these polypeptides allows one of skill in the art (see, for example, Reeves and Nissen (1995)) to identify domains or conserved domains for any of the polypeptides listed or referred to in this disclosure.

"Complementary" refers to the natural hydrogen bonding by base pairing between purines and pyrimidines. For example, the sequence A-C-G-T (5'→3') forms hydrogen bonds with its complements A-C-G-T (5'→3') or A-C-G-U (5'→3'). Two single-stranded molecules may be considered partially complementary, if only some of the nucleotides bond, or "completely complementary" if all of the nucleotides bond. The degree of complementarity between nucleic acid strands affects the efficiency and strength of hybridization and amplification reactions. "Fully complementary" refers to the case where bonding occurs between every base pair and its complement in a pair of sequences, and the two sequences have the same number of nucleotides.

The terms "highly stringent" or "highly stringent condition" refer to conditions that permit hybridization of DNA strands whose sequences are highly complementary, wherein these same conditions exclude hybridization of significantly mismatched DNAs. Polynucleotide sequences capable of hybridizing under stringent conditions with the disclosed polynucleotides may be, for example, variants of the disclosed polynucleotide sequences, including allelic or splice variants, or sequences that encode orthologs or paralogs of presently disclosed polypeptides. Nucleic acid hybridization methods are disclosed in detail by Kashima et al. (1985), Sambrook et al. (1989), and by Haymes et al. (1985), which references are incorporated herein by reference.

In general, stringency is determined by the temperature, ionic strength, and concentration of denaturing agents (e.g., formamide) used in a hybridization and washing procedure (for a more detailed description of establishing and determining stringency, see the section "Identifying Polynucleotides or Nucleic Acids by Hybridization", below). The degree to which two nucleic acids hybridize under various conditions of stringency is correlated with the extent of their similarity. Thus, similar nucleic acid sequences from a variety of sources, such as within a plant's genome (as in the case of paralogs) or from another plant (as in the case of orthologs) that may perform similar functions can be isolated on the basis of their ability to hybridize with known transcription factor sequences. Numerous variations are possible in the conditions and means by which nucleic acid hybridization can be performed to isolate transcription factor sequences having similarity to transcription factor sequences known in the art and are not limited to those explicitly disclosed herein. Such an approach may be used to isolate polynucleotide sequences having various degrees of similarity with disclosed transcription factor sequences, such as, for example, encoded transcription factors having 38% or greater identity with the conserved domain of disclosed transcription factors.

The terms "paralog" and "ortholog" are defined below in the section entitled "Orthologs and Paralogs". In brief, orthologs and paralogs are evolutionarily related genes that have similar sequences and functions. Orthologs are structurally related genes in different species that are derived by a speciation event. Paralogs are structurally related genes within a single species that are derived by a duplication event.

The term "equivalog" describes members of a set of homologous proteins that are conserved with respect to function since their last common ancestor (Haft et al., 2003). Related proteins are grouped into equivalog families, and otherwise into protein families with other hierarchically defined homology types.

In general, the term "variant" refers to molecules with some differences, generated synthetically or naturally, in their base or amino acid sequences as compared to a reference (native) polynucleotide or polypeptide, respectively. These differences include substitutions, insertions, deletions or any desired combinations of such changes in a native polynucleotide of amino acid sequence.

With regard to polynucleotide variants, differences between presently disclosed polynucleotides and polynucleotide variants are limited so that the nucleotide sequences of the former and the latter are closely similar overall and, in many regions, identical. Due to the degeneracy of the genetic code, differences between the former and latter nucleotide sequences may be silent (i.e., the amino acids encoded by the polynucleotide are the same, and the variant polynucleotide sequence encodes the same amino acid sequence as the presently disclosed polynucleotide. Variant nucleotide sequences may encode different amino acid sequences, in which case such nucleotide differences will result in amino acid substitutions, additions, deletions, insertions, truncations or fusions with respect to the similar disclosed polynucleotide sequences. These variations may result in polynucleotide variants encoding polypeptides that share at least one functional characteristic. The degeneracy of the genetic code also dictates that many different variant polynucleotides can encode identical and/or substantially similar polypeptides in addition to those sequences illustrated in the Sequence Listing.

Also within the scope of the claims is a variant of a transcription factor nucleic acid listed in the Sequence Listing, that is, one having a sequence that differs from the one of the polynucleotide sequences in the Sequence Listing, or a complementary sequence, that encodes a functionally equivalent polypeptide (i.e., a polypeptide having some degree of equivalent or similar biological activity) but differs in sequence from the sequence in the Sequence Listing, due to degeneracy in the genetic code. Included within this definition are polymorphisms that may or may not be readily detectable using a particular oligonucleotide probe of the polynucleotide encoding polypeptide, and improper or unexpected hybridization to allelic variants, with a locus other than the normal chromosomal locus for the polynucleotide sequence encoding polypeptide.

"Allelic variant" or "polynucleotide allelic variant" refers to any of two or more alternative forms of a gene occupying the same chromosomal locus. Allelic variation arises naturally through mutation, and may result in phenotypic polymorphism within populations. Gene mutations may be "silent" or may encode polypeptides having altered amino acid sequence. "Allelic variant" and "polypeptide allelic variant" may also be used with respect to polypeptides, and in this case the terms refer to a polypeptide encoded by an allelic variant of a gene.

"Splice variant" or "polynucleotide splice variant" as used herein refers to alternative forms of RNA transcribed from a gene. Splice variation naturally occurs as a result of alternative sites being spliced within a single transcribed RNA molecule or between separately transcribed RNA molecules, and may result in several different forms of mRNA transcribed from the same gene. Thus, splice variants may encode polypeptides having different amino acid sequences, which may or may not have similar functions in the organism. "Splice variant" or "polypeptide splice variant" may also refer to a polypeptide encoded by a splice variant of a transcribed mRNA.

As used herein, "polynucleotide variants" may also refer to polynucleotide sequences that encode paralogs and orthologs of the presently disclosed polypeptide sequences. "Polypeptide variants" may refer to polypeptide sequences that are paralogs and orthologs of the presently disclosed polypeptide sequences.

Differences between presently disclosed polypeptides and polypeptide variants are limited so that the sequences of the former and the latter are closely similar overall and, in many regions, identical. Presently disclosed polypeptide sequences and similar polypeptide variants may differ in amino acid sequence by one or more substitutions, additions, deletions, fusions and truncations, which may be present in any combination. These differences may produce silent changes and result in a functionally equivalent transcription factor. Thus, it will be readily appreciated by those of skill in the art, that any of a variety of polynucleotide sequences is capable of encoding the regulatory polypeptides, e.g., transcription factors and transcription factor homolog polypeptides, of the instant disclosure. A polypeptide sequence variant may have "conservative" changes, wherein a substituted amino acid has similar structural or chemical properties. Deliberate amino acid substitutions may thus be made on the basis of similarity in polarity, charge, solubility, hydrophobicity, hydrophilicity, and/or the amphipathic nature of the residues, as long as a significant amount of the functional or biological activity of the transcription factor is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine. More rarely, a variant may have "non-conservative" changes, e.g., replacement of a glycine with a tryptophan. Similar minor variations may also include amino acid deletions or insertions, or both. Related polypeptides may comprise, for example, additions and/or deletions of one or more N-linked or O-linked glycosylation sites, or an addition and/or a deletion of one or more cysteine residues. Guidance in determining which and how many amino acid residues may be substituted, inserted or deleted without abolishing functional or biological activity may be found using computer programs well known in the art, for example, DNASTAR software (see U.S. Pat. No. 5,840,544).

"Fragment", with respect to a polynucleotide, refers to a clone or any part of a polynucleotide molecule that retains a usable, functional characteristic. Useful fragments include oligonucleotides and polynucleotides that may be used in hybridization or amplification technologies or in the regulation of replication, transcription or translation. A "polynucleotide fragment" refers to any subsequence of a polynucleotide, typically, of at least about 9 consecutive nucleotides, preferably at least about 30 nucleotides, more preferably at least about 50 nucleotides, of any of the sequences provided herein. Exemplary polynucleotide fragments are the first sixty consecutive nucleotides of the transcription factor polynucleotides listed in the Sequence Listing Exemplary fragments also include fragments that comprise a region that encodes an conserved domain of a transcription factor. Exemplary fragments also include fragments that comprise a conserved domain of a transcription factor. Fragments may also include subsequences of polypeptides and protein molecules, or a subsequence of the polypeptide. Fragments may have uses in that they may have antigenic potential. In some cases, the fragment or domain is a subsequence of the polypeptide which performs at least one biological function of the intact polypeptide in substantially the same manner, or to a similar extent, as does the intact polypeptide. For example, a polypeptide fragment can comprise a recognizable structural motif or functional domain such as a DNA-binding site or domain that binds to a DNA promoter region, an activation domain, or a domain for protein-protein interactions, and may initiate transcription. Fragments can vary in size from as few as 3 amino acid residues to the full length of the intact polypeptide, but are preferably at least about 30 amino acid residues in length and more preferably at least about 60 amino acid residues in length.

The instant claims also encompasses production of DNA sequences that encode transcription factors and transcription factor derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding transcription factors or any fragment thereof.

"Derivative" refers to the chemical modification of a nucleic acid molecule or amino acid sequence. Chemical modifications can include replacement of hydrogen by an alkyl, acyl, or amino group or glycosylation, pegylation, or any similar process that retains or enhances biological activity or lifespan of the molecule or sequence.

The term "plant" includes whole plants, shoot vegetative organs/structures (for example, leaves, stems and tubers), roots, flowers and floral organs/structures (for example, bracts, sepals, petals, stamens, carpels, anthers and ovules), seed (including embryo, endosperm, and seed coat) and fruit (the mature ovary), plant tissue (for example, vascular tissue, ground tissue, and the like) and cells (for example, guard cells, egg cells, and the like), and progeny of same. The class of plants that can be used in the method of the claims is generally as broad as the class of higher and lower plants amenable to transformation techniques, including angiosperms (monocotyledonous and dicotyledonous plants), gymnosperms, ferns, horsetails, psilophytes, lycophytes, bryophytes, and multicellular algae.

A "control plant" as used in the instant disclosure refers to a plant cell, seed, plant component, plant tissue, plant organ or whole plant used to compare against transgenic or genetically modified plant for the purpose of identifying an enhanced phenotype in the transgenic or genetically modified plant. A control plant may in some cases be a transgenic plant line that comprises an empty vector or marker gene, but does not contain the recombinant polynucleotide of the present disclosure that is expressed in the transgenic or genetically modified plant being evaluated. In general, a control plant is a plant of the same line or variety as the transgenic or genetically modified plant being tested. A suitable control plant would include a genetically unaltered or non-transgenic plant of the parental line used to generate a transgenic plant herein.

A "transgenic plant" refers to a plant that contains genetic material not found in a wild-type plant of the same species, variety or cultivar. The genetic material may include a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation, but any method can be used as one of skill in the art recognizes.

A transgenic plant may contain an expression vector or cassette. The expression cassette typically comprises a polypeptide-encoding sequence operably linked (i.e., under regulatory control of) to appropriate inducible or constitutive regulatory sequences that allow for the controlled expression of polypeptide. The expression cassette can be introduced into a plant by transformation or by breeding after transformation of a parent plant. A plant refers to a whole plant as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell.

"Wild type" or "wild-type", as used herein, refers to a plant cell, seed, plant component, plant tissue, plant organ or whole plant that has not been genetically modified or treated in an experimental sense. Wild-type cells, seed, components, tissue, organs or whole plants may be used as controls to compare levels of expression and the extent and nature of trait modification with cells, tissue or plants of the same species in which a transcription factor expression is altered, e.g., in that it has been knocked out, overexpressed, or ectopically expressed.

A "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar concentrations, or by the observation of the expression level of a gene or genes, e.g., by employing Northern analysis, RT-PCR, microarray gene expression assays, or reporter gene expression systems, or by agricultural observations such as hyperosmotic stress tolerance or yield. Any technique can be used to measure the amount of, comparative level of, or difference in any selected chemical compound or macromolecule in the transgenic plants, however.

As used herein an "enhanced trait" means a characteristic of a transgenic plant that includes, but is not limited to, an enhanced agronomic or forestry trait characterized by enhanced plant morphology, physiology, growth and development, yield, nutritional enhancement, disease or pest resistance, or environmental or chemical tolerance. In more specific aspects, an enhanced trait is selected from group of enhanced traits consisting of enhanced water use efficiency, enhanced cold tolerance, increased yield, enhanced nitrogen use efficiency, enhanced seed protein and enhanced seed oil. In an important aspect of the instant disclosure, the enhanced trait is enhanced yield including increased yield under non-stress conditions and increased yield under environmental stress conditions. Stress conditions may include, for example, water deficit, drought, shade, fungal disease, viral disease, bacterial disease, insect infestation, nematode infestation, cold temperature exposure (e.g., 4° C.-8° C.), heat exposure (e.g., temperatures of at least 32° C.), hyperosmotic stress, reduced nitrogen nutrient availability or nitrogen-limited conditions, reduced phosphorus nutrient availability or phosphorus-limited conditions and high plant density. "Yield" can be affected by many properties including without limitation, leaf area, specific leaf area, internode length, "Root/Shoot" ratio, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also affected by efficiency of germination (including germination in stressed conditions), growth rate (including growth rate in stressed conditions), ear number, seed number per ear, seed size, composition of seed (starch, oil, protein) and characteristics of seed fill.

Desired traits include accelerated onset of flowering, delayed onset of flowering, enhanced tolerance to biotic or abiotic stress, increased yield, enhanced disease resistance, altered sterility, reduced sensitivity to light, greater early season growth, greater height, greater stem diameter, increased biomass, increased photosynthetic rate, increased resistance to lodging, increased internode length, increased leaf area, increased specific leaf area, increased internode length, decreased "Root/Shoot" ratio, increased secondary rooting, greater cold tolerance, greater tolerance to water deprivation, greater tolerance to salt, greater tolerance to heat, altered sugar sensing, reduced stomatal conductance, altered C/N sensing, increased low nitrogen tolerance, increased low phosphorus tolerance, increased tolerance to hyperosmotic stress, greater late season growth and vigor, increased number of mainstem nodes, and/or greater canopy coverage. The identification of compounds through the methods as described allows efficient and convenient delivery of the desired traits during a critical stage of plant life cycle.

Increased yield of a transgenic plant can be measured in a number of ways, including plant volume, plant biomass, test weight, seed number per plant, seed weight, seed number per unit area (i.e. seeds, or weight of seeds, per acre), bushels per acre (bu/a), tonnes per acre, tons per acre, and/or kilo per hectare. For trees, yield could be measured as average wood production per year over the rotation cycle. Wood production could be measured in m.sup.3, tons, and/or energy content (MJ). For example, maize yield may be measured as production of shelled corn kernels per unit of production area, for example in bushels per acre or metric tons per hectare, often reported on a moisture adjusted basis, for example at 15.5 percent moisture. Increased yield may result from improved utilization of water and key biochemical compounds, such as nitrogen, phosphorous and carbohydrate, or from improved responses to environmental stresses, such as cold, heat, drought, salt, and attack by pests or pathogens. Recombinant DNA can also be used to provide plants having improved growth and development, and ultimately increased yield, as the result of modified expression of plant growth regulators or modification of cell cycle or photosynthesis pathways. Also of interest is the generation of transgenic plants that demonstrate enhanced yield with respect to a seed component that may or may not correspond to an increase in overall plant yield. Such properties include enhancements in seed oil, seed molecules such as tocopherol, protein and starch, or oil particular oil components as may be manifest by an alteration in the ratios of seed components.

"Trait modification" or "trait alteration" refers to a detectable difference in a characteristic in a plant ectopically expressing a polynucleotide or polypeptide of the instant disclosure relative to a plant not doing so, such as a wild-type plant. In some cases, the trait modification can be evaluated quantitatively. For example, the trait modification can entail at least about a 2% increase or decrease, or an even greater difference, in an observed trait as compared with a control or wild-type plant. It is known that there can be a natural variation in the modified trait. Therefore, the trait modification observed entails a change of the normal distribution and magnitude of the trait in the plants as compared to control or wild-type plants.

Trait modifications or alterations of particular interest include those to seed (such as embryo or endosperm), fruit, root, flower, leaf, stem, shoot, seedling or the like, including: enhanced tolerance to environmental conditions including freezing, chilling, heat, drought, water saturation, radiation and ozone; improved tolerance to microbial, fungal or viral diseases; improved tolerance to pest infestations, including nematodes, mollicutes, parasitic higher plants or the like; decreased herbicide sensitivity; improved tolerance of heavy metals or enhanced ability to take up heavy metals; improved growth under poor photoconditions (e.g., low light and/or short day length), or changes in expression levels of genes of interest. Other phenotype that can be modified or altered relate to the production of plant metabolites, such as variations in the production of taxol, tocopherol, tocotrienol, sterols, phytosterols, vitamins, wax monomers, anti-oxidants, amino acids, lignins, cellulose, tannins, prenyllipids (such as chlorophylls and carotenoids), glucosinolates, and terpenoids, enhanced or compositionally altered protein or oil production (especially in seeds), or modified sugar (insoluble or soluble) and/or starch composition. Physical plant characteristics that can be modified include cell development (such as the number of trichomes), wood fiber properties such as; fiber length, fiber width, fiber thickness and chemical composition, fruit and seed size and number, yields of plant parts such as stems, leaves, inflorescences, and roots, the stability of the seeds during storage, characteristics of the seed pod (e.g., susceptibility to shattering), root hair length and quantity, internode distances, or the quality of seed coat. Plant growth characteristics that can be modified include plant height, diameter, weight, growth rate, germination rate of seeds, vigor of plants and seedlings, leaf and flower senescence, male sterility, apomixis, flowering time, flower abscission, rate of nitrogen uptake, osmotic sensitivity to soluble sugar concentrations, biomass or transpiration characteristics, as well as plant architecture characteristics such as apical dominance, branching patterns, number of organs, organ identity, organ shape or size.

When two or more plants have "similar morphologies", "substantially similar morphologies", "a morphology that is substantially similar", or are "morphologically similar", the plants have comparable forms or appearances, including analogous features such as overall dimensions, height, width, mass, root mass, shape, glossiness, color, stem diameter, leaf size, leaf dimension, leaf density, internode distance, branching, root branching, number and form of inflorescences, and other macroscopic characteristics, and the individual plants are not readily distinguishable based on morphological characteristics alone.

"Modulates" refers to a change in activity (biological, chemical, or immunological) or lifespan resulting from specific binding between a molecule and either a nucleic acid molecule or a protein.

The term "transcript profile" refers to the expression levels of a set of genes in a cell in a particular state, particularly by comparison with the expression levels of that same set of genes in a cell of the same type in a reference state. For example, the transcript profile of a particular transcription factor in a suspension cell is the expression levels of a set of genes in a cell knocking out or overexpressing that transcription factor compared with the expression levels of that same set of genes in a suspension cell that has normal levels of that transcription factor. The transcript profile can be presented as a list of those genes whose expression level is significantly different between the two treatments, and the difference ratios. Differences and similarities between expression levels may also be evaluated and calculated using statistical and clustering methods.

With regard to transcription factor gene knockouts as used herein, the term "knockout" refers to a plant or plant cell having a disruption in at least one transcription factor gene in the plant or cell, where the disruption results in a reduced expression or activity of the transcription factor encoded by that gene compared to a control cell. The knockout can be the result of, for example, genomic disruptions, including transposons, tilling, and homologous recombination, antisense constructs, sense constructs, RNA silencing constructs, or RNA interference. A T-DNA insertion within a transcription factor gene is an example of a genotypic alteration that may abolish expression of that transcription factor gene.

"Ectopic expression or altered expression" in reference to a polynucleotide indicates that the pattern of expression in, e.g., a transgenic plant or plant tissue, is different from the expression pattern in a wild-type plant or a reference plant of the same species. The pattern of expression may also be compared with a reference expression pattern in a wild-type plant of the same species. For example, the polynucleotide or polypeptide is expressed in a cell or tissue type other than a cell or tissue type in which the sequence is expressed in the wild-type plant, or by expression at a time other than at the time the sequence is expressed in the wild-type plant, or by a response to different inducible agents, such as hormones or environmental signals, or at different expression levels (either higher or lower) compared with those found in a wild-type plant. The term also refers to altered expression patterns that are produced by lowering the levels of expression to below the detection level or completely abolishing expression. The resulting expression pattern can be transient or stable, constitutive or inducible. In reference to a polypeptide, the term "ectopic expression or altered expression" further may relate to altered activity levels resulting from the interactions of the polypeptides with exogenous or endogenous modulators or from interactions with factors or as a result of the chemical modification of the polypeptides.

The term "overexpression" as used herein refers to a greater expression level of a gene in a plant, plant cell or plant tissue, compared to expression of that gene in a wild-type plant, cell or tissue, at any developmental or temporal stage. Overexpression can occur when, for example, the genes encoding one or more transcription factors are under the control of a regulatory control element such as a strong or constitutive promoter (e.g., the cauliflower mosaic virus 35 S transcription initiation region). Overexpression may also be achieved by placing a gene of interest under the control of an inducible or tissue specific promoter, or may be achieved through integration of transposons or engineered T-DNA molecules into regulatory regions of a target gene. Thus, overexpression may occur throughout a plant, in specific tissues of the plant, or in the presence or absence of particular environmental signals, depending on the promoter or overexpression approach used.

Overexpression may take place in plant cells normally lacking expression of polypeptides functionally equivalent or identical to the present transcription factors. Overexpression may also occur in plant cells where endogenous expression of the present transcription factors or functionally equivalent molecules normally occurs, but such normal expression is at a lower level. Overexpression thus results in a greater than normal production, or "overproduction" of the transcription factor in the plant, cell or tissue.

The term "transcription regulating region" refers to a DNA regulatory sequence that regulates expression of one or more genes in a plant when a transcription factor having one or more specific binding domains binds to the DNA regulatory sequence. Transcription factors of the instant disclosure possess a conserved domain. The transcription factors of the instant disclosure also comprise an amino acid subsequence that forms a transcription activation domain that regulates expression of one or more abiotic stress tolerance genes in a plant when the transcription factor binds to the regulating region.

A "nucleic acid construct" may comprise a polypeptide-encoding sequence operably linked (that is, under regulatory control of) to appropriate inducible, cell-specific, tissue-specific, cell-enhanced, tissue-enhanced, condition-enhanced, developmental, or constitutive regulatory sequences that allow for the controlled expression of the polypeptide. The expression vector or cassette can be introduced into a plant by transformation or by breeding after transformation of a parent plant. A plant refers to a whole plant as well as to a plant part, such as seed, fruit, leaf, or root, plant tissue, plant cells or any other plant material, for example, a plant explant, to produce a recombinant plant (for example, a recombinant plant cell comprising the nucleic acid construct) as well as to progeny thereof, and to in vitro systems that mimic biochemical or cellular components or processes in a cell. Plant materials can also be materials obtained by grinding the solid residues of a plant.

A constitutive promoter is active under most environmental conditions, and in most plant parts.

Tissue-specific, tissue-enhanced (that is, tissue-preferred), cell type-specific, and inducible promoters constitute non-constitutive promoters. Promoters under developmental control include promoters that preferentially initiate transcription in certain tissues, such as xylem, leaves, roots, or seeds. Such promoters are examples of tissue-enhanced or tissue-preferred promoters (see U.S. Pat. No. 7,365,186). Tissue-enhanced promoters can be found upstream and operatively linked to DNA sequences normally transcribed in higher levels in certain plant tissues or specifically in certain plant tissues, respectively. "Cell-enhanced", "tissue-enhanced", or "tissue-specific" regulation thus refer to the control of gene or protein expression, for example, by a promoter, which drives expression that is not necessarily totally restricted to a single type of cell or tissue, but where expression is elevated in particular cells or tissues to a greater extent than in other cells or tissues within the organism, and in the case of tissue-specific regulation, in a manner that is primarily elevated in a specific tissue. Tissue-enhanced or preferred promoters have been described in, for example, U.S. Pat. No. 7,365,186, or U.S. Pat. No. 7,619,133.

A "condition-enhanced" promoter refers to a promoter that activates a gene in response to a particular environmental stimulus, for example, an abiotic stress, infection caused by a pathogen, light treatment, etc., and that drives expression in a unique pattern which may include expression in specific cell and/or tissue types within the organism (as opposed to a constitutive expression pattern in all cell types of an organism at all times).

Transcription Factors Modify Expression of Endogenous Genes

A transcription factor may include, but is not limited to, any polypeptide that can activate or repress transcription of a single gene or a number of genes. As one of ordinary skill in the art recognizes, transcription factors can be identified by the presence of a region or domain of structural similarity or identity to a specific consensus sequence or the presence of a specific consensus DNA-binding site or DNA-binding site motif (see, for example, Riechmann et al. (2000a) supra). The plant transcription factors encoded by the present sequences may belong to one of the following transcription factor families: the MYB transcription factor family (Martin and Paz-Ares (1997) Trends Genet. 13: 67-73); the WRKY protein family (Ishiguro and Nakamura (1994) Mol. Gen. Genet. 244: 563-571); the zinc finger protein (Z) family (Klug and Schwabe (1995) FASEB J. 9: 597-604); Takatsuji (1998) Cell. Mol. Life. Sci. 54: 582-596); the HLH/MYC protein family (Littlewood et al. (1994)); the bZIP family of transcription factors (Foster et al. (1994)); the triple helix (TH) family (Dehesh et al. (1990)); the RING-zinc family (Jensen et al. (1998)). As indicated by any part of the list above and as known in the art, transcription factors have been sometimes categorized by class, family, and sub-family according to their structural content and consensus DNA-binding site motif, for example. Many of the classes and many of the families and sub-families are listed here. However, the inclusion of one sub-family and not another, or the inclusion of one family and not another, does not mean that the claims do not encompass polynucleotides or polypeptides of a certain family or sub-family. The list provided here is merely an example of the types of transcription factors and the knowledge available concerning the consensus sequences and consensus DNA-binding site motifs that help define them as known to those of skill in the art (each of the references noted above are specifically incorporated herein by reference). A transcription factor may include, but is not limited to, any polypeptide that can activate or repress transcription of a single gene or a number of genes. This polypeptide group includes, but is not limited to, DNA-binding proteins, DNA-binding protein binding proteins, protein kinases, protein phosphatases, protein methyltransferases, GTP-binding proteins, and receptors, and the like.

Generally, the transcription factors encoded by the present sequences are involved in cell differentiation and proliferation and the regulation of growth. Accordingly, one skilled in the art would recognize that by expressing the present sequences in a plant, one may change the expression of autologous genes or induce the expression of introduced genes. By affecting the expression of similar autologous sequences in a plant that have the biological activity of the present sequences, or by introducing the present sequences into a plant, one may alter a plant's phenotype to one with improved traits related to osmotic stresses. The disclosed sequences may also be used to transform a plant and introduce desirable traits not found in the wild-type cultivar or strain. Plants may then be identified and/or selected for those that express a disclosed sequence, or produce the most desirable degree of over- or under-expression of target genes of interest, and exhibit coincident trait improvement resulting from said over- or under-expression of the target genes, including the phenotypic traits provided in Table 16. Expression of genes that encode transcription factors that modify expression of endogenous genes, polynucleotides, and proteins are well known in the art. In addition, transgenic plants comprising isolated polynucleotides encoding transcription factors may also modify expression of endogenous genes, polynucleotides, and proteins. Examples include Peng et al. (1997) and Peng et al. (1999). In addition, many others have demonstrated that an *Arabidopsis* transcription factor expressed in an exogenous plant species elicits the same or very similar phenotypic response. See, for example, Fu et al. (2001); Nandi et al. (2000); Coupland (1995); and Weigel and Nilsson (1995)).

In another example, Mandel et al. (1992), and Suzuki et al. (2001), teach that a transcription factor expressed in another plant species elicits the same or very similar phenotypic response of the endogenous sequence, as often predicted in earlier studies of *Arabidopsis* transcription factors in *Arabidopsis* (see Mandel et al. (1992); Suzuki et al. (2001)). Other examples include Milner et al. (2001); Kim et al. (2001); Kyozuka and Shimamoto (2002); Boss and Thomas (2002); He et al. (2000); and Robson et al. (2001).

In yet another example, Gilmour et al. (1998) teach an *Arabidopsis* AP2 transcription factor, CBF.sub.1, which, when overexpressed in transgenic plants, increases plant freezing tolerance. Jaglo et al. (2001) further identified sequences in *Brassica napus* which encode CBF-like genes and that transcripts for these genes accumulated rapidly in response to low temperature. Transcripts encoding CBF-like proteins were also found to accumulate rapidly in response to low temperature in wheat, as well as in tomato. An alignment of the CBF proteins from *Arabidopsis, B. napus*, wheat, rye, and tomato revealed the presence of conserved consecutive amino acid residues, PKK/RPAGRxKFx ETRHP and DSAWR, which bracket the AP2/EREBP DNA binding domains of the proteins and distinguish them from other members of the AP2/EREBP protein family. (Jaglo et al. (2001))

Transcription factors mediate cellular responses and control traits through altered expression of genes containing cis-acting nucleotide sequences that are targets of the introduced transcription factor. It is well appreciated in the art that the effect of a transcription factor on cellular responses or a cellular trait is determined by the particular genes whose expression is either directly or indirectly (e.g., by a cascade of transcription factor binding events and transcriptional changes) altered by transcription factor binding. In a global analysis of transcription comparing a standard condition with one in which a transcription factor is overexpressed, the resulting transcript profile associated with transcription factor overexpression is related to the trait or cellular process controlled by that transcription factor. For example, the PAP2 gene and other genes in the MYB family have been shown to control anthocyanin biosynthesis through regulation of the expression of genes known to be involved in the anthocyanin biosynthetic pathway (Bruce et al. (2000); and Borevitz et al. (2000)). Further, global transcript profiles have been used successfully as diagnostic tools for specific cellular states (e.g., cancerous vs. non-cancerous; Bhattacharjee et al. (2001); and Xu et al. (2001)). Consequently, it is evident to one skilled in the art that similarity of transcript profile upon overexpression of different transcription factors would indicate similarity of transcription factor function.

Polypeptides and Polynucleotides

The instant disclosure provides, inter alia, regulatory proteins, including transcription factors (TFs), and transcription factor homolog polypeptides, and isolated or recombinant polynucleotides encoding the polypeptides, or novel sequence variant polypeptides or polynucleotides encoding novel variants of transcription factors derived from the specific sequences provided in the Sequence Listing. Also provided are methods for modifying a plant's biomass by modifying for example the size or number of leaves or seed or the growth rate of a plant by controlling a number of cellular processes, and for increasing a plant's resistance or tolerance to disease or abiotic stresses, respectively. These methods are based on the ability to alter the expression of critical regulatory molecules that may be conserved between diverse plant species. Related conserved regulatory molecules may be originally discovered in a model system such as *Arabidopsis* and homologous, functional molecules then discovered in other plant species. The latter may then be used to confer increased biomass, disease resistance or abiotic stress tolerance in diverse plant species.

Exemplary polynucleotides encoding the disclosed polypeptides were identified in the *Arabidopsis thaliana* GenBank database using publicly available sequence analysis programs and parameters. Sequences initially identified were then further characterized to identify sequences comprising specified sequence strings corresponding to sequence motifs present in families of known transcription factors. In addition, further exemplary polynucleotides encoding the disclosed polypeptides were identified in the plant GenBank database using publicly available sequence analysis programs and parameters. Sequences initially identified were then further characterized to identify sequences comprising specified sequence strings corresponding to sequence motifs present in families of known transcription factors. Polynucleotide sequences meeting such criteria were confirmed as transcription factors.

Additional polynucleotides were identified by screening *Arabidopsis thaliana* and/or other plant cDNA libraries with probes corresponding to known transcription factors under low stringency hybridization conditions. Additional sequences, including full length coding sequences, were subsequently recovered by the rapid amplification of cDNA ends (RACE) procedure using a commercially available kit according to the manufacturer's instructions. Where necessary, multiple rounds of RACE are performed to isolate 5' and 3' ends. The full-length cDNA was then recovered by a routine end-to-end polymerase chain reaction (PCR) using primers specific to the isolated 5' and 3' ends. Exemplary sequences are provided in the Sequence Listing.

Many of the sequences in the Sequence Listing, derived from diverse plant species, have been ectopically expressed in overexpressor plants. The changes in the characteristic(s) or trait(s) of the plants were then observed and found to confer increased disease resistance, increase biomass and/or increased abiotic stress tolerance. Therefore, the polynucleotides and polypeptides can be used to improve desirable characteristics of plants.

The disclosed polynucleotides were also ectopically expressed in overexpressor plant cells and the changes in the expression levels of a number of genes, polynucleotides, and/or proteins of the plant cells observed. Therefore, the polynucleotides and polypeptides can be used to change expression levels of a genes, polynucleotides, and/or proteins of plants or plant cells.

The disclosed polynucleotide sequences encode polypeptides that are members of well-known transcription factor families, including plant transcription factor families, as disclosed in Table 1. Generally, the transcription factors encoded by the present sequences are involved in cell differentiation and proliferation and the regulation of growth. Accordingly, one skilled in the art would recognize that by expressing the present sequences in a plant, one may change the expression of autologous genes or induce the expression of introduced genes. By affecting the expression of similar autologous sequences in a plant that have the biological activity of the present sequences, or by introducing the present sequences into a plant, one may alter a plant's phenotype to one with improved traits. The disclosed may also be used to transform a plant and introduce desirable traits not found in the wild-type cultivar or strain. Plants may then be selected for those that produce the most desirable degree of over- or under-expression of target genes of interest and coincident trait improvement.

The instantly disclosed sequences may be from any species, particularly plant species, in a naturally occurring form or from any source whether natural, synthetic, semi-synthetic or recombinant. The instantly disclosed sequences may also include fragments of the present amino acid sequences. Where "amino acid sequence" is recited to refer to an amino acid sequence of a naturally occurring protein molecule, "amino acid sequence" and like terms are not meant to limit the amino acid sequence to the complete native amino acid sequence associated with the recited protein molecule.

In addition to methods for modifying a plant phenotype by employing one or more disclosed polynucleotides and polypeptides described herein, said polynucleotides and polypeptides have a variety of additional uses. These uses include their use in the recombinant production (i.e., expression) of proteins; as regulators of plant gene expression, as diagnostic probes for the presence of complementary or partially complementary nucleic acids (including for detection of natural coding nucleic acids); as substrates for further reactions, e.g., mutation reactions, PCR reactions, or the like; as substrates for cloning e.g., including digestion or ligation reactions; and for identifying exogenous or endogenous modulators of the transcription factors. The polynucleotide can be, e.g., genomic DNA or RNA, a transcript (such as an mRNA), a cDNA, a PCR product, a cloned DNA, a synthetic DNA or RNA, or the like. The polynucleotide can comprise a sequence in either sense or antisense orientations.

Table 1 lists a number of polypeptides and includes the protein family to which each belongs, the amino acid residue coordinates for the conserved domains, and the conserved domain sequences of the respective polypeptides.

TABLE 1

Transcription factor families and conserved domains of the polypeptides

| GID | SEQ ID | Family | Amino acid coordinates in conserved domains |
|---|---|---|---|
| G2379 | 298 | TH | 19-110, 173-232 |
| G1730 | 120 | RING-C3H2C3 | 103-144 |
| G189 | 175 | WRKY | 240-297, 191-237 |
| G2142 | 226 | HLH/MYC | 42-100 |
| G2552 | 330 | HLH/MYC | 124-181 |
| G2724 | 400 | MYB-(R1)R2R3 | 7-113 |
| G287 | 436 | Zf_MIZ | 293-354 |
| G748 | 514 | Z-Dof | 112-140 |
| G878 | 606 | WRKY | 250-305, 415-475 |

G2379, and Related Sequences

G2379 (SEQ ID NO: 297, AT5G05550) encodes a member of the trihelix (TH) family of transcription factors (SEQ ID NO: 298). G2379 was identified in the sequence of BAC MOP10, GenBank accession number AB005241, released by the *Arabidopsis* Genome Initiative.

The annotation of G2379 in BAC AB005241 was experimentally confirmed. G2379 appears to be constitutively expressed in all tissues and environmental conditions tested. G2379 comprises a conserved TH (trihelix) domain (amino acids 19-110), and a second conserved domain (amino acids 173-232). The region corresponding to amino acids 24-56 is also known as an EST domain (Eukaryotic Sterol Transporter domain). G2379 and closely-related clade member sequences, including but not limited to those in Table 2, each comprise one or more conserved domains that are highly homologous to those in G2379 and are expected to function in a similar manner in each of these related sequences, that is, by playing a central role in transcriptional regulation and in the conferring of shared traits.

Effects of Overexpression of G2379 in Arabiodopsis

The function of this gene was analyzed using transgenic plants in which G2379 was expressed under the control of the 35S promoter. G2379 overexpressing plants showed increased seedling vigor when grown on media containing elevated sucrose levels. This phenotype might be indicative of either altered sugar sensing or increased tolerance of hyperosmotic stress. A number of plant lines were also noted to be late developing, which likely reflected a delay in the onset of flowering. Delay of flowering can be favorable in certain crops as it leads to increased yield, particularly vegetative biomass.

Effects of Overexpression of G2379 in Poplar

Transgenic poplar plants that overexpress G2379 (SEQ ID NO: 298) exhibited an increased time to wilting and a reduced .sup.13C discrimination, which are indications of enhanced drought tolerance and increased water use efficiency.

TABLE 2

Sequences closely related to G2379

| Polypeptide | SEQ ID NO: | Species |
|---|---|---|
| G2377-AT3G11100 | 300 | Arabidopsis thaliana |
| G2756-AT3G58630 | 302 | Arabidopsis thaliana |
| ACF87523 | 304 | Zea mays |
| ACG44857 | 306 | Zea mays |
| ACN35531 | 308 | Zea mays |
| NP_001142041 | 310 | Zea mays |
| NP_001151900 | 312 | Zea mays |
| Pt_564061 | 314 | Populus trichocarpa |
| Pt_567243 | 316 | Populus trichocarpa |
| Os04g36790 | 318 | Oryza sativa |
| CAN72489 | 320 | Vitis vinifera |
| CAO41403 | 322 | Vitis vinifera |
| XP_002270392 | 324 | Vitis vinifera |
| XP_002272959 | 326 | Vitis vinifera |
| XP_002280689 | 328 | Vitis vinifera |

G1730, and Related Sequences

G1730 (SEQ ID NO: 119, AT2G35420) was identified in the sequence of BAC T32F12, GenBank accession number AC005314, released by the *Arabidopsis* Genome Initiative. There is no other published or public information about the function of G1730. The G1730 polypeptide (SEQ ID NO: 120) belongs to the RING/C3H2C3 family of proteins, with a conserved RING/C3H2C3 domain corresponding to amino acids 103-144.

The full-length cDNA clone corresponding to G1730 was isolated from a proprietary library. Based on RT-PCR experiments, G1730 is highly expressed in all tissues except roots, but is markedly repressed in rosette leaves by cold or osmotic stress.

G1730 and closely-related clade member sequences, including but not limited to those in Table 3, each comprise a conserved RING/C3H2C3 domain that is expected to function in a similar manner in each of these related sequences, that is, by playing a central role in transcriptional regulation and in the conferring of shared traits.

Effects of Overexpression of G1730 in *Arabidopsis*

The function of G1730 was studied using transgenic plants in which the gene was expressed under the control of the 35S promoter. 35S::G1730 plants showed wild-type morphology but displayed an enhanced performance compared to controls when subjected to hyperosmotic stress in both mannitol and glucose germination assays. Given the expression profiles of the endogenous gene, and the putative role of RING C3H2C3 proteins in regulation of ubiquitin-dependent protein turnover, it is possible that G1730 acts as a modulator of factors involved in the response to abiotic stress. 35S::G1730 overexpressors showed enhanced tolerance in a soil drought assay.

Effects of Overexpression of G1730 in Poplar

Overexpression of G1730 under the control of 35S promoter resulted in increased drought tolerance, as the transgenic lines exhibited the phenotypes of lower soil water content at wilting, increased time to wilting and reduced .sup.13C discrimination.

TABLE 3

Sequences closely related to G1730

| Polypeptide | SEQ ID NO: | Species |
|---|---|---|
| Os10g42390 | 122 | Oryza sativa |

G189, and Related Sequences

G189 (SEQ ID NO: 174, AT2G23320) was identified in the sequence of BAC clone T20D16 (gene At2g23320/T20D16.5), GenBank accession number AAB87100). G189 (SEQ ID NO: 175) comprises a conserved plant zinc cluster domain (amino acid coordinates 191-237) and a conserved WRKY domain (amino acid coordinates 240-297). G189 and closely-related clade member sequences, including but not limited to those in Table 4, each comprise one or more conserved domains that are highly homologous to those in G189 that are expected to function in a similar manner in each of these related sequences, that is, by playing a central role in transcriptional regulation and in the conferring of shared traits.

Effects of Overexpression of G189 in *Arabidopsis*

The function of G189 was studied using transgenic plants in which the gene was expressed under the control of the 35S promoter. T1 G189 overexpressing plants showed leaves of larger area than wild type. This phenotype, which was observed in two different T1 plantings, became more apparent at late vegetative development. However, T2 plants were morphologically wild type, perhaps reflecting a critical dependence of the phenotype on the transgene expression levels. In wild type plants, G189 appears to be constitutively expressed. G189 overexpressing plants were wild type in all the physiological analyses performed. 35S::G189 transformants showed increased tolerance to an alteration in C/N balance brought about by an increase in sucrose levels in the absence of a nitrogen source.

Effects of Overexpression of G189 in Poplar

Overexpression of G189 under the control of 35S promoter resulted in enhanced plant growth as indicated by the phenotypes of increased growth rate, increased wood density, increased height and increased dry weight relative to controls.

TABLE 4

Sequences closely related to G189

| Polypeptide | SEQ ID NO: | Species |
|---|---|---|
| Pt_208696 | 176 | *Populus trichocarpa* |
| Pt_655096 | 178 | *Populus trichocarpa* |
| Glyma05g20710 | 180 | *Glycine max* |
| Glyma17g18480 | 182 | *Glycine max* |
| Glyma01g39600 | 184 | *Glycine max* |
| Glyma11g05650 | 186 | *Glycine max* |

G2142, and Related Sequences

G2142 (SEQ ID NO: 226) was identified by amino acid sequence similarity to other HLH/MYC proteins, and has a conserved basic helix-loop-helix (bHLH) domain (amino acids coordinates 42-100). G2142 (SEQ ID NO: 225, AT1G69010) is found in the sequence of the chromosome 1 BAC clone T6L1 (GenBank accession number AC011665, nid=g6358759), released by the *Arabidopsis* Genome Initiative.

G2142 and closely-related clade member sequences, including but not limited to those in Table 5, each comprise a conserved bHLH domain that is expected to function in a similar manner in each of these related sequences, that is, by playing a central role in transcriptional regulation and in the conferring of shared traits.

Effects of Overexpression of G2142 in *Arabidopsis*

The function of G2142 was studied using transgenic plants in which the gene was expressed under the control of the 35 S promoter. G2142 overexpressors were more tolerant to phosphate deprivation in a root growth assay, but this effect was rather subtle.

Effects of Overexpression of G2142 in Poplar

Overexpression of G2142 resulted in enhanced growth in poplar, as indicated by increased dry weight.

TABLE 5

Sequences closely related to G2142

| Polypeptide | SEQ ID NO: | Species |
|---|---|---|
| ACG60671 | 228 | *Brassica oleracea* |
| Pt_765981 | 230 | *Populus trichocarpa* |
| Pt_833648 | 232 | *Populus trichocarpa* |
| Glyma01g09010 | 234 | *Glycine max* |
| Glyma02g13670 | 236 | *Glycine max* |
| XP_002266685 | 238 | *Vitis vinifera* |

G2552, and Related Sequences

The sequence of G2552 (SEQ ID NO: 329, AT2G28160) was obtained from *Arabidopsis* genomic sequencing project, GenBank accession number AC005851, based on its protein sequence similarity within the conserved domain (amino acid coordinates: 124-181) to other bHLH/MYC related proteins in *Arabidopsis*. G2552 (polypeptide SEQ ID NO: 330) is uniformly expressed in all tissues and under all conditions tested.

G2552 and closely-related clade member sequences, including but not limited to those in Table 6, each comprise a conserved basic helix-loop-helix (bHLH) domain that is expected to function in a similar manner in each of these related sequences, that is, by playing a central role in transcriptional regulation and in the conferring of shared traits.

Effects of Overexpression of G2552 in *Arabidopsis*

The function of G2552 was studied using transgenic plants in which the gene was expressed under the control of the 35S promoter. Overexpression of G2552 in *Arabidopsis* resulted in an increase in leaf glucosinolate M39480 in T2 lines 10 and 18. 35S::G2552 plants were wild-type in morphology and development, as well as in the physiological analyses that were performed.

Effects of Overexpression of G2552 in Poplar

Overexpression of G2552 under the control of LMP1 promoter promoted growth in that transgenic lines overexpressing this gene had increased growth rate, increased diameter and increased height.

Effects of Overexpression of G2552 in Tomato

Transgenic lines overexpressing G2552 under the control of a AS1 promoter had increased biomass compared to controls.

TABLE 6

Sequences closely related to G2552

| Polypeptide | SEQ ID NO: | Species |
|---|---|---|
| Pt_768452 | 332 | *Populus trichocarpa* |
| Os04g31290 | 334 | *Oryza sativa* |
| Glyma11g19850 | 336 | *Glycine max* |
| Glyma12g08640 | 338 | *Glycine max* |
| Glyma12g30240 | 340 | *Glycine max* |
| Glyma13g39650 | 342 | *Glycine max* |
| CAN64538 | 344 | *Vitis vinifera* |
| CAO16746 | 346 | *Vitis vinifera* |
| XP_002272647 | 348 | *Vitis vinifera* |

G2724, and Related Sequences

G2724 (SEQ ID NO: 400) is a member of the (R1)R2R3 subfamily of MYB transcription factors and has a conserved MYB domain (amino acid coordinates 7-113). G2724 (SEQ ID NO: 399, AT1G48000) was identified in the sequence of BAC T2J15, GenBank accession number AC051631, released by the *Arabidopsis* Genome Initiative, and is also referred to as MYB112. G2724 and closely-related clade member sequences, including but not limited to those in Table 7, each comprise a conserved MYB domain that is expected to function in a similar manner in each of these related sequences, that is, by playing a central role in transcriptional regulation and in the conferring of shared traits.

According to RT-PCR, G2724 is expressed in all tissues tested except shoots. No induction of G2724 was observed in leaf tissue in response to any stress-related condition tested.

Effects of Overexpression of G2724 in *Arabidopsis*

The function of G2724 was analyzed using transgenic plants in which the gene was expressed under the control of the 35S promoter. Two of the 35S::G2724 T2 populations (lines 2 and 4) developed slightly flat leaves that were somewhat darker green than those of controls. Such effects were subtle, but were apparent again when the populations were re-grown. In addition to the effects on leaf coloration, many of the T2-2 plants produced short bushy inflorescence stems. 35S::G2724 plants were wild type in the physiological and biochemical analyses that were performed.

Effects of Overexpression of G2724 in Poplar

Overexpression of G2724 under the control of 35S promoter resulted in increased dry weight.

TABLE 7

Sequences closely related to G2724

| Polypeptide | SEQ ID NO: | Species |
|---|---|---|
| G1330-AT5G49620 | 402 | *Arabidopsis thaliana* |
| G2423-AT3G06490 | 404 | *Arabidopsis thaliana* |
| ACF83741 | 406 | *Zea mays* |
| ACF87244 | 408 | *Zea mays* |
| CAW40990 | 410 | *Zea mays* |
| CAW41108 | 412 | *Zea mays* |
| CAW62960 | 414 | *Zea mays* |
| CAW63076 | 416 | *Zea mays* |
| NP_001140397 | 418 | *Zea mays* |
| NP_001141891 | 420 | *Zea mays* |
| Pt_803466 | 422 | *Populus trichocarpa* |
| Os03g20090 | 424 | *Oryza sativa* |
| Os05g04210 | 426 | *Oryza sativa* |
| Glyma07g36430 | 428 | *Glycine max* |
| Glyma09g03690 | 430 | *Glycine max* |
| Glyma15g14620 | 432 | *Glycine max* |
| Glyma17g04170 | 434 | *Glycine max* |

G287, and Related Sequences

G287 (SEQ ID NO: 436) was identified by amino acid sequence similarity to a *Vicia* transcription factor X97908 (GI:2104682). G287 belongs to the Zf_MIZ family of proteins and comprises a conserved Zf-MIZ domain (amino acid coordinates 293-354). G287 polynucleotide (SEQ ID NO: 435, AT1G08910) is found in the sequence of the chromosome 1 BAC, F7G19 (AC000106.1 GI:2342673), released by the *Arabidopsis* Genome Initiative. G287 and closely-related clade member sequences, including but not limited to those in Table 8, each comprise a conserved Zf_MIZ domain that is expected to function in a similar manner in each of these related sequences, that is, by playing a central role in transcriptional regulation and in the conferring of shared traits.

RT-PCR tissue profiling reveals that G287 is expressed at moderate levels in all tissues examined.

Effects of Overexpression of G287 in *Arabidopsis*

The function of G287 was analyzed through its overexpression in *Arabidopsis*; 35S::G287 lines displayed a marginal increase in leaf size and vegetative biomass, particularly at late stages of development. However, it should be noted that this was a moderately low penetrance phenotype and was seen in only a relatively small proportion of the plants.

Effects of Overexpression of G287 in Poplar

Overexpression of G287 under the control of 35S promoter resulted in enhanced plant growth as indicated by the phenotypes of increased growth rate, height and dry weight relative to controls.

TABLE 8

Sequences closely related to G287

| Polypeptide | SEQ ID NO: | Species |
|---|---|---|
| G288-AT5G41580 | 438 | *Arabidopsis thaliana* |
| ACF83263 | 440 | *Zea mays* |
| NP_001137099 | 442 | *Zea mays* |
| Pt_554422 | 444 | *Populus trichocarpa* |
| Os06g06870 | 446 | *Oryza sativa* |
| Glyma01g43160 | 448 | *Glycine max* |
| Glyma01g43170 | 450 | *Glycine max* |
| Glyma11g02330 | 452 | *Glycine max* |

G748, and Related Sequences

G748 (SEQ ID NO: 513, AT3G47500) encodes SEQ ID NO: 514, a member of the Z-D of family transcription factors. A cDNA sequence for G748 was deposited in GenBank by Abbaraju and Oliver on Aug. 4, 1998. It encodes a protein containing a conserved region (amino acid coordinates 105-167) that comprises a highly conserved D of zinc-finger domain (amino acid coordinates 112-140) that was found to bind the H-protein promoter. The H protein is a component of the glycine decarboxylase multienzyme complex, which comprises over one-third of the soluble proteins in mitochondria isolated from the leaves of C3 plants (Oliver and Raman, 1995).

In wild-type plants, G748 is constitutively expressed, although at lower levels at the seedling stage. Expression levels are slightly lower upon infection with *E. orontii* and *Fusarium*.

G748 and closely-related clade member sequences, including but not limited to those in Table 9, each comprise a conserved D of zinc-finger domain that is expected to function in a similar manner in each of these related sequences, that is, by playing a central role in transcriptional regulation and in the conferring of shared traits.

Effects of Overexpression of G748 in *Arabidopsis*

A cDNA sequence was isolated and used to produce transgenic plants overexpressing G748. Overexpression of G748 resulted in a late flowering phenotype. Transgenic plants were generally large and dark green with more rosette leaves. Stems were thicker and more vascular bundles were noticeable in transverse sections. G748 overexpressors also produced more lutein in seeds. The physiology of the plant is similar to that of the controls, based on the assays which were performed.

Effects of Overexpression of G748 in Poplar

Overexpression of G748 resulted in enhanced growth, and overexpressors had increased growth rate, increased height, and increased wood density compared to controls.

TABLE 9

Sequences closely related to G748

| Polypeptide | SEQ ID NO: | Species |
|---|---|---|
| ACF80167 | 516 | Zea mays |
| ACG29289 | 518 | Zea mays |
| ACN34213 | 520 | Zea mays |
| NP_001131653 | 522 | Zea mays |
| Pt_556324 | 524 | Populus trichocarpa |
| Os03g07360 | 526 | Oryza sativa |
| Glyma04g33410 | 528 | Glycine max |
| Glyma05g00970 | 530 | Glycine max |
| Glyma06g20950 | 532 | Glycine max |
| Glyma17g10920 | 534 | Glycine max |
| CAN79859 | 536 | Vitis vinifera |
| XP_002281994 | 538 | Vitis vinifera |

G878, and Related Sequences

G878 (SEQ ID NO: 605, AT2G03340) corresponds to gene At2g03340 (AAD17441). No information is available about the function(s) of G878. G878 (SEQ ID NO: 606) belongs to the WRKY family of transcription factors, and has two conserved WRKY domains (amino acid coordinates 250-305 and amino acid coordinates 415-475, respectively). G878 is ubiquitously expressed and does not appear to be significantly induced by any of the conditions tested.

G878 and closely-related clade member sequences, including but not limited to those in Table 10, each comprise one or more conserved WRKY domains that is expected to function in a similar manner in each of these related sequences, that is, by playing a central role in transcriptional regulation and in the conferring of shared traits.

Effects of Overexpression of G878 in *Arabidopsis*

The function of G878 was studied using transgenic plants in which the gene was expressed under the control of the 35S promoter. Analysis of primary transformants revealed that overexpression of G878 delays the onset of flowering in *Arabidopsis*: 11/20 of the 35S::G878 T1 plants flowered approximately one week later than wild type under continuous light conditions. These plants were also darker green, had shorter stems, and senesced later than controls.

Effects of Overexpression of G878 in Poplar

Overexpression of G878 under the control of 35S promoter resulted in increased growth rate and increased height.

TABLE 10

Sequences closely related to G878

| Polypeptide | SEQ ID NO: | Species |
|---|---|---|
| G884-AT1G13960 | 608 | Arabidopsis thaliana |
| ACI14395 | 610 | Brassica oleracea |
| ACI14399 | 612 | Brassica oleracea |
| ACQ76803 | 614 | Brassica oleracea |
| ACF79201 | 616 | Zea mays |
| ACG29054 | 618 | Zea mays |
| ACG29858 | 620 | Zea mays |
| ACL52418 | 622 | Zea mays |
| ACL53176 | 624 | Zea mays |
| ACL53429 | 626 | Zea mays |
| CAW33611 | 628 | Zea mays |
| CAW55835 | 630 | Zea mays |
| NP_001130833 | 632 | Zea mays |
| NP_001147897 | 634 | Zea mays |
| Pt_577692 | 636 | Populus trichocarpa |
| Pt_800701 | 638 | Populus trichocarpa |
| Pt_803420 | 640 | Populus trichocarpa |
| Pt_833697 | 642 | Populus trichocarpa |
| Os03g33012 | 644 | Oryza sativa |
| Os12g32250 | 646 | Oryza sativa |
| Glyma01g06550 | 648 | Glycine max |
| Glyma02g12490 | 650 | Glycine max |
| Glyma07g35380 | 652 | Glycine max |
| Glyma08g26230 | 654 | Glycine max |
| Glyma18g49830 | 656 | Glycine max |
| Glyma20g03410 | 658 | Glycine max |
| AAT46067 | 660 | Vitis vinifera |
| CAO15031 | 662 | Vitis vinifera |
| CAP08301 | 664 | Vitis vinifera |
| XP_002264243 | 666 | Vitis vinifera |

Orthologs and Paralogs

Homologous sequences as described above can comprise orthologous or paralogous sequences. Several different methods are known by those of skill in the art for identifying and defining these functionally homologous sequences. Three general methods for defining orthologs and paralogs are described; an ortholog or paralog, including equivalogs, may be identified by one or more of the methods described below.

As described by Eisen (1998) Genome Res. 8: 163-167, evolutionary information may be used to predict gene function. It is common for groups of genes that are homologous in sequence to have diverse, although usually related, functions. However, in many cases, the identification of homologs is not sufficient to make specific predictions because not all homologs have the same function. Thus, an initial analysis of functional relatedness based on sequence similarity alone may not provide one with a means to determine where similarity ends and functional relatedness begins. Fortunately, it is well known in the art that protein function can be classified using phylogenetic analysis of gene trees combined with the corresponding species. Functional predictions can be greatly improved by focusing on how the genes became similar in sequence (i.e., by evolutionary processes) rather than on the sequence similarity itself (Eisen, supra). In fact, many specific examples exist in which gene function has been shown to correlate well with gene phylogeny (Eisen, supra). Thus, "[t]he first step in making functional predictions is the generation of a phylogenetic tree representing the evolutionary history of the gene of interest and its homologs. Such trees are distinct from clusters and other means of characterizing sequence similarity because they are inferred by techniques that help convert patterns of similarity into evolutionary relationships . . . . After the gene tree is inferred, biologically determined functions of the various homologs are overlaid onto the tree. Finally, the structure of the tree and the relative phylogenetic positions of genes of different functions are used to trace the history of functional changes, which is then used to predict functions of [as yet] uncharacterized genes" (Eisen, supra).

Within a single plant species, gene duplication may cause two copies of a particular gene, giving rise to two or more genes with similar sequence and often similar function known as paralogs. A paralog is therefore a similar gene formed by duplication within the same species. Paralogs typically cluster together or in the same clade (a group of similar genes) when a gene family phylogeny is analyzed using programs such as CLUSTAL (Thompson et al. (1994); Higgins et al. (1996)). Groups of similar genes can also be identified with pair-wise BLAST® analysis (Feng and Doolittle (1987)). For example, a clade of very similar MADS domain transcription factors from *Arabidopsis* all share a common function in flowering time (Ratcliffe et al. (2001)), and a group of very similar AP2 domain transcription factors from *Arabidopsis* are involved in tolerance of plants to freezing (Gilmour et al. (1998)). Analysis of groups of similar genes with similar function that fall within one clade can yield sub-sequences that are particular to the clade. These sub-sequences, known as consensus sequences, can not only be used to define the sequences within each clade, but define the functions of these genes; genes within a clade may contain paralogous sequences, or orthologous sequences that share the same function (see also, for example, Mount (2001)).

Speciation, the production of new species from a parental species, can also give rise to two or more genes with similar sequence and similar function. These genes, termed orthologs, often have an identical function within their host plants and are often interchangeable between species without losing function. Because plants have common ancestors, many genes in any plant species will have a corresponding orthologous gene in another plant species. Once a phylogenic tree for a gene family of one species has been constructed using a program such as CLUSTAL (Thompson et al. (1994); Higgins et al. (1996)) potential orthologous sequences can be placed into the phylogenetic tree and their relationship to genes from the species of interest can be determined. Orthologous sequences can also be identified by a reciprocal BLAST® strategy. Once an orthologous sequence has been identified, the function of the ortholog can be deduced from the identified function of the reference sequence.

Transcription factor gene sequences are conserved across diverse eukaryotic species lines (Goodrich et al. (1993); Lin et al. (1991); Sadowski et al. (1988)). Plants are no exception to this observation; diverse plant species possess transcription factors that have similar sequences and functions.

Orthologous genes from different organisms have highly conserved functions, and very often essentially identical functions (Lee et al. (2002); Remm et al. (2001)). Paralogous genes, which have diverged through gene duplication, may retain similar functions of the encoded proteins. In such cases, paralogs can be used interchangeably with respect to certain embodiments of the instant disclosure (for example, transgenic expression of a coding sequence). An example of such highly related paralogs is the CBF family, with three well-defined members in *Arabidopsis* and at least one ortholog in *Brassica napus*, all of which control pathways involved in both freezing and drought stress (Gilmour et al. (1998); Jaglo et al. (2001)).

Distinct *Arabidopsis* transcription factors, including G28 (found in U.S. Pat. No. 6,664,446), G482 (found in US Patent Application 20040045049), G867 (found in US Patent Application 20040098764), and G1073 (found in U.S. Pat. No. 6,717,034), have been shown to confer stress tolerance or increased biomass when the sequences are overexpressed. The polypeptides sequences belong to distinct clades of transcription factor polypeptides that include members from diverse species. In each case, a significant number of clade member sequences derived from both eudicots and monocots have been shown to confer greater biomass or tolerance to stress when the sequences were overexpressed (unpublished data). These references may serve to represent the many studies that demonstrate that conserved transcription factor genes from diverse species are likely to function similarly (i.e., regulate similar target sequences and control the same traits), and that transcription factors may be transformed into diverse species to confer or improve traits.

At the nucleotide level, the claimed sequences will typically share at least about 30% or 40% nucleotide sequence identity, preferably at least about 50%, about 60%, about 70% or about 80% sequence identity, and more preferably about 85%, about 90%, about 95% or about 97% or more sequence identity to one or more of the listed full-length sequences, or to a listed sequence but excluding or outside of the region(s) encoding a known consensus sequence or consensus DNA-binding site, or outside of the region(s) encoding one or all conserved domains. The degeneracy of the genetic code enables major variations in the nucleotide sequence of a polynucleotide while maintaining the amino acid sequence of the encoded protein.

Percent identity can be determined electronically, e.g., by using the MEGALIGN program (DNASTAR, Inc. Madison, Wis.). The MEGALIGN program can create alignments between two or more sequences according to different methods, for example, the clustal method (see, for example, Higgins and Sharp (1988). The clustal algorithm groups sequences into clusters by examining the distances between all pairs. The clusters are aligned pairwise and then in groups. Other alignment algorithms or programs may be used, including Accelrys Gene, FASTA, BLAST®, or ENTREZ, and which may be used to calculate percent similarity. These are available as a part of the GCG sequence analysis package (University of Wisconsin, Madison, Wis.), and can be used with or without default settings. ENTREZ is available through the National Center for Biotechnology Information. In one embodiment, the percent identity of two sequences can be determined by the GCG program with a gap weight of 1, e.g., each amino acid gap is weighted as if it were a single amino acid or nucleotide mismatch between the two sequences (see U.S. Pat. No. 6,262,333). Software for performing BLAST® analyses is publicly available, e.g., through the National Center for Biotechnology Information (see internet website at www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul (1993); Altschul et al. (1990)). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST® algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1992). Unless otherwise indicated for comparisons of predicted polynucleotides, "sequence identity" refers to the % sequence identity generated from a tblastx using the NCBI version of the algorithm at the default settings using gapped alignments with the filter "off" (see, for example, internet website at www.ncbi.nlm.nih.gov/).

Other techniques for alignment are described by Doolittle (1996). Preferably, an alignment program that permits gaps in the sequence is utilized to align the sequences. The Smith-Waterman is one type of algorithm that permits gaps in sequence alignments (see Shpaer (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

The percentage similarity between two polypeptide sequences, e.g., sequence A and sequence B, may be calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between polynucleotide sequences can also be counted or calculated by other methods known in the art, e.g., the Jotun Hein method (see, for example, Hein (1990)) Identity between sequences can also be determined by other methods known in the art, e.g., by varying hybridization conditions (see US Patent Application No. 20010010913).

The percent identity between two polypeptide sequences can also be determined using Accelrys Gene v2.5 (2006) with default parameters: Pairwise Matrix: GONNET; Align Speed: Slow; Open Gap Penalty: 10.000; Extended Gap Penalty: 0.100; Multiple Matrix: GONNET; Multiple Open Gap Penalty: 10.000; Multiple Extended Gap Penalty: 0.05; Delay Divergent: 30; Gap Separation Distance: 8; End Gap Separation: false; Residue Specific Penalties: false; Hydrophilic Penalties: false; Hydrophilic Residues: GPSNDQEKR. The default parameters for determining percent identity between two polynucleotide sequences using Accelrys Gene are: Align Speed: Slow; Open Gap Penalty: 10.000; Extended Gap Penalty: 5.000; Multiple Open Gap Penalty: 10.000; Multiple Extended Gap Penalty: 5.000; Delay Divergent: 40; Transition: Weighted Thus, the instant disclosure provides methods for identifying a sequence similar or paralogous or orthologous or homologous to one or more polynucleotides as noted herein, or one or more target polypeptides encoded by the polynucleotides, or otherwise noted herein and may include linking or associating a given plant phenotype or gene function with a sequence. In the methods, a sequence database is provided (locally or across an interne or intranet) and a query is made against the sequence database using the relevant sequences herein and associated plant phenotypes or gene functions.

In addition, one or more polynucleotide sequences or one or more polypeptides encoded by the polynucleotide sequences may be used to search against a BLOCKS (Bairoch et al. (1997)), PFAM, and other databases which contain previously identified and annotated motifs, sequences and gene functions. Methods that search for primary sequence patterns with secondary structure gap penalties (Smith et al. (1992)) as well as algorithms such as Basic Local Alignment Search Tool (BLAST®; Altschul (1993); Altschul et al. (1990)), BLOCKS (Henikoff and Henikoff (1991)), Hidden Markov Models (HMM; Eddy (1996); Sonnhammer et al. (1997)), and the like, can be used to manipulate and analyze polynucleotide and polypeptide sequences encoded by polynucleotides. These databases, algorithms and other methods are well known in the art and are described in Ausubel et al. (1997), and in Meyers (1995).

A further method for identifying or confirming that specific homologous sequences control the same function is by comparison of the transcript profile(s) obtained upon over-expression or knockout of two or more related transcription factors. Since transcript profiles are diagnostic for specific cellular states, one skilled in the art will appreciate that genes that have a highly similar transcript profile (e.g., with greater than 50% regulated transcripts in common, or with greater than 70% regulated transcripts in common, or with greater than 90% regulated transcripts in common) will have highly similar functions. Fowler et al. (2002), have shown that three paralogous AP2 family genes (CBF1, CBF2 and CBF3), each of which is induced upon cold treatment, and each of which can condition improved freezing tolerance, have highly similar transcript profiles. Once a transcription factor has been shown to provide a specific function, its transcript profile becomes a diagnostic tool to determine whether paralogs or orthologs have the same function.

Furthermore, methods using manual alignment of sequences similar or homologous to one or more polynucleotide sequences or one or more polypeptides encoded by the polynucleotide sequences may be used to identify regions of similarity and conserved domains. Such manual methods are well-known of those of skill in the art and can include, for example, comparisons of tertiary structure between a polypeptide sequence encoded by a polynucleotide that comprises a known function and a polypeptide sequence encoded by a polynucleotide sequence that has a function not yet determined. Such examples of tertiary structure may comprise predicted alpha helices, beta-sheets, amphipathic helices, leucine zipper motifs, zinc finger motifs, proline-rich regions, cysteine repeat motifs, and the like.

Orthologs and paralogs of presently disclosed transcription factors may be cloned using compositions provided by the present disclosure according to methods well known in the art. cDNAs can be cloned using mRNA from a plant cell or tissue that expresses one of the present transcription factors. Appropriate mRNA sources may be identified by interrogating Northern blots with probes designed from the present transcription factor sequences, after which a library is prepared from the mRNA obtained from a positive cell or tissue. Transcription factor-encoding cDNA is then isolated using, for example, PCR, using primers designed from a presently disclosed transcription factor gene sequence, or by probing with a partial or complete cDNA or with one or more sets of degenerate probes based on the disclosed sequences. The cDNA library may be used to transform plant cells. Expression of the cDNAs of interest is detected using, for example, microarrays, Northern blots, quantitative PCR, or any other technique for monitoring changes in expression. Genomic clones may be isolated using similar techniques to those.

Examples of orthologs of the *Arabidopsis* polypeptide sequences and their functionally similar orthologs are listed in the Sequence Listing. In addition to the sequences in the Sequence Listing, the instant disclosure and claims encompass isolated nucleotide sequences that are phylogenetically and structurally similar to sequences listed in the Sequence Listing) and can function in a plant by increasing biomass, and/or and abiotic stress tolerance when ectopically expressed in a plant.

Identifying Polynucleotides or Nucleic Acids by Hybridization

Polynucleotides homologous to the sequences illustrated in the Sequence Listing and tables can be identified, e.g., by hybridization to each other under stringent or under highly stringent conditions. Single stranded polynucleotides hybridize when they associate based on a variety of well characterized physical-chemical forces, such as hydrogen bonding, solvent exclusion, base stacking and the like. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations (and number thereof), as described in more detail in the references cited below (e.g., Sambrook et al. (1989); Berger and Kimmel (1987); and Anderson and Young (1985)).

Encompassed by the instant disclosure are polynucleotide sequences that are capable of hybridizing to the claimed polynucleotide sequences, including any of the transcription factor polynucleotides within the Sequence Listing, and fragments thereof under various conditions of stringency (see, for example, Wahl and Berger (1987); and Kimmel (1987)). In addition to the nucleotide sequences listed in the Sequence Listing, full length cDNA, orthologs, and paralogs of the present nucleotide sequences may be identified and isolated using well-known methods. The cDNA libraries, orthologs, and paralogs of the present nucleotide sequences may be screened using hybridization methods to determine their utility as hybridization target or amplification probes.

With regard to hybridization, conditions that are highly stringent, and means for achieving them, are well known in the art. See, for example, Sambrook et al. (1989); Berger and Kimmel (1987), pages 467-469; and Anderson and Young (1985).

Stability of DNA duplexes is affected by such factors as base composition, length, and degree of base pair mismatch. Hybridization conditions may be adjusted to allow DNAs of different sequence relatedness to hybridize. The melting temperature (Tm) is defined as the temperature when 50% of the duplex molecules have dissociated into their constituent single strands. The melting temperature of a perfectly matched duplex, where the hybridization buffer contains formamide as a denaturing agent, may be estimated by the following equations:

$$Tm(°C.)=81.5+16.6(\log [Na+])+0.41(\% G+C)-0.62(\% \text{ formamide})-500/L \quad \text{(I) DNA-DNA:}$$

$$Tm(°C.)=79.8+18.5(\log [Na+])+0.58(\% G+C)+0.12(\% G+C)^2-0.5(\% \text{ formamide})-820/L \quad \text{(II) DNA-RNA:}$$

$$T_m(°C.)=79.8+18.5(\log [Na+])+0.58(\% G+C)+0.12(\% G+C)^2-0.35(\% \text{ formamide})-820/L \quad \text{(III) RNA-RNA:}$$

where L is the length of the duplex formed, [Na+] is the molar concentration of the sodium ion in the hybridization or washing solution, and % G+C is the percentage of (guanine+cytosine) bases in the hybrid. For imperfectly matched hybrids, approximately 1° C. is required to reduce the melting temperature for each 1% mismatch.

Hybridization experiments are generally conducted in a buffer of pH between 6.8 to 7.4, although the rate of hybridization is nearly independent of pH at ionic strengths likely to be used in the hybridization buffer (Anderson and Young (1985)). In addition, one or more of the following may be used to reduce non-specific hybridization: sonicated salmon sperm DNA or another non-complementary DNA, bovine serum albumin, sodium pyrophosphate, sodium dodecylsulfate (SDS), polyvinyl-pyrrolidone, ficoll and Denhardt's solution. Dextran sulfate and polyethylene glycol 6000 act to exclude DNA from solution, thus raising the effective probe DNA concentration and the hybridization signal within a given unit of time. In some instances, conditions of even greater stringency may be desirable or required to reduce non-specific and/or background hybridization. These conditions may be created with the use of higher temperature, lower ionic strength and higher concentration of a denaturing agent such as formamide.

Stringency conditions can be adjusted to screen for moderately similar fragments such as homologous sequences from distantly related organisms, or to highly similar fragments such as genes that duplicate functional enzymes from closely related organisms. The stringency can be adjusted either during the hybridization step or in the post-hybridization washes. Salt concentration, formamide concentration, hybridization temperature and probe lengths are variables that can be used to alter stringency (as described by the formula above). As a general guidelines high stringency is typically performed at $T_m$-5° C. to $T_m$-20° C., moderate stringency at $T_m$-20° C. to $T_m$-35° C. and low stringency at $T_m$-35° C. to $T_m$-50° C. for duplex >150 base pairs. Hybridization may be performed at low to moderate stringency (25-50° C. below $T_m$), followed by post-hybridization washes at increasing stringencies. Maximum rates of hybridization in solution are determined empirically to occur at $T_m$-25° C. for DNA-DNA duplex and $T_m$-15° C. for RNA-DNA duplex. Optionally, the degree of dissociation may be assessed after each wash step to determine the need for subsequent, higher stringency wash steps.

High stringency conditions may be used to select for nucleic acid sequences with high degrees of identity to the disclosed sequences. An example of stringent hybridization conditions obtained in a filter-based method such as a Southern or Northern blot for hybridization of complementary nucleic acids that have more than 100 complementary residues is about 5° C. to 20° C. lower than the thermal melting point ($T_m$) for the specific sequence at a defined ionic strength and pH. Conditions used for hybridization may include about 0.02 M to about 0.15 M sodium chloride, about 0.5% to about 5% casein, about 0.02% SDS or about 0.1% N-laurylsarcosine, about 0.001 M to about 0.03 M sodium citrate, at hybridization temperatures between about 50° C. and about 70° C. More preferably, high stringency conditions are about 0.02 M sodium chloride, about 0.5% casein, about 0.02% SDS, about 0.001 M sodium citrate, at a temperature of about 50° C. Nucleic acid molecules that hybridize under stringent conditions will typically hybridize to a probe based on either the entire DNA molecule or selected portions, e.g., to a unique subsequence, of the DNA.

Stringent salt concentration will ordinarily be less than about 750 mM NaCl and 75 mM trisodium citrate. Increasingly stringent conditions may be obtained with less than about 500 mM NaCl and 50 mM trisodium citrate, to even greater stringency with less than about 250 mM NaCl and 25 mM trisodium citrate. Low stringency hybridization can be obtained in the absence of organic solvent, e.g., formamide, whereas high stringency hybridization may be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. with formamide present. Varying additional parameters, such as hybridization time, the concentration of detergent, e.g., sodium dodecyl sulfate (SDS) and ionic strength, are well known to those skilled in the art. Various levels of stringency are accomplished by combining these various conditions as needed.

The washing steps that follow hybridization may also vary in stringency; the post-hybridization wash steps primarily determine hybridization specificity, with the most critical factors being temperature and the ionic strength of the final wash solution. Wash stringency can be increased by decreasing salt concentration or by increasing temperature. Stringent salt concentration for the wash steps will preferably be less than about 30 mM NaCl and 3 mM trisodium citrate, and most preferably less than about 15 mM NaCl and 1.5 mM trisodium citrate.

Thus, hybridization and wash conditions that may be used to bind and remove polynucleotides with less than the desired homology to the nucleic acid sequences or their complements that encode the present transcription factors include, for example:
0.2× to 2×SSC and 0.1% SDS at 50° C., 55° C., 60° C., 65° C., or 50° C. to 65° C.;
6×SSC at 65° C.;
50% formamide, 4×SSC at 42° C.; or
0.5×, 1×, or 1.5×SSC, 0.1% SDS at 50° C., 55° C., 60° C., or 65° C.;
with, for example, two wash steps of 10-30 minutes each. Useful variations on these conditions will be readily apparent to those skilled in the art. A formula for "SSC, 20×" may be found, for example, in Ausubel et al., 1997. A person of skill in the art would not expect substantial variation among polynucleotide species encompassed within the scope of the present disclosure because the highly stringent conditions set forth in the above formulae yield structurally similar polynucleotides.

If desired, one may employ wash steps of even greater stringency, including about 0.2×SSC, 0.1% SDS at 65° C. and washing twice, each wash step being about 30 minutes, or about 0.1×SSC, 0.1% SDS at 65° C. and washing twice for 30 minutes. The temperature for the wash solutions will ordinarily be at least about 25° C., and for greater stringency at least about 42° C. Hybridization stringency may be increased further by using the same conditions as in the hybridization steps, with the wash temperature raised about 3° C. to about 5° C., and stringency may be increased even further by using the same conditions except the wash temperature is raised about 6° C. to about 9° C. For identification of less closely related homologs, wash steps may be performed at a lower temperature, e.g., 50° C.

An example of a low stringency wash step employs a solution and conditions of at least 25° C. in 30 mM NaCl, 3 mM trisodium citrate, and 0.1% SDS over 30 minutes. Greater stringency may be obtained at 42° C. in 15 mM NaCl, with 1.5 mM trisodium citrate, and 0.1% SDS over 30 minutes. Even higher stringency wash conditions are obtained at 65° C.-68° C. in a solution of 15 mM NaCl, 1.5 mM trisodium citrate, and 0.1% SDS. Wash procedures will generally employ at least two final wash steps. Additional variations on these conditions will be readily apparent to those skilled in the art (see, for example, US Patent Application No. 20010010913).

Stringency conditions can be selected such that an oligonucleotide that is perfectly complementary to the coding oligonucleotide hybridizes to the coding oligonucleotide with at least about a 5-10× higher signal to noise ratio than the ratio for hybridization of the perfectly complementary oligonucleotide to a nucleic acid encoding a transcription factor known as of the filing date of the application. It may be desirable to select conditions for a particular assay such that a higher signal to noise ratio, that is, about 15× or more, is obtained. Accordingly, a subject nucleic acid will hybridize to a unique coding oligonucleotide with at least a 2× or greater signal to noise ratio as compared to hybridization of the coding oligonucleotide to a nucleic acid encoding known polypeptide. The particular signal will depend on the label used in the relevant assay, e.g., a fluorescent label, a colorimetric label, a radioactive label, or the like. Labeled hybridization or PCR probes for detecting related polynucleotide sequences may be produced by oligolabeling, nick translation, end-labeling, or PCR amplification using a labeled nucleotide.

Encompassed by the instant disclosure are polynucleotide sequences that are capable of hybridizing to the claimed polynucleotide sequences, including any of the transcription factor polynucleotides within the Sequence Listing, and fragments thereof under various conditions of stringency (see, for example, Wahl and Berger (1987), pages 399-407; and Kimmel (1987)). In addition to the nucleotide sequences in the Sequence Listing, full length cDNA, orthologs, and paralogs of the present nucleotide sequences may be identified and isolated using well-known methods. The cDNA libraries, orthologs, and paralogs of the present nucleotide sequences may be screened using hybridization methods to determine their utility as hybridization target or amplification probes.

Sequence Variations

It will be readily appreciated by those of skill in the art, that any of a variety of polynucleotide sequences are capable of encoding the transcription factors and transcription factor homolog polypeptides of the instant disclosure. Due to the degeneracy of the genetic code, many different polynucleotides can encode identical and/or substantially similar polypeptides in addition to those sequences illustrated in the Sequence Listing. Nucleic acids having a sequence that differs from the sequences shown in the Sequence Listing, or complementary sequences, that encode functionally equivalent peptides (i.e., peptides having some degree of equivalent or similar biological activity) but differ in sequence from the sequence shown in the sequence listing due to degeneracy in the genetic code, are also within the scope of the instant claims.

Altered polynucleotide sequences encoding polypeptides include those sequences with deletions, insertions, or substitutions of different nucleotides, resulting in a polynucleotide encoding a polypeptide with at least one functional characteristic of the instant polypeptides. Included within this definition are polymorphisms which may or may not be readily detectable using a particular oligonucleotide probe of the polynucleotide encoding the instant polypeptides, and improper or unexpected hybridization to allelic variants, with a locus other than the normal chromosomal locus for the polynucleotide sequence encoding the instant polypeptides.

Allelic variant refers to any of two or more alternative forms of a gene occupying the same chromosomal locus. Allelic variation arises naturally through mutation, and may result in phenotypic polymorphism within populations. Gene mutations can be silent (i.e., no change in the encoded polypeptide) or may encode polypeptides having altered amino acid sequence. The term allelic variant is also used herein to denote a protein encoded by an allelic variant of a gene. Splice variant refers to alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Allelic variants of the polynucleotides disclosed in this application, including those containing silent mutations and those in which mutations result in amino acid sequence changes, are within the scope of the present claims, as are proteins which are allelic variants of polypeptides of the claims. cDNAs generated from alternatively spliced mRNAs, which retain the properties of the transcription factor are included within the scope of the present claims, as are polypeptides encoded by such cDNAs and mRNAs. Allelic variants and splice variants of these sequences can be cloned by probing cDNA or genomic libraries from different individual organisms or tissues according to standard procedures known in the art (see U.S. Pat. No. 6,388,064).

For example, Table 11 illustrates, e.g., that the codons AGC, AGT, TCA, TCC, TCG, and TCT all encode the same amino acid: serine. Accordingly, at each position in the sequence where there is a codon encoding serine, any of the above trinucleotide sequences can be used without altering the encoded polypeptide.

TABLE 11

Genetic code

| Amino acid | | | Possible Codons | | | | |
|---|---|---|---|---|---|---|---|
| Alanine | Ala | A | GCA | GCC | GCG | GCU | |
| Cysteine | Cys | C | TGC | TGT | | | |
| Aspartic acid | Asp | D | GAC | GAT | | | |
| Glutamic acid | Glu | E | GAA | GAG | | | |
| Phenylalanine | Phe | F | TTC | TTT | | | |
| Glycine | Gly | G | GGA | GGC | GGG | GGT | |
| Histidine | His | H | CAC | CAT | | | |
| Isoleucine | Ile | I | ATA | ATC | ATT | | |
| Lysine | Lys | K | AAA | AAG | | | |
| Leucine | Leu | L | TTA | TTG | CTA | CTC | CTG | CTT |
| Methionine | Met | M | ATG | | | | |
| Asparagine | Asn | N | AAC | AAT | | | |
| Proline | Pro | P | CCA | CCC | CCG | CCT | |
| Glutamine | Gln | Q | CAA | CAG | | | |
| Arginine | Arg | R | AGA | AGG | CGA | CGC | CGG | CGT |
| Serine | Ser | S | AGC | AGT | TCA | TCC | TCG | TCT |
| Threonine | Thr | T | ACA | ACC | ACG | ACT | |
| Valine | Val | V | GTA | GTC | GTG | GTT | |
| Tryptophan | Trp | W | TGG | | | | |
| Tyrosine | Tyr | Y | TAC | TAT | | | |

Sequence alterations that do not change the amino acid sequence encoded by the polynucleotide are termed "silent" variations. With the exception of the codons ATG and TGG, encoding methionine and tryptophan, respectively, any of the possible codons for the same amino acid can be substituted by a variety of techniques, e.g., site-directed mutagenesis, available in the art. Accordingly, any and all such variations of a sequence selected from the above table are a feature of the instant disclosure.

In addition to silent variations, other conservative variations that alter one, or a few amino acids in the encoded polypeptide, can be made without altering the function of the polypeptide, these conservative variants are, likewise, a feature of the instant disclosure.

For example, substitutions, deletions and insertions introduced into the sequences provided in the Sequence Listing are also envisioned by the instant disclosure. Such sequence modifications can be engineered into a sequence by site-directed mutagenesis (Wu (ed.) Meth. Enzymol. (1993) vol. 217, Academic Press) or the other methods noted below Amino acid substitutions are typically of single residues; insertions usually will be on the order of about from 1 to 10 amino acid residues; and deletions will range about from 1 to 30 residues. In preferred embodiments, deletions or insertions are made in adjacent pairs, e.g., a deletion of two residues or insertion of two residues. Substitutions, deletions, insertions or any combination thereof can be combined to arrive at a sequence. The mutations that are made in the polynucleotide encoding the transcription factor should not place the sequence out of reading frame and should not create complementary regions that could produce secondary mRNA structure. Preferably, the polypeptide encoded by the DNA performs the desired function.

Conservative substitutions are those in which at least one residue in the amino acid sequence has been removed and a different residue inserted in its place. Such substitutions generally are made in accordance with the Table 12 when it is desired to maintain the activity of the protein. Table 12 shows amino acids which can be substituted for an amino acid in a protein and which are typically regarded as conservative substitutions.

TABLE 12

Possible conservative amino acid substitutions

| Residue | Conservative Substitutions |
|---|---|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

The polypeptides provided in the Sequence Listing have a novel activity, such as, for example, regulatory activity.

Although all conservative amino acid substitutions (for example, one basic amino acid substituted for another basic amino acid) in a polypeptide will not necessarily result in the polypeptide retaining its activity, it is expected that many of these conservative mutations would result in the polypeptide retaining its activity. Most mutations, conservative or non-conservative, made to a protein but outside of a conserved domain required for function and protein activity will not affect the activity of the protein to any great extent.

Similar substitutions are those in which at least one residue in the amino acid sequence has been removed and a different residue inserted in its place. Such substitutions generally are made in accordance with the Table 13 when it is desired to maintain the activity of the protein. Table 13 shows amino acids which can be substituted for an amino acid in a protein and which are typically regarded as structural and functional substitutions. For example, a residue in column 1 of Table 13 may be substituted with residue in column 2; in addition, a residue in column 2 of Table 13 may be substituted with the residue of column 1.

TABLE 13

Similar amino acid substitutions

| Residue | Similar Substitutions |
|---------|----------------------|
| Ala | Ser; Thr; Gly; Val; Leu; Ile |
| Arg | Lys; His; Gly |
| Asn | Gln; His; Gly; Ser; Thr |
| Asp | Glu, Ser; Thr |
| Gln | Asn; Ala |
| Cys | Ser; Gly |
| Glu | Asp |
| Gly | Pro; Arg |
| His | Asn; Gln; Tyr; Phe; Lys; Arg |
| Ile | Ala; Leu; Val; Gly; Met |
| Leu | Ala; Ile; Val; Gly; Met |
| Lys | Arg; His; Gln; Gly; Pro |
| Met | Leu; Ile; Phe |
| Phe | Met; Leu; Tyr; Trp; His; Val; Ala |
| Ser | Thr; Gly; Asp; Ala; Val; Ile; His |
| Thr | Ser; Val; Ala; Gly |
| Trp | Tyr; Phe; His |
| Tyr | Trp; Phe; His |
| Val | Ala; Ile; Leu; Gly; Thr; Ser; Glu |

The polypeptides provided in the Sequence Listing have a novel activity, such as, for example, regulatory activity. Although all conservative amino acid substitutions (for example, one basic amino acid substituted for another basic amino acid) in a polypeptide will not necessarily result in the polypeptide retaining its activity, it is expected that many of these conservative mutations would result in the polypeptide retaining its activity. Most mutations, conservative or non-conservative, made to a protein but outside of a conserved domain required for function and protein activity will not affect the activity of the protein to any great extent.

Substitutions that are less conservative than those in Table 12 can be selected by picking residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

Plant Species

In accordance with the instant disclosure, the present method produces a transgenic plant having, for example, increased growth compared to its wild type plant from which it is derived. In one embodiment of the present instant disclosure, the transgenic plant is a perennial plant, i.e. a plant that lives for more than two years. In a specific embodiment, the perennial plant is a woody plant which may be defined as a vascular plant that has a stem (or more than one stem) which is lignified to a high degree.

In a preferred embodiment, the woody plant is a hardwood plant, i.e. broad-leaved or angiosperm trees, which may be selected from the group consisting of acacia, *eucalyptus*, hornbeam, beech, mahogany, walnut, oak, ash, willow, hickory, birch, chestnut, poplar, alder, maple, sycamore, ginkgo, and sweet gum. Hardwood plants from the Salicaceae family, such as willow, poplar and aspen, including variants thereof, are of particular interest, as these two groups include fast-growing species of tree or woody shrub which are grown specifically to provide timber and bio-fuel for heating. Cellulosic grasses used for bioenergy such as switchgrass, *Miscanthus*, and red canary grass are also of interest.

In further embodiments, the woody plant is softwood or a conifer which may be selected from the group consisting of cypress, Douglas fir, fir, *sequoia*, hemlock, cedar, juniper, larch, pine, redwood, spruce and yew.

In another embodiment, the woody plant is a fruit bearing plant which may be selected from the group consisting of apple, plum, pear, banana, orange, kiwi, lemon, cherry, grapevine and fig.

Other woody plants which may be useful in the present instant disclosure may also be selected from the group consisting of cotton, bamboo and rubber plants.

EXAMPLES

It is to be understood that this disclosure is not limited to the particular devices, machines, materials and methods described. Although particular embodiments are described, equivalent embodiments may be used to practice the claims.

The instant sequences plants and methods, now being generally described, will be more readily understood by reference to the following examples, which are included merely for purposes of illustration of certain aspects and embodiments of the present disclosure and are not intended to limit the claims. It will be recognized by one of skill in the art that a transcription factor that is associated with a particular first trait may also be associated with at least one other, unrelated and inherent second trait which was not predicted by the first trait.

Example I. Project Types

A variety of constructs were used to modulate the activity of transcription factors, and to test the activity of orthologs and paralogs in transgenic plant material, such as *Arabidopsis*, tomato and Poplar. Transgenic lines from each particular transformation "project" were examined for morphological and physiological phenotypes. An individual project was defined as the analysis of a set of lines for a particular construct or knockout.

Overexpression/Tissue-Enhanced/Conditional Expression

The promoters used in our experiments were selected in order to provide for a range of different expression patterns. Details of promoters being used are provided in Example II.

Expression of a given TF from a particular promoter was achieved either by a direct-promoter fusion construct in which that TF was cloned directly behind the promoter of interest or by a two component system. Both direct promoter fusions and the two-component system were used in *Arabidopsis*. In tomato, analysis was carried out entirely with the two-component system. In poplar, direct promoter fusions were used for analysis. Details of transformation vectors used in these studies are shown in the Vector and Cloning Information (Example III)

The Two-Component Expression System

For the two-component system, two separate constructs were used: Promoten:LexA-GAL4TA and opLexA::TF. The first of these (Promoten:LexA-GAL4TA) comprised a desired promoter cloned in front of a LexA DNA binding domain fused to a GAL4 activation domain. The construct vector backbone (pMEN48, also known as P5375) also carried a kanamycin resistance marker, along with an opLexA::GFP (green fluorescent protein) reporter. Transgenic lines were obtained containing this first component, and a line was selected that shows reproducible expression of the reporter gene in the desired pattern through a number of generations. A homozygous population was established for that line, and the population was supertransformed (or crossed, in tomato) with the second construct (opLexA::TF) carrying the TF of interest cloned behind a LexA operator site. This second construct vector backbone (pMEN53, also known as P5381) also contained a sulfonamide resistance marker. To demonstrate that each of the promoter driver lines could generate the desired expression pattern of a second component target at an independent locus arranged in trans, crosses were made to an opLexA::GUS line. Typically, it was confirmed that the progeny exhibited GUS activity in an equivalent region to the GFP seen in the parental promoter driver line. However, GFP can move from cell-to-cell early in development and in meristematic tissues, and hence patterns of GFP in these tissues do not strictly report gene expression.

Direct Fusion Constructs

The vector backbone for most of the direct promoter-fusion overexpression constructs for analysis in *Arabidopsis* was pMEN65, but pMEN1963 and pMEN20 were sometimes used. The vectors used for overexpression analysis in poplar are pK2GW7 (Karimi, M. et al. (2002)), for 35S promoter driven overexpression and pPCV812-LMP1-GW for LMP1 promoter driven overexpression.

Example II. Promoter Analysis

Transgene expression was regulated by using a panel of different promoters via direct promoter fusions or via a two-component system as described above.

Promoters used in driver lines or in direct fusion constructs are shown in Table 14.

TABLE 14

Expression patterns conferred by promoters used for one (i.e., in some 35S overexpressing lines and pLMP1 lines) and two-component studies.

| Promoter | Expression pattern conferred | Reference |
|---|---|---|
| 35S | Constitutive, high levels of expression in all throughout the plant and fruit | Odell et al. (1985) |
| AS1 | Primordia and young organs; expressed predominately in differentiating tissues. In fruit, most strongly expressed in vascular tissues and in endosperm | Byrne et al. (2000) |
| LMP1 | General expression pattern, highest expression levels in vascular cambium, and just outside the apical meristems. | US patent publication 20070180580 |
| LTP1 | Shoot epidermal/trichome enhanced; in vegetative tissues, expression is predominately in the epidermis. Low levels of expression are also evident in vascular tissue. In the fruit, expression is strongest in the pith-like columella/placental tissue | Thoma et al. (1994) |
| PD | Phytoene desaturase; moderate expression in fruit tissues | Corona et al. (1996) |
| AP1 | Flower primordia/flower; light expression in leaves increases with maturation. Highest expression in flower primordia and flower organs. In fruits, predominately in pith-like columella/placental tissue | Hempel et al. (1997); Mandel et al. (1992) |

Example III. Cloning Information

Cloning Methods

*Arabidopsis* transcription factor clones were created in one of three ways: isolation from a library, amplification from cDNA, or amplification from genomic DNA. The ends of the *Arabidopsis* transcription factor coding sequences were generally confirmed by RACE PCR or by comparison with public cDNA sequences before cloning.

Clones of transcription factor orthologs of the disclosed sequences can be made by amplification from cDNA. Such orthologs can be derived from plants species, including but not limited to: crops, such as rice, maize, and soybean; and woody plants, such as acacia, *eucalyptus*, hornbeam, beech, mahogany, walnut, oak, ash, willow, hickory, birch, chestnut, poplar, alder, maple, sycamore, ginkgo, palm, and sweet gum. willow, poplar, aspen, cypress, Douglas fir, fir, *sequoia*, hemlock, cedar, juniper, larch, pine, redwood, spruce and yew; cellulosic grasses used for bioenergy such as switchgrass, *Miscanthus*, and red canary grass; and fruit-bearing plants such as apple, plum, pear, banana, orange, kiwi, lemon, cherry, grapevine and fig. The ends of the coding sequences can be predicted based on homology to *Arabidopsis* or by comparison to public and proprietary cDNA sequences. For cDNA amplification, KOD Hot Start DNA Polymerase (Novagen, Madison, Wis.) is used in combination with 1M betaine and 3% DMSO. This protocol was found to be successful in amplifying cDNA from GC-rich species such as rice and corn, along with some non-GC-rich species such as soybean and tomato, where traditional PCR protocols failed. Primers are designed using at least 30 bases specific to the target sequence, and were designed close to, or overlapping, the start and stop codons of the predicted coding sequence.

Clones are fully sequenced. In the case of rice, high-quality public genomic sequences are available for comparison, and clones with sequence changes that result in changes in amino acid sequence of the encoded protein are rejected. For corn and soy, however, it can be unclear whether sequence differences represent an error or polymorphism in the source sequence or a PCR error in the clone. Therefore, in the cases where the sequence of the clone we obtained differed from the source sequence, a second clone is created from an independent PCR reaction. If the sequences of the two clones agreed, then the clone is accepted as a legitimate sequence variant.

Example IV. Transformation

Transformation of *Arabidopsis*

The methods for transformation of *Arabidopsis* may be found in US patent publication 2009-0138981-A1, Example IV. The entire content of this publication is herein incorporated by reference.
Transformation of Tomato
The methods for transformation of tomato may be found in US patent publication 2009-0205063 A1, Example IV. The entire content of this publication is herein incorporated by reference.
Transformation of Poplar
CaMV 35S: over-expression DNA constructs were transformed into *Agrobacterium* and subsequently into Hybrid aspen, where *Populus tremula* L.x*P. tremuloides* Minch clone T89, hereafter called "poplar", was transformed and regenerated essentially as described in Nilsson et al. (1992). Approximately 3-8 independent lines were generated for each construct. One such group of transgenic trees produced using one construct is hereafter called a "construct group", e.g. different transgenic trees emanating from one construct.

Each transgenic line within each construct group, hereafter referred to as a "construct group line", e.g. M124-1B, M124-3A, and so on, are different transformation events and therefore most probably have the recombinant DNA inserted into different locations in the plant genome. This makes the different lines within one construct group partly different. For example it is known that different transformation events will produce plants with different levels of gene over expression.

Example V. *Arabidopsis* Morphology Experimental Methods

*Arabidopsis* is used as a model plant for the study of plant growth and development. In addition to providing ornamental utility, altered morphological or developmental features may affect stress tolerance and ultimately plant quality or yield. For example, alterations to appendages such as hairs and trichomes, stomata, and the deposition of waxes may enhance a plant's ability to take up nutrients or resist disease or pathogens. Genes or their equivalogs that confer late flowering when overexpressed might be used to manipulate the flowering time of commercial species, in particular, an extension of vegetative growth or an increase in leaf size can significantly increase biomass and result in substantial yield increases. Dark color may also contribute to oxidative stress tolerance or enhanced photosynthetic capacity, which in turn could result in yield increases.

Thus, morphological analysis was performed to determine whether changes in transcription factor levels affect plant growth and development. This was primarily carried out on the T1 generation, when at least 10-20 independent lines were examined. However, in cases where a phenotype required confirmation or detailed characterization, plants from subsequent generations were also analyzed.

The methods for morphological analysis of *Arabidopsis* are described in Example V of US patent publication US20090138981-A1, which is herein incorporated by reference.

Example VI. *Arabidopsis* Physiology Experimental Methods

*Arabidopsis* transformants were evaluated for their performance under various biotic and abiotic stress conditions in plate-based and/or soil-based assays. The methods for physiological analysis of *Arabidopsis* are described in Examples VI-XI of US patent publication US20090138981A1, which are herein incorporated by reference.

Transgenic plants overexpressing some of polypeptides of the invention, for example, G189 (SEQ ID NO: 175) were subjected to C/N sensing studies and showed positive results. These assays were intended to find genes that allowed more plant growth upon deprivation of nitrogen, or which modulate plant metabolism to adjust to changes in sugar levels and regulate carbon flux into different types of organic molecules within the plant. Indeed, recent data of Lam et al. (2003) showed that a C/N assay could be used identify genes that produce improvements in seed nutrient content. Nitrogen is a major nutrient affecting plant growth and development that ultimately impacts yield and stress tolerance. The C/N assays monitored growth and the appearance of stress symptoms such as anthocyanins or media with high sugar levels or which is nitrogen deficient. In all higher plants, inorganic nitrogen is first assimilated into glutamate, glutamine, aspartate and asparagine, the four amino acids used to transport assimilated nitrogen from sources (e.g. leaves) to sinks (e.g. developing seeds). This process is regulated by light, as well as by C/N metabolic status of the plant. A C/N sensing assay was thus used to look for alterations in the mechanisms plants use to sense internal levels of carbon and nitrogen metabolites which could activate signal transduction cascades that regulate the transcription of nitrogen-assimilatory genes. To determine whether these mechanisms are altered, we exploited the observation that wild-type plants grown on media containing high levels of sucrose (3%) without a nitrogen source accumulate high levels of anthocyanins. This sucrose induced anthocyanin accumulation can be relieved by the addition of either inorganic or organic nitrogen. For these N additions we used glutamine (1 mM) as a nitrogen source since it also serves as a compound used to transport nitrogen in plants. A positive result was obtained when seedlings of the transgenic overexpression line showed visibly more vigor and/or lower levels of stress-induced compounds (such as anthocyanins) in a C/N assay, relative to controls which lacked the transgene. A C/N sensing assay media refers to a media that is nitrogen deficient and contains high sugar levels. A high sugar level refers to the level that is more than what is typically present in the normal growth media, for example, more than 1%, typically about 3% sucrose (weight/volume percentage) or its equivalent. A nitrogen deficient media refers to a media that contains a nitrogen content that is less than what is typically present in the normal growth media.

Example VII. *Arabidopsis* Soil Drought Assay (Clay Pot)

The soil drought assay (performed in clay pots) was based on that described by Haake et al. (2002). The methods for this analysis may be found in US patent publication US20090138981A1, Example VII, which is herein incorporated by reference.

Example VIII. Morphological and Biochemical Analysis of Tomato Plants

The methods for these analyses may be found in US patent publication US20090205063A1, Example V, which is herein incorporated by reference.

Example IX. Poplar Experimental Methods

Gene Overexpression Level Analysis

Real-time RT PCR was used to compare construct gene expression levels of the recombinant over-expression construct group lines. The expression level of 26S proteasome regulatory subunit S2 was used as a reference to which construct gene expression was normalized. The comparative CT method was used for calculation of relative construct gene expression levels, where the ratio between construction and reference gene expression levels is described by $(1+E_{target})-CT_{target}/(1+E_{reference})-CT_{reference}$ where $E_{target}$ and $E_{reference}$ are the efficiencies of construct and reference gene PCR amplification respectively and $CT_{target}$ and $CT_{reference}$ are the threshold cycles as calculated for construct and reference gene amplification respectively.

For total RNA extraction, leaf tissue samples (approx. 50 mg) were harvested from tissue culture plants and flash frozen in liquid nitrogen. For each construct group, sampling was performed on all transgenic construct group lines generated by *Agrobacterium* mediated transformation as well as on a number of wild type tissue culture plants. Frozen samples were ground in a bead mill (Retsch MM301). Total RNA was extracted using E-Z 96 Plant RNA kit according to manufacturer's recommendations (Omega Bio-Tek). cDNA synthesis was performed using qScript cDNA synthesis kit according to manufacturer's recommendations (Quanta BioSciences). RNA concentrations were measured and equal amounts were used for cDNA synthesis to ensure equal amounts of cDNA for PCR reactions. The cDNA was diluted 12.5× prior to real-time PCR.

Real-time PCR primers were designed using Beacon Designer 6 (PREMIER Biosoft International) using included tool to minimize interference of template secondary structure at primer annealing sites.

For real-time PCR, cDNA template was mixed with corresponding construct gene specific primers, internal reference gene specific primers) and PerfeCTa SYBR Green SuperMix (Quanta BioSciences). Real-time PCR reactions were run on a MyiQ PCR thermocycler (Bio-Rad) and analysed using included software iQ5. Reactions were set up in triplicates, three times using construct gene specific primers and three times using reference gene specific primers for each sample, and the average threshold cycle for each triplicate was subsequently used for calculation of relative construct gene expression levels. Real-time PCR reactions on cDNA template from wild type material were used as negative experimental controls, as the *Arabidopsis* gene constructs inserted in transgenic poplar plants are not natively expressed in wild type plants.

The 96 well plate was covered with microfilm and set in the thermocycler to start the reaction cycle. By way of illustration, the reaction cycle may include the following steps: Initial denaturation at 95° C. for 3 minutes 30 seconds followed by 40 rounds of amplification comprising the following steps 95° C. for 10 seconds, 55° C. for 30 seconds and 72° C. for 40 seconds.

Based on gene overexpression level analysis, three construct group lines per construct group were selected for a first round of greenhouse planting. Construct group lines were deliberately selected so that different levels of gene overexpression were represented, since it is known that the level of gene overexpression may influence the phenotypical response. Therefore, one construct group line was selected to have a relatively high gene overexpression level, another a medium gene overexpression level and yet another a relatively low gene overexpression level.

Poplar Plant Growth Setup

Generally three replicate plants of each construct group line were planted in the greenhouse. Genetically identical plants were produced by tissue culture propagation of the construct group lines, indicated by a -1, -2 and -3 suffix. Accordingly M124-1B-1, M124-1B-2 and M124-1B-3 are genetically identical replicates of construct group line M124-1B. Genetically identical wild type control plants were propagated and planted similarly. The transgenic poplar lines were grown together with their wild type control (wt) trees, in a greenhouse under a photoperiod of 18 h and a temperature of 22° C./15° C. (day/night). The pot size was 3 liters. The plants were fertilized weekly with Weibulls Rika S NPK 7-1-5 diluted 1 to 100 (final concentrations NO3, 55 g/l; NH4, 29 g/l; P, 12 g/l; K, 56 g/l; Mg 7.2 g/l; S, 7.2 g/l; B, 0.18 g/l; Cu, 0.02 g/l; Fe, 0.84 g/l; Mn, 0.42 g/l; Mo, 0.03 g/l; Zn, 0.13 g/L). The plants were grown for 8-9 weeks before sampling and harvesting. During this time their height and diameter was measured one to two times per week. In a growth group a number of wild type trees (typically 35-45 trees) and a number of transgenic trees comprising several construct groups (typically 6-20 construct groups) were grown in parallel in the greenhouse under the same above conditions. All comparisons between the wild type trees and construct groups were made within each growth group.

Poplar Plant Sampling

Two principal types of harvests and samplings were performed at the end of the greenhouse growth period. One general type was designed for chemical analysis, wood morphology analysis, gene expression analysis, wood density analysis and metabolomics analysis. The second type was designed for dry weight measurements of bark, wood, leaves and roots and Specific leaf area analysis (SLA).

Replanting and Regrowth

Based on growth data analysis from the first round of greenhouse growth, construct groups were propagated in tissue culture, replanted and regrown in the greenhouse. When replanting a construct group, two more construct group lines were generated and planted. The suffix rp indicates a re-planting of the construct group plants after tissue culture propagation, where rp1 denotes the first re-planting, rp2 the second re-planting and so on. Accordingly, construct groups named for example M124rp1 with individuals such as M124rp1-1B, refers to the exact same plants as plants from construct group M124 not having the rp1 suffix. A plant named M124rp1-1B is hence the first re-planting of construct group line originally planted as M124-1B.

Based on growth data, a number of analyses and growth rate factors were performed and calculated in order to select the construct groups and thereby the genes which can be used to alter growth characteristics. Selection criteria and methods were as described below.

Example X. Physiological Analysis of Poplar Plants

Drought Tolerance Assay and WUE

The water use efficiency of poplar plants included in the drought tolerance assay was evaluated by sampling two fresh sun leaves before starting the drought stress. The leaves were subsequently dried and ground before analyzing the $^{13}C/^{12}C$ ratio of the bulk leaf material. Expression of the bulk leaf $^{13}C/^{12}C$ ratio relative to the Vienna Pee Dee Belemnite standard (V-PDB), using $^{13}C$ terminology (Farquhar et al. (1989) provides a surrogate measure of water-use efficiency integrated over the life of the unstressed leaf (Farquhar and Richards 1984).

The drought tolerance assay was performed on poplar plants grown in the greenhouse for 5-6 weeks. The soil in the poplar plant pots was saturated with water at the start of the assay, giving the plants included the same initial water supply. Thereafter no water was given to the plants before they reached stress level 3. Plant soil moisture levels, total plant weights (pot included), plant heights and stress levels were recorded two to three times a day until all or almost all plants had reached stress level 3. When a plant reached stress level 3 (wilting), the water content of the soil was measured and the time from the start of water withholding to reaching stress level 3 was recorded. The stress levels of the assay were:

Stress level 1: some of the leaves of the plant point downwards.
Stress level 2: all the leaves of the plant point downwards.
Stress level 3: the apex of the plant droops (wilting).
Stress level 4: the apex of the plant is dead.

Time to wilting and soil moisture content at wilting were used to evaluate drought stress tolerance. A two tailed t-test assuming equal variance for the construct group and the wild type group was used to detect differences between means for each measured variable. A p-value<0.05 was seen as a significant change in stress tolerance for the construct group.

Hyperosmotic Stress Assay

Poplar plants included in the hyperosmotic stress assay were grown in the greenhouse for approximately 21 days to an approximate height of 25 cm. They were then treated with 0.5 liter of 100 mM salt solution every day for 4 consecutive days, during which time no additional water or fertilizer was supplied. Thereafter the plants were watered and fertilized as normal and plant height growth was measured and recorded during the remainder of the greenhouse growth period of 8-9 weeks in total. Plants with reduced growth impairment under the salt stress, compared to wt control plants, were scored as having increased salt tolerance.

Cold Stress Assay

The cold stress assay was performed on poplar plants grown in the greenhouse for 3-5 weeks. The soil in the poplar plant pots was saturated with water at the start of the assay, giving the plants the same initial water supply. After 3-5 weeks the plants were taken from the greenhouse and acclimatized to room temperature for about one hour. The plants were then transferred to, and kept in, a climate chamber at 10° C. for 3.5 hours. The light intensity inside the chamber was reduced and the temperature was gradually lowered until it reached −5° C. The temperature in the chamber was held at −5° C. for two hours and then gradually raised together with the light intensity over the course of four hours. At the end of the treatment, plants were returned to room temperature and visually inspected for damage before they were returned to the greenhouse.

Example XI. Morphological and Developmental Analysis of Poplar Plants

Growth Measurements

Plants were grown in the greenhouse for 8-9 weeks, during which time measurements of plant growth (height and diameter) were taken. Data was collected and analyzed for diameter growth rate, maximum height growth rate and final height and diameter as described below.

Growth Analysis: Maximum Height Growth Rate

A height growth rate measure (here named "Maximum height growth rate") was defined as the slope of a linear function fitted over four consecutive height data points. A height growth rate value was calculated for data point 1-4, data point 2-5 etc. in a step-wise manner, see FIG. 1 for an example. A maximum height growth rate defined as the maximum value produced from step-wise linear regression analysis for each plant was computed. The rate at which the height of the plants increases has distinct phases, increasing during the first part of growth to a maximum then declining as the plants become larger. Because these phases occur at different times in different plants, and because these measurements are inherently quite noisy, this method of determining the Maximum height growth rate gives the most accurate results for the different individual trees.

Growth Analysis: Stem Diameter Growth Rate

Under the above defined growth conditions, stem diameter (d), measured 10 cm up the stem from the soil, exhibited a comparatively linear increase over time (t) described by the formula $d(t)=c*t+d0$, where $d0$ is the initial stem diameter and c the rate of increase in diameter (slope). A linear regression fitted to increases in stem diameter over time was used for estimating c.

Growth Analysis: Final Height and Final Stem Diameter

The final height and diameter measured at the end of the 8 to 9 week assay were also used to select construct groups with altered growth characteristics. These values reflect both the tree's growth capacity and the tree's ability to start growing when transferred from tissue culture into soil and placed in a greenhouse.

Growth Parameters

Construct groups that showed increases, compared to the wild type population, in the above mentioned growth parameters, i.e. stem diameter growth rate, maximum height growth rate, final height and final stem diameter, were identified as construct groups that have altered (growth properties. Therefore, the corresponding genes can be used to alter these properties. The selection criteria defining growth increase are stated below. Two different selection criteria levels were used, a basic level defining a changed growth phenotype and a more stringent level for constructs defining growth phenotypes of extra interest.

Growth Difference Selection Criteria

Abbreviations used for the different growth parameters when used to describe construct group phenotypes:

TABLE 15

Abbreviations of the growth parameters used in this application

| Abbreviation | Description of the Abbreviation |
|---|---|
| AFH | Average final height of the wild type population and each construct group population |

TABLE 15-continued

Abbreviations of the growth parameters used in this application

| Abbreviation | Description of the Abbreviation |
|---|---|
| AFD | Average final stem diameter of the wild type population and each construct group population |
| AMHGR | Average maximum height growth rate of the wild type population and each construct group population |
| ADGR | Average stem diameter growth rate of the wild type population and each construct group population |
| MFH | final height of the tallest plant from the wild type population and each construct group population |
| MFD | final stem diameter of the widest plant in the wild type population and each construct group population |
| MMHGR | Maximum of Maximum height growth rate of the wild type population and each construct group population |
| MDC | Maximum stem diameter growth rate of the wild type population and each construct group population |

The growth difference selection criteria are as follows:
1. If the construct group AFH, MFH, AMHGR and MMHGR are at least 5% (or 10% in a second more stringent level) greater than corresponding wild type group AFH, MFH, AMHGR and MMHGR, or
2. If the construct group AFD, MFD, ADGR and MDC are at least 5% (or 10% in a second more stringent level) greater than corresponding wild type group AFD, MFD, ADGR and MDC, or
3. If the construct group AFH, AFD, AMHGR or ADGR is at least 18% (or 25% in the second more stringent level) greater than corresponding wild type group AFH, AFD, AMHGR or ADGR, or
4. If construct group MFH, MFD, MMHGR or MDC is at least 18% (or 25% in the second more stringent level) greater than corresponding wild type group MFH, MFD, MMHGR or MDC.

Construct groups meeting one or more of these criteria were selected.

Statistical analysis on growth parameter were performed using t-test. Samples for each construct were compared with wild type samples (T89) from the same cultivation round. A two-tailed t-test assuming equal variance for the construct group and the wild type group was used to detect differences. A difference was considered significantly changed at a p-value <0.01. This was also done on line level if at least three replicates were measured for a parameter.

To detect individuals with deviating growth parameters a 95% confidence interval was calculated around the wild type population. The confidence interval was set to Average.sub.T89+/−T.sub.crit*Standard deviation.sub.T89, where T.sub.crit used is the two tailed (alpha=0.05). If two or more individuals are outside this confidence interval (on the same side) the density is considered significantly changed.

Dry Weight, Leaf Area and Internode Length Measurements

Plants were harvested at the end of the experiment for a series of destructive analyses. Five fully developed leaves, stem, bark and remaining leaves were collected as separate samples. The total leaf area of the five fully developed leaves was measured and the total length of 20 consecutive, fully developed, internodes was measured. The separate samples of plant material were put in a drier oven for more than 48 hours and dried to constant weight. The dry weights were measured and analysed for differences compared to corresponding wild type groups. Ratios were produced between the transgenic plants and the wt controls.

An evaluation of dry weight properties based on dry weight data was performed. The values are based on the calculated values of construct group averages and construct group line averages as well as the visual analysis of graphs and plots. If the construct group has an overall change in dry weight properties compared to wild type or if at least one of the construct group lines has changed dry weight properties compared to wild type, then the constructs were scored as having increased biomass and growth. The ratios between construct groups and wild-type controls are presented in %, e.g. 100 means the same as wild-type and 145 means 45% higher than wild-type controls. The same value table is used for evaluating differences in leaf area, specific leaf area (SLA, i.e., a measure of leaf thickness, calculated by dividing the area of a portion of a leaf by the dry weight of that same portion of leaf) and internode length.

For each variable (dry weight Wood, dry weight Bark, dry weight "Total:Wood+Bark", dry weight "5 fully developed leaves", dry weight "Remaining leaves", dry weight "Total:Leaves", dry weight "Total:Shoot", "Leaf area", "Specific Leaf Area", "Internode Length", dry weight "Root", dry weight "Total:Shoot+root" and ratio "Root/Shoot") the construct group average is compared with corresponding wild type group using a two sided t-test assuming equal variance for the construct group and the wild type group.

To detect construct group lines with deviating Wood dry weight, Bark dry weight, "Total:Wood+Bark" dry weight, "5 fully developed leaves" dry weight, "Remaining leaves" dry weight, "Total:Leaves" dry weight, "Total:Shoot" dry weight, "Leaf area", "Specific Leaf Area", "Internode Length", "Root" dry weight, "Total:Shoot+root" dry weight or "Root/Shoot" ratio, 95% confidence intervals were calculated around the wild type population for each variable. The confidence interval was set to Average.sub.T89+/−T.sub.crit*Standard deviation.sub.T89, where T.sub.crit used is the two tailed (alpha=0.05). If the construct group line average is outside this confidence interval, the variable is considered significantly changed for that construct group line.

Density Measurement

A 5 cm-long stem section (the segment between 36 cm and 41 cm from the soil) of each plant was stored in a freezer (−20° C.) after harvest. Samples subjected to density measurement were first defrosted and debarked and then the central core was removed. The weight (w) was measured using a balance and the volume (v) was determined using the principle of Archimedes: the wood samples were pushed (using a needle) into a beaker (placed on a balance) with water. The increase in weight (which equals the weight of the wood plus the force used to submerge it) is equivalent to weight of the water displaced by the wood sample, and since the density of water is (1 g/cm.sup.3) it is equivalent to the volume of the wood samples. The samples were then dried in an oven for >48 h at 45° C. The dry weight (dw) was measured and the density (d) was calculated according to (1).

$$d = dw/v \qquad (1)$$

Samples for each construct were compared with wild type samples (T89) from the same cultivation round. A two-tailed t-test assuming equal variance for the construct group and the wild type group was used to detect differences on average density. The density was considered significantly changed at a p-value <0.01.

To detect individuals with deviating density a 95% confidence interval was calculated around the wild type population. The confidence interval was set to Average.sub.T89+/−T.sub.crit*Standard deviation.sub.T89, where T.sub.crit used is the two tailed (alpha=0.05). If two or more individuals are outside this confidence interval (on the same side) the density is considered significantly changed.

Example XI. Experimental Results

This application provides experimental observations for a number of transcription factors for improved yield and/or growth enhancement and/or increased tolerance to abiotic stresses such as water deficit-related tolerance, low nutrient tolerance, and cold tolerance. These transcription factors include G2379, G1730, G189, G2142, G2552, G2724, G287, G748, and G878 (SEQ ID NO: 298, 120, 175, 226, 330, 400, 436, 514, and 606, respectively).

In this Example, unless otherwise indicated, morphological and physiological traits are disclosed in comparison to wild-type control plants. That is, a transformed plant that is described as large and/or drought tolerant is large and more tolerant to drought with respect to a wild-type control plant. When a plant is said to have a better performance than controls, it generally showed less stress symptoms than control plants. The better performing lines may, for example, produce less anthocyanin, or be larger, green, or more vigorous in response to a particular stress, as noted below. Better performance generally implies greater tolerance to a particular biotic or abiotic stress, less sensitivity to ABA, or better recovery from a stress (as in the case of a drought treatment) than controls.

Overexpression constructs were introduced into *Arabidopsis*, poplar and tomato and morphological and physiological tests were performed on established transgenic lines. Table 16 summarizes experimental results with plants in which disclosed sequences have been overexpressed. These modifications have yielded new and potentially valuable phenotypic traits, relative to control plants, in morphological, physiological or disease assays, as demonstrated in *Arabidopsis*, in poplar or in tomato (the last column). The fourth and fifth column list the trait category and trait details that were observed in plants, relative to control plants, after transforming plants with each transcription factor polynucleotide GID (Gene IDentifier, found in the first column) under the listed regulatory control mechanism.

TABLE 16

Phenotypic traits conferred by transcription factors in morphological or physiological assays

| GID | PRT SEQ ID NO: | Promoter | Trait | Trait detail | Species |
|---|---|---|---|---|---|
| G2379 | 298 | 35S | Altered sugar sensing | Increased tolerance to sucrose (e.g., 9.4% sucrose) | *Arabidopsis* |
| G2379 | 298 | 35S | Water deprivation | Reduced $^{13}$C discrimination | Poplar |
| G2379 | 298 | 35S | Water deprivation | Increased time to wilting | Poplar |
| G1730 | 120 | 35S | Osmotic | Increased tolerance to hyperosmotic stress (higher germination efficiency in 300 mM mannitol or 5% glucose ) | *Arabidopsis* |
| G1730 | 120 | 35S | Water deprivation | Soil Drought: Increased tolerance | *Arabidopsis* |
| G1730 | 120 | 35S | Water deprivation | Lower soil water content at wilting | Poplar |
| G1730 | 120 | 35S | Water deprivation | Increased time to wilting | Poplar |
| G1730 | 120 | 35S | Water deprivation | Reduced $^{13}$C discrimination | Poplar |
| G189 | 175 | 35S | Leaf | Size: large leaves | *Arabidopsis* |
| G189 | 175 | 35S | Nutrient uptake | Altered C/N sensing: increased tolerance to low nitrogen medium with high sucrose without a nitrogen source | *Arabidopsis* |
| G189 | 175 | 35S | Increased growth | Increased dry weight | Poplar |
| G189 | 175 | 35S | Increased growth | Increased growth rate | Poplar |
| G189 | 175 | 35S | Increased growth | Increased plant height | Poplar |
| G189 | 175 | 35S | Increased growth | Increased "Specific Leaf Area" | Poplar |
| G189 | 175 | 35S | Increased growth | Decreased "Root/Shoot" ratio | Poplar |
| G189 | 175 | 35S | Density | Increased wood density | Poplar |
| G189 | 175 | 35S | Increased growth | Increased internode length | Poplar |
| G2142 | 226 | 35S | Nutrient uptake | Increased tolerance to phosphate-free medium | *Arabidopsis* |
| G2142 | 226 | 35S | Increased growth | Increased dry weight | Poplar |
| G2142 | 226 | 35S | Increased growth | Increased plant height | Poplar |
| G2142 | 226 | 35S | Increased growth | Increased stem volume | Poplar |
| G2552 | 330 | 35S | Leaf glucosinolates | Increase M39480 | *Arabidopsis* |
| G2552 | 330 | LMP1 | Increased growth | Increased dry weight | Poplar |
| G2552 | 330 | LMP1 | Increased growth | Increased growth rate | Poplar |
| G2552 | 330 | LMP1 | Increased growth | Increased main stem diameter | Poplar |
| G2552 | 330 | LMP1 | Increased growth | Increased "Leaf Area" | Poplar |
| G2552 | 330 | LMP1 | Increased growth | Decreased "Root/Shoot" ratio | Poplar |
| G2552 | 330 | LMP1 | Increased growth | Increased Internode length | Poplar |
| G2552 | 330 | LMP1 | Increased growth | Increased plant height | Poplar |
| G2552 | 330 | AS1 | Size | Increased biomass | Tomato |
| G2724 | 400 | 35S | Leaf | Color: dark green leaves | *Arabidopsis* |
| G2724 | 400 | 35S | Increased growth | Increased dry weight | Poplar |
| G2724 | 400 | 35S | Increased growth | Increased "Leaf Area" | Poplar |
| G2724 | 400 | 35S | Increased growth | Decreased Root/Shoot ratio | Poplar |
| G2724 | 400 | 35S | Increased growth | Increased plant height | Poplar |
| G2724 | 400 | 35S | Increased growth | Increased main stem diameter | Poplar |
| G287 | 436 | 35S | Size | Increased biomass | *Arabidopsis* |
| G287 | 436 | 35S | Increased growth | Increased growth rate | Poplar |
| G287 | 436 | 35S | Increased growth | Increased plant height | Poplar |

TABLE 16-continued

Phenotypic traits conferred by transcription factors in morphological or physiological assays

| GID | PRT SEQ ID NO: | Promoter | Trait | Trait detail | Species |
|---|---|---|---|---|---|
| G287 | 436 | 35S | Increased growth | Increased dry weight | Poplar |
| G748 | 514 | 35S | Flowering time | Late flowering | Arabidopsis |
| G748 | 514 | 35S | Stem | More vascular bundles in stem | Arabidopsis |
| G748 | 514 | 35S | Seed prenyl lipids | Increased seed lutein content | Arabidopsis |
| G748 | 514 | 35S | Increased growth | Increased growth rate | Poplar |
| G748 | 514 | 35S | Increased growth | Increased plant height | Poplar |
| G748 | 514 | 35S | Density | Increased wood density | Poplar |
| G878 | 606 | 35S | Flowering time | Late flowering | Arabidopsis |
| G878 | 606 | 35S | Senescence | Late senescing | Arabidopsis |
| G878 | 606 | 35S | Increased growth | Increased growth rate | Poplar |
| G878 | 606 | 35S | Increased growth | Increased plant height | Poplar |
| G878 | 606 | 35S | Increased growth | Increased Internode length | Poplar |
| G878 | 606 | 35S | Density | Increased wood density | Poplar |

The results showed that overexpression of each of the majority of these *Arabidopsis* transcription factors, being able to bring about desired traits in *Arabidopsis* or tomato, also had notable related effects on poplar, for example, G189 and G287. On the other hand, overexpression of each of others in poplar (as shown in Table 16) have shown to result in novel and valuable traits that have not been observed in *Arabidopsis*. For example, the growth enhancement by overexpression of G878 poplar had not been observed in *Arabidopsis* (as noted in Table 16).

For each of these transcription factors, a number of phylogenetically and closely related homologs derived from these sequences can be analyzed for their function using similar approaches.

Poplar Growth Results

Growth results for the specified construct groups and the corresponding wild type groups are shown in Tables 17 to 57. Table rows contain height and diameter measurements of individuals of specified construct group (named "M") and corresponding wild type group (named "T89"). Time of measurement as number of days in greenhouse is shown in table headers.

Based on growth data analysis from the first round of greenhouse growth, construct groups were propagated in tissue culture, replanted and regrown in the greenhouse. When replanting a construct group, two more construct group lines were generated and planted. The suffix rp indicates a re-planting of the construct group plants after tissue culture propagation, where rp1 denotes the first re-planting, rp2 the second re-planting and so on. Accordingly, construct groups named for example M124rp1 with individuals such as M124rp1-1B, refers to the exact same plants as plants from construct group M124 not having the rp1 suffix. A plant named M124rp1-1B is hence the first re-planting of construct group line originally planted as M124-1B. Unless otherwise noted, the unit for plant height is centimeter (cm), the unit for diameter is millimeter (mm)

Construct Group M049

Construct group M049 corresponds to transgenic poplar plants overexpressing gene G2379 (SEQ ID NO: 297). The $^{13}C$ values shown in Table 17 provide evidence of increased water use efficiency in those individuals with less negative $^{13}C$ (decreased discrimination against $^{13}C$).

TABLE 17

Raw data, $^{13}C$ values

| Individual | $^{13}C$ (per mil) |
|---|---|
| M049-2B-1 | −30.1068 |
| M049-2B-2 | −30.9629 |
| M049-2B-3 | −29.6844 |
| M049-3A-1 | −30.3615 |
| M049-3A-2 | −31.1093 |
| M049-3A-3 | −30.2534 |
| M049-5A-1 | −31.2894 |
| M049-5A-2 | −30.9212 |
| M049-5A-3 | −30.1426 |
| T89-01 | −30.1911 |
| T89-02 | −30.9682 |
| T89-03 | −30.95705 |
| T89-04 | −30.94365 |
| T89-05 | −30.7631 |
| T89-06 | −30.85345* |
| T89-07 | −31.0034 |
| T89-08 | −31.8227 |
| T89-09 | −31.2472 |
| T89-10 | −31.4418 |
| T89-11 | −30.8103 |
| T89-12 | −31.37145 |
| T89-13 | −31.173 |
| T89-14 | −31.15875 |
| T89-15 | −31.3736 |

*Removed from analysis, Outlier (very short plant)

Construct group M049 showed a decreased $^{13}C$ value according to t-test (p=0.010), on average 1.8% lower $^{13}C$ value, indicating increased water use efficiency.

Construct group line M049-2B showed a decreased $^{13}C$ value according to t-test (p=0.008), on average 2.7% lower $^{13}C$ value, indicating increased water use efficiency. In a replant, the line M049rp3-2B again had a statistically significantly improved $^{13}C/^{12}C$-leaf ratio (+2.3%) compared to WT, and the plants showed normal growth and density properties overall.

TABLE 18

Raw data, time to wilting (h)

| Individual | Time to wilting (h) |
|---|---|
| M049-2B-1 | DNW |
| M049-2B-2 | 90 |
| M049-2B-3 | 95 |

TABLE 18-continued

Raw data, time to wilting (h)

| Individual | Time to wilting (h) |
|---|---|
| M049-3A-1 | 90 |
| M049-3A-2 | 66 |
| M049-3A-3 | 66 |
| M049-5A-1 | 73 |
| M049-5A-2 | DNW |
| M049-5A-3 | DNW |
| T89-01 | 90 |
| T89-02 | 66 |
| T89-03 | 46 |
| T89-04 | 66 |
| T89-05 | 66 |
| T89-06 | DNW* |
| T89-07 | 66 |
| T89-08 | 49 |
| T89-09 | 66 |
| T89-10 | 70 |
| T89-11 | 66 |
| T89-12 | 70 |
| T89-13 | 66 |
| T89-14 | 49 |
| T89-15 | 66 |

*Removed from analysis, Outlier (very short plant)
DNW, did not wilt during the experiment.

Construct group M049 had an increased time to wilting according to a t-test (p=0.013), and on average takes 24.1% longer to wilt. Plants that did not wilt were excluded from the calculations, this means that the effect is greater than indicated in the data.

Construct group line M049-2B had an increased time to wilting according to a t-test (p=0.003), and on average took 43.6% longer to wilt. Plants that did not wilt are excluded from the calculations.

Construct group line M049-5B had an increased time to wilting; only one plant wilted during the experiment.

Construct Group M106

Construct group M106 corresponds to transgenic poplar plants overexpressing gene G1730 (SEQ ID NO: 119).

TABLE 19

Moisture content in soil at wilting (%)

| Individual | Moisture content in soil at wilting (%) |
|---|---|
| M106-1A-1 | 16.8 |
| M106-1A-2 | 12.4 |
| M106-1A-2 | 15.6 |
| M106-2A-1 | 15.7 |
| M106-2A-2 | 16.5 |
| M106-2A-3 | 12.1 |
| M106-3A-1 | 13.4 |
| M106-3A-3 | 12.4 |
| M106-3A-3 | DNW |
| T89-26 | DNW |
| T89-27 | 14.1 |
| T89-28 | 15.7 |
| T89-29 | 18.5 |
| T89-30 | 17.0 |
| T89-32 | 16.6 |
| T89-34 | 13.9 |
| T89-35 | 15.9 |
| T89-36 | 17.8 |
| T89-41 | 16.5 |
| T89-42 | 16.8 |
| T89-43 | 14.4 |

TABLE 19-continued

Moisture content in soil at wilting (%)

| Individual | Moisture content in soil at wilting (%) |
|---|---|
| T89-45 | 16.7 |
| T89-46 | 18.1 |
| T89-47 | 16.3 |

DNW: did not wilt during the experiment.

Construct group M106 had a decreased soil moisture content at wilting according to a t-test (p=0.015), on average 11.9% lower moisture in the soil. Plants that did not wilt were excluded from the calculations.

Construct group line M106-3A had a decreased soil moisture content at wilting according to a t-test (p=0.006), on average 20.8% lower moisture in the soil. Plants that did not wilt were excluded from the calculations.

TABLE 20

Time to wilting (h)

| Individual | Time to wilting (h) |
|---|---|
| M106-1A-1 | 113 |
| M106-1A-2 | 165 |
| M106-1A-2 | 165 |
| M106-2A-1 | 89 |
| M106-2A-2 | 97 |
| M106-2A-3 | 165 |
| M106-3A-1 | 113 |
| M106-3A-3 | 165 |
| M106-3A-3 | DNW |
| T89-26 | DNW |
| T89-27 | 113 |
| T89-28 | 89 |
| T89-29 | 70 |
| T89-30 | 97 |
| T89-32 | 141 |
| T89-34 | 97 |
| T89-35 | 89 |
| T89-36 | 89 |
| T89-41 | 70 |
| T89-42 | 97 |
| T89-43 | 97 |
| T89-45 | 89 |
| T89-46 | 89 |
| T89-47 | 70 |

Construct group M106 showed an increased time to wilting according to a t-test (p=0.001), on average 44.6% longer to wilt. Plants that did not wilt were excluded from the calculations.

Construct group line M106-1A showed an increased time to wilting according to a t-test (p=0.001), on average 59.4% longer to wilt. Plants that did not wilt were excluded from the calculations.

Construct group line M106-3A showed an increased time to wilting according to a t-test (p=0.009), on average 50.0% longer to wilt. Plants that did not wilt were excluded from the calculations.

TABLE 21

$^{13}C$ values

| Individual | $^{13}C$ (per mil) |
|---|---|
| −31.7112 | −31.7112 |
| M106-1A-2 | −32.0544 |
| M106-1A-2 | −31.8242 |

TABLE 21-continued $^{13}$C values

| Individual | $^{13}$C (per mil) |
|---|---|
| M106-2A-1 | −32.249 |
| M106-2A-2 | −32.3056 |
| M106-2A-3 | −32.2202 |
| M106-3A-1 | −31.75595 |
| M106-3A-3 | −31.861 |
| M106-3A-3 | −30.5765 |
| T89-26 | −32.3684 |
| T89-27 | −31.8829 |
| T89-28 | −32.7587 |
| T89-29 | −32.1664 |
| T89-30 | −32.3147 |
| T89-32 | −32.5098 |
| T89-34 | −32.6329 |
| T89-35 | −32.3633 |
| T89-36 | −32.5057 |
| T89-41 | −32.15275 |
| T89-42 | −32.6459 |
| T89-43 | −32.0528 |
| −32.1915 | −32.1915 |
| T89-46 | −32.6081 |
| T89-47 | −32.583 |

Construct group M106 had a more negative .sup.13C value according to a t-test (p=0.002), on average by 1.7%, indicating better water use efficiency.

Construct group line M106-1A had a more negative .sup.13C according to a t-test (p=0.004), on average by 1.6%, indicating better water use efficiency.

Construct group line M106-3A had a more negative .sup.13C according to a t-test (p=0.0004), on average by 3.0%, indicating better water use efficiency.

In a replant, line M106rp2-3A again had statistically significantly improved .sup.13C/.sup.12C-leaf ratio (+3.2%) and statistically significantly improved .sup.13C/.sup.12C-stem ratio (+2.6%) compared to WT. This line had normal growth and density properties.

Construct Group M087

Construct group M087 corresponds to transgenic poplar plants overexpressing gene G189 (SEQ ID NO: 174). This construct induced increased growth. The average final height of the construct group was 28% higher than that of the wild type control group. The average maximum height growth rate of the construct group was 29% higher than the average of the wild type control group. The M087 construct group meets the more stringent level of growth difference selection criteria (1), (3) and (4).

Tables 22 and 23 contain growth data for the specified construct group and corresponding wild type group. Table rows contain height and diameter measurements of individuals of the specified construct group and corresponding wild type group. Time of measurement as number of days in greenhouse is shown in table headers.

TABLE 22

Height growth data (cm) for M087

| Individual | 21 | 27 | 34 | 41 | 48 | 51 | 55 |
|---|---|---|---|---|---|---|---|
| M087-2B-1 | 35 | 53 | 91 | 130 | 160 | 176 | 190 |
| M087-2B-2 | 34 | 49 | 80 | 109 | 141 | 154 | 170 |
| M087-2B-3 | 36 | 54 | 86 | 122 | 158 | 176 | 200 |
| M087-3A-1 | 39 | 60 | 96 | 133 | 168 | 180 | 198 |
| M087-3A-2 | 36 | 55 | 90 | 125 | 159 | 176 | 200 |
| M087-3A-3 | 40 | 57 | 93 | 129 | 163 | 181 | 205 |
| M087-6A-1 | 33 | 50 | 81 | 113 | 145 | 157 | 174 |
| M087-6A-2 | 27 | 40 | 68 | 100 | N/A | N/A | N/A |
| M087-6A-3 | 35 | 52 | 82 | 115 | 151 | 167 | 185 |
| T89-19 | 32 | 45 | 70 | 97 | 123 | 134 | 147 |
| T89-20 | 30 | 45 | 66 | 90 | 119 | 130 | 145 |
| T89-21 | 36 | 51 | 77 | 103 | 131 | 142 | 156 |
| T89-22 | 35 | 53 | 80 | 109 | 133 | 145 | 163 |
| T89-23 | 32 | 46 | 71 | 96 | 122 | 133 | 152 |
| T89-24 | 33 | 46 | 67 | 91 | 117 | 128 | 141 |
| T89-25 | 30 | 45 | 65 | 90 | 116 | 129 | 143 |
| T89-26 | 33 | 46 | 70 | 100 | 129 | 140 | 155 |
| T89-27 | 31 | 45 | 71 | 99 | N/A | 141 | 154 |
| T89-28 | 29 | 42 | 65 | 94 | 120 | 131 | 147 |
| T89-29 | 34 | 49 | 75 | 103 | 130 | 143 | 157 |
| T89-30 | 32 | 48 | 72 | 96 | 122 | 132 | 145 |
| T89-31 | 30 | 44 | 65 | 90 | 116 | 125 | 138 |
| T89-32 | 28 | 40 | 59 | 82 | 107 | 118 | 131 |
| T89-33 | 30 | 45 | 72 | 102 | 127 | 138 | 153 |
| T89-34 | 28 | 42 | 67 | 95 | N/A | 131 | 146 |
| T89-35 | 38 | 54 | 81 | 110 | 131 | 148 | 161 |
| T89-36 | 34 | 49 | 77 | 104 | 134 | 147 | 161 |
| T89-37 | 29 | 45 | 70 | 98 | 124 | 135 | 150 |
| T89-38 | 28 | 41 | 61 | 84 | 109 | 119 | 131 |
| T89-39 | 33 | 46 | 65 | 87 | 111 | 121 | 134 |

TABLE 23

Diameter growth data (mm) for M087

| Individual | 34 | 41 | 48 | 55 |
|---|---|---|---|---|
| M087-2B-1 | 4.8 | 6.3 | 7.5 | 9.1 |
| M087-2B-2 | 4.8 | 6.5 | 7.3 | 9.2 |
| M087-2B-3 | 5.1 | 6.3 | 8.3 | 10.3 |
| M087-3A-1 | 6.1 | 6.9 | 8.8 | 10.2 |
| M087-3A-2 | 5.7 | 6.4 | 8.4 | 9.3 |
| M087-3A-3 | 5.5 | 6.6 | 7.8 | 9.5 |
| M087-6A-1 | 5.7 | 5.9 | 7.7 | 8.8 |
| M087-6A-2 | 4.8 | 5.4 | N/A | N/A |
| M087-6A-3 | 4.9 | 6.6 | 7.1 | 9.6 |
| T89-19 | 5.9 | 6.4 | 6.9 | 8.4 |
| T89-20 | 5.4 | 6.5 | 6.9 | 9.0 |
| T89-21 | 5.8 | 7.1 | 8.1 | 9.5 |
| T89-22 | 5.9 | 5.7 | 8.5 | 10.1 |
| T89-23 | 4.9 | 5.9 | 6.8 | 8.8 |
| T89-24 | 5.4 | 6.2 | 7.2 | 8.8 |
| T89-25 | 4.7 | 5.9 | 6.6 | 8.6 |
| T89-26 | 5.7 | 6.5 | 7.8 | 8.5 |
| T89-27 | 5.5 | 6.5 | 8.8 | 9.3 |
| T89-28 | 5.6 | 7.5 | 7.5 | 9.4 |
| T89-29 | 5.1 | 6.2 | 7.7 | 9.7 |
| T89-30 | 6.1 | 6.3 | 7.7 | 8.3 |
| T89-31 | 5.0 | 6.6 | 6.6 | 8.4 |
| T89-32 | 4.8 | 5.8 | 6.0 | 7.2 |
| T89-33 | 5.6 | 6.1 | 7.7 | 9.2 |
| T89-34 | 4.7 | 6.2 | 7.9 | 9.5 |
| T89-35 | 5.6 | 6.6 | 8.2 | 9.3 |
| T89-36 | 5.5 | 6.6 | 8.3 | 11.3 |
| T89-37 | 5.8 | 6.7 | 7.5 | 10.0 |
| T89-38 | 5.2 | 6.4 | 6.5 | 8.1 |
| T89-39 | 5.1 | 6.0 | 6.4 | 7.8 |

Results from growth analysis are summarized in the overview Table 24. The determined growth effects of specified construct group are presented as ratios between the construct group and wild type group for AFH, AFD, AMHGR, ADGR, MFH, MFD, MMHGR and MDC.

TABLE 24

Overview table of growth effects of construct M087

| Construct group | Average Final Height | Average Final Diameter | Average Maximum Height Growth Rate | Average Maximum Diameter Growth Rate | Maximum Final Height | Maximum Final Diameter | Maximum of Maximum Height Growth Rate | Maximum Diameter Growth Rate |
|---|---|---|---|---|---|---|---|---|
| M087 | 1.28 | 1.05 | 1.29 | 1.08 | 1.26 | 0.91 | 1.34 | 0.87 |

Growth effects on dry weight, leaf area and internode length are presented in Table 25. For each parameter, the construct group average and construct group line averages are expressed as a percentage of corresponding wild type group average.

TABLE 25

Dry weight, leaf area and internode length effects of construct M087

| Construction group/line | Wood | Bark | Total: Wood + Bark | 5 fully developed leaves | Remaining leaves | Total: Leaves | Total: Shoot | Leaf area | Specific Leaf Area | Internode Length |
|---|---|---|---|---|---|---|---|---|---|---|
| M087 average | 142 | 120 | 135 | 94 | 109 | 108 | 119 | 86 | 91 | 114 |
| M087-2B | 140 | 118 | 133 | 97 | 106 | 105 | 117 | 98 | 101 | 117 |
| M087-3A | 166 | 139 | 158 | 97 | 131 | 127 | 140 | 93 | 95 | 110 |
| M087-6A | 97 | 84 | 93 | 79 | 74 | 74 | 82 | 48 | 61 | 116 |

Construct group M087 showed a significant increase in "Wood" dry weight according to t-test (p=0.0058)

Construct group M087 showed a significant increase in "Wood+Bark" dry weight according to t-test (p=0.011)

Construct group line M087-3A showed a significant increased dry weight in, "Wood", "Bark", "Wood+Bark" and "Total: Shoot", based on line averages outside 95% confidence intervals around wild type.

Construct group lines M087-2B and M087-6A showed significant increased "Internode Length" based on line averages outside the 95% confidence intervals around wild type.

Construct Group M087rp1

Construct group M087rp1 corresponds to transgenic poplar plants overexpressing gene G189 (SEQ ID NO: 174) being replanted in the greenhouse. Again this construct induced increased growth. The final height of the construct group was 12% greater compared to that of the wild type control group. The maximum height growth rate of the construct group was 16% higher than that of the wild type control group. The M087rp1 construct group meets the more stringent level of growth difference selection criterion (1).

Tables 26 and 27 contain growth data for the specified construct group and corresponding wild type group. Table rows contain height and diameter measurements of individuals of the specified construct group and corresponding wild type group. Time of measurement as number of days in greenhouse is shown in the table headers.

TABLE 26

Height growth data (cm) for M087rp1

| Individual | \multicolumn{9}{c}{Days in Greenhouse} |
|---|---|---|---|---|---|---|---|---|---|
|  | 19 | 22 | 26 | 29 | 33 | 36 | 44 | 48 | 54 |
| M087rp1-2B-1 | 27 | 31 | 40 | 53 | 72 | 85 | 126 | 142 | 163 |
| M087rp1-2B-2 | 25 | 29 | 39 | 51 | 69 | 82 | 117 | 135 | 162 |
| M087rp1-2B-3 | 26 | 30 | 41 | 52 | 70 | 85 | 125 | 140 | 159 |
| M087rp1-3A-1 | 25 | 28 | 35 | 44 | 61 | 78 | 114 | 129 | 148 |
| M087rp1-3A-2 | 23 | 27 | 34 | 45 | 62 | 76 | 114 | 135 | 159 |
| M087rp1-3A-3 | 24 | 27 | 36 | 47 | 60 | 67 | 96 | 109 | 133 |
| M087rp1-3B-1 | 25 | 30 | 40 | 50 | 66 | 78 | 111 | 124 | 151 |
| M087rp1-3B-2 | 24 | 28 | 39 | 49 | 63 | 75 | 111 | 123 | 147 |
| M087rp1-3B-3 | N/A | 24 | 29 | 35 | 45 | 53 | 81 | 93 | 117 |
| M087rp1-5A-1 | 26 | 34 | 45 | 57 | 74 | 84 | 120 | 132 | 149 |
| M087rp1-5A-2 | 24 | 30 | 38 | 49 | 67 | 80 | 119 | 138 | 158 |
| M087rp1-5A-3 | 22 | 28 | 37 | 48 | 66 | 80 | 115 | 130 | 153 |
| M087rp1-6A-1 | 24 | 29 | 40 | 53 | 70 | 84 | 126 | 142 | 170 |
| M087rp1-6A-2 | 23 | 28 | 35 | 45 | 63 | 76 | 110 | 123 | 145 |
| M087rp1-6A-3 | 25 | 31 | 41 | 53 | 70 | 81 | 120 | 135 | 152 |
| T89-01 | 26 | 31 | 40 | 49 | 63 | 75 | 106 | 121 | 147 |
| T89-02 | 24 | 31 | 39 | 51 | 65 | 76 | 108 | 120 | 140 |
| T89-03 | 25 | 30 | 38 | 49 | 66 | 78 | 111 | 122 | 138 |
| T89-04 | 24 | 29 | 36 | 46 | 61 | 74 | 103 | 115 | 135 |
| T89-05 | 22 | 25 | 33 | 41 | 55 | 67 | 99 | 113 | 133 |
| T89-06 | 24 | 28 | 36 | 48 | 64 | 76 | 111 | 128 | 143 |

TABLE 26-continued

Height growth data (cm) for M087rp1

| Individual | Days in Greenhouse | | | | | | | | |
|---|---|---|---|---|---|---|---|---|---|
| | 19 | 22 | 26 | 29 | 33 | 36 | 44 | 48 | 54 |
| T89-07 | 24 | 32 | 40 | 53 | 71 | 84 | 119 | 137 | 153 |
| T89-08 | 22 | 27 | 36 | 47 | 62 | 72 | 101 | 114 | 133 |
| T89-09 | 22 | 26 | 34 | 44 | 57 | 67 | 97 | 108 | 131 |
| T89-10 | 23 | 28 | 35 | 45 | 56 | 70 | 96 | 107 | 126 |
| T89-11 | 22 | 28 | 37 | 47 | 63 | 76 | 106 | 120 | 139 |
| T89-12 | 23 | 28 | 36 | 45 | 58 | 67 | 94 | 106 | 120 |
| T89-13 | 27 | 31 | 40 | 49 | 61 | 71 | 102 | 114 | 132 |
| T89-14 | 23 | 28 | 37 | 46 | 59 | 70 | 101 | 114 | 133 |
| T89-15 | 25 | 30 | 39 | 51 | 67 | 78 | 106 | 122 | 140 |
| T89-16 | 23 | 26 | 35 | 44 | 56 | 67 | 100 | 112 | 136 |
| T89-17 | 22 | 25 | 34 | 44 | 57 | 70 | 102 | 115 | 136 |
| T89-18 | 21 | 26 | 34 | 43 | 57 | 69 | 100 | 113 | 134 |
| T89-19 | 23 | 28 | 37 | 46 | 61 | 73 | 105 | 120 | 139 |
| T89-20 | 24 | 29 | 40 | 50 | 66 | 79 | 113 | 126 | 144 |
| T89-21 | 26 | 33 | 41 | 53 | 70 | 81 | 114 | 133 | 149 |
| T89-22 | 23 | 28 | 36 | 46 | 60 | 71 | 101 | 116 | 136 |
| T89-23 | 23 | 29 | 35 | 46 | 60 | 71 | 100 | 115 | 135 |
| T89-24 | 23 | 27 | 35 | 44 | 55 | 62 | 84 | 92 | 102 |
| T89-25 | 22 | 26 | 33 | 41 | 55 | 66 | 95 | 107 | 128 |
| T89-26 | 25 | 28 | 37 | 46 | 59 | 70 | 100 | 117 | 135 |
| T89-27 | 24 | 30 | 38 | 47 | 63 | 71 | 102 | 115 | 133 |
| T89-28 | 21 | 27 | 33 | 43 | 55 | 67 | 96 | 114 | 127 |
| T89-29 | 23 | 27 | 35 | 44 | 57 | 68 | 97 | 109 | 129 |
| T89-30 | 24 | 28 | 37 | 49 | 64 | 76 | 109 | 120 | 137 |
| T89-31 | 22 | 25 | 33 | 42 | 57 | 65 | 97 | 105 | 128 |
| T89-32 | 23 | 28 | 36 | 48 | 62 | 76 | 107 | 120 | 140 |
| T89-33 | 24 | 28 | 37 | 47 | 59 | 71 | 104 | 117 | 138 |
| T89-34 | N/A | N/A | N/A | N/A | N/A | N/A | N/A | N/A | N/A |
| T89-35 | 23 | 29 | 36 | 47 | 63 | 76 | 107 | 123 | 141 |
| T89-36 | 21 | 25 | 33 | 42 | 56 | 69 | 97 | 113 | 131 |
| T89-37 | 25 | 28 | 35 | 45 | 61 | 72 | 104 | 117 | 135 |
| T89-38 | 23 | 28 | 35 | 45 | 60 | 72 | 100 | 113 | 133 |
| T89-39 | 26 | 29 | 38 | 48 | 63 | 75 | 105 | 117 | 136 |
| T89-40 | 23 | 28 | 37 | 47 | 56 | 68 | 98 | 110 | 130 |
| T89-41 | 27 | 31 | 40 | 51 | 66 | 81 | 113 | N/A | 142 |
| T89-42 | 21 | 25 | 33 | 41 | 51 | 63 | 91 | 102 | 116 |

TABLE 27

Diameter growth data (mm) for M087rp1

| Individual | Days in Greenhouse | | |
|---|---|---|---|
| | 35 | 42 | 63 |
| M087rp1-2B-1 | 2.9 | 4.5 | 6.7 |
| M087rp1-2B-2 | 3.1 | 4.7 | 8.1 |
| M087rp1-2B-3 | 3.5 | 4.6 | 7.9 |
| M087rp1-3A-1 | 2.8 | 3.9 | 7.0 |
| M087rp1-3A-2 | 3.0 | 3.7 | 6.8 |
| M087rp1-3A-3 | 3.4 | 3.7 | 6.7 |
| M087rp1-3B-1 | 3.3 | 3.9 | 7.7 |
| M087rp1-3B-2 | 2.8 | 3.9 | 6.8 |
| M087rp1-3B-3 | 2.3 | 2.9 | 8.0 |
| M087rp1-5A-1 | 3.5 | 4.2 | 7.2 |
| M087rp1-5A-2 | 3.5 | 4.4 | 9.5 |
| M087rp1-5A-3 | 3.0 | 4.0 | 7.4 |
| M087rp1-6A-1 | 3.2 | 4.4 | 8.6 |
| M087rp1-6A-2 | 3.7 | 4.2 | 8.6 |
| M087rp1-6A-3 | 3.4 | 4.7 | 8.6 |
| T89-01 | 3.4 | 4.5 | 7.2 |
| T89-02 | 3.4 | 4.8 | 8.6 |
| T89-03 | 3.6 | 4.9 | 7.7 |
| T89-04 | 3.0 | 4.3 | 7.0 |
| T89-05 | 3.3 | 4.2 | 7.6 |
| T89-06 | 3.0 | 4.6 | 8.9 |
| T89-07 | 3.4 | 5.2 | 9.0 |
| T89-08 | 2.9 | 4.8 | 7.5 |
| T89-09 | 3.2 | 4.4 | 7.0 |
| T89-10 | 3.2 | 4.3 | 7.1 |
| T89-11 | 3.7 | 5.6 | 6.1 |
| T89-12 | 3.0 | 3.9 | 6.3 |
| T89-13 | 3.1 | 4.6 | 7.7 |
| T89-14 | 3.1 | 4.3 | 8.9 |
| T89-15 | 3.4 | 4.9 | 10.3 |
| T89-16 | 2.9 | 4.2 | 7.0 |
| T89-17 | 3.0 | 4.8 | 8.2 |
| T89-18 | 3.2 | 4.6 | 7.5 |
| T89-19 | 3.2 | 4.6 | 8.6 |
| T89-20 | 3.3 | 4.1 | 7.5 |
| T89-21 | 4.1 | 5.0 | 9.5 |
| T89-22 | 3.2 | 5.0 | 8.4 |
| T89-23 | 3.0 | 4.2 | 7.2 |
| T89-24 | 3.4 | 3.7 | 6.3 |
| T89-25 | 2.7 | 3.9 | 7.3 |
| T89-26 | 3.2 | 5.0 | 6.9 |
| T89-27 | 3.0 | 4.0 | 7.1 |
| T89-28 | 2.9 | 4.3 | 8.9 |
| T89-29 | 3.3 | 4.7 | 9.1 |
| T89-30 | 3.1 | 4.3 | 6.6 |
| T89-31 | 2.8 | 4.2 | 7.0 |
| T89-32 | 3.1 | 4.8 | 8.0 |
| T89-33 | 3.1 | 4.7 | 6.8 |
| T89-34 | N/A | N/A | N/A |
| T89-35 | 3.3 | 4.9 | 8.5 |
| T89-36 | 3.1 | 4.0 | 8.7 |
| T89-37 | 2.7 | 4.0 | 6.4 |
| T89-38 | 3.0 | 4.5 | 7.4 |
| T89-39 | 2.9 | 4.0 | 7.2 |
| T89-40 | 3.3 | 4.3 | 6.8 |
| T89-41 | 3.6 | 5.2 | 9.0 |
| T89-42 | 2.6 | 3.9 | 5.6 |

Results from the growth analysis are summarized in the overview Table 28. The determined growth effects of the specified construct group are presented as ratios between construct and wild type group AFH, AFD, AMHGR, ADGR, MFH, MFD, MMHGR and MDC.

TABLE 28

Overview table of growth effects of construct M087rp1

| Construct group | Average Final Height | Average Final Diameter | Average Maximum Height Growth Rate | Average Maximum Diameter Growth Rate | Maximum Final Height | Maximum Final Diameter | Maximum of Maximum Height Growth Rate | Maximum Maximum Diameter Growth Rate |
|---|---|---|---|---|---|---|---|---|
| M087rp1 | 1.12 | 1.01 | 1.16 | 1.04 | 1.11 | 0.92 | 1.11 | 0.88 |

Growth effects on dry weight, leaf area and internode length are presented in Table 29. For each parameter, the construct group average and construct group line averages are expressed as a percentage of corresponding wild type group average.

TABLE 29

Dry weight, leaf area and internode length effects of construct M087rp1

| Construction group/line | Wood | Bark | Total: Wood + Bark | 5 fully developed leaves | Remaining leaves | Total: Leaves | Total: Shoot | Leaf area | Specific Leaf Area | Internode Length |
|---|---|---|---|---|---|---|---|---|---|---|
| M087rp1 average | 118 | 101 | 113 | 83 | 97 | 96 | 103 | 91 | 114 | 112 |
| M087rp1-2B | 143 | 124 | 137 | 87 | 115 | 111 | 122 | 89 | 102 | 111 |
| M087rp1-3A | 110 | 88 | 103 | 79 | 95 | 93 | 97 | 93 | 117 | 105 |
| M087rp1-3B | 98 | 84 | 93 | 81 | 83 | 82 | 87 | 86 | 106 | 111 |
| M087rp1-5A | 128 | 113 | 123 | 78 | 103 | 100 | 109 | 101 | 143 | 116 |
| M087rp1-6A | 112 | 98 | 107 | 88 | 92 | 91 | 98 | 86 | 101 | 117 |

Construct group M087rp1 had a significant increase in dry weight "Wood" according to a t-test (p=0.048)

Construct group M087rp1 had a significantly decreased "Root/Shoot" ratio according to a t-test (p=0.00085). A decreased Root/Shoot ratio is generally correlated to fast growing individual or species, the rationale for this is that more resources can be invested in phosynthetic leaves and for trees in the main product the woody stem. This is especially true when nutrients and water are in good supply.

Construct group M087rp1 had a significant increased "Specific Leaf Area" according to a t-test (p=0.036)

Construct group M087rp1 had a significant increased "Internode length" according to a t-test p=0.000014)

Construct group line M087rp1-3A had significantly increased "Specific leaf Area" based on the line average being outside the 95% confidence intervals around wild type.

Construct group line M087rp1-5A had significant increased "Specific leaf Area" and "Internode length" based on the line average, which is outside the 95% confidence intervals around wild type.

Construct group line M087rp1-6A had significant increased "Internode length" based on the line average, which is outside the 95% confidences interval around wild type.

TABLE 30

Density M087rp1

| Individual | Density (g/cm3) |
|---|---|
| M087rp1-2B-2 | 0.3027 |
| M087rp1-3A-1 | 0.3169 |
| M087rp1-3B-2 | 0.3333 |

TABLE 30-continued

Density M087rp1

| Individual | Density (g/cm3) |
|---|---|
| M087rp1-5A-3 | 0.3130 |
| M087rp1-6A-3 | 0.3041 |
| T89-02 | 0.270 |
| T89-04 | 0.278 |
| T89-05 | 0.272 |
| T89-10 | 0.261 |
| T89-17 | 0.272 |
| T89-19 | 0.275 |
| T89-21 | 0.274 |
| T89-25 | 0.262 |
| T89-27 | 0.266 |
| T89-30 | 0.277 |
| T89-36 | 0.252 |
| T89-37 | 0.289 |
| T89-41 | 0.281 |
| T89-42 | 0.280 |

Construct group M087rp1 had increased wood density on average 15.4% higher density than wild type, this is a significant change according to t-test p=0.000001. All samples in construct group M087rp1 were outside a 95% confidence interval around wild type.

Construct Group M110

Construct group M110 corresponds to transgenic poplar plants overexpressing gene G2142 (SEQ ID NO: 225).

Growth effects on dry weight, leaf area and internode length are presented in Table 31. For each parameter, the construct group average and construct group line averages are expressed as a percentage of corresponding wild type group average.

TABLE 31

Dry weight, leaf area and internode length effects of construct M110

| Construction group/line | Wood | Bark | Total: Wood + Bark | 5 fully developed leaves | Remaining leaves | Total: Leaves | Total: Shoot | Leaf area | Specific Leaf Area | Internode Length |
|---|---|---|---|---|---|---|---|---|---|---|
| M110 average | 135 | 131 | 134 | 105 | 130 | 127 | 130 | 109 | 97 | 98 |
| M110-2A | 142 | 133 | 140 | 116 | 119 | 118 | 127 | 111 | 96 | 100 |
| M110-2B | 97 | 102 | 98 | 65 | 114 | 109 | 105 | 64 | 98 | 90 |
| M110-3B | 167 | 158 | 164 | 135 | 156 | 154 | 158 | 130 | 97 | 105 |

Construct group M110 showed a significant increase in "Wood" dry weight according to a t-test (p=0.015)

Construct group M110 showed a significant increase in "Bark" dry weight according to a t-test (p=0.0074)

Construct group M110 showed a significant increase in "Wood+Bark" dry weight according to a t-test (p=0.012)

Construct group M110 showed a significant increase in "Remaining leaves" dry weight according to a t-test (p=0.0084)

Construct group M110 showed a significant increase in "Total:Leaves" dry weight according to a t-test (p=0.012)

Construct group M110 showed a significant increase in "Total:Shoot" dry weight according to a t-test (p=0.010)

Construct group line M110-3B showed significantly increased dry weight in; "Wood", "Bark", "Wood+Bark", "5 fully developed leaves", "Remaining leaves", "Total: Leaves", "Total: Shoot", and "Leaf area", based on the line averages, which are outside the 95% confidence intervals around wild type.

Construct Group M110rp1

Construct group M110rp1 corresponds to transgenic poplar plants overexpressing gene G2142 (SEQ ID NO: 225).

Growth effects on dry weight, leaf area and internode length are presented in Table 32. For each parameter, the construct group average and construct group line averages are expressed as a percentage of corresponding wild type group average.

"Total:Shoot including root" and "Root", based on the line averages, which were outside the 95% confidence intervals around wild type.

Construct Group M110rp2

In a second replant, the M110rp2 construct group again was found to have increased growth, including statistically significantly increased growth height (+7%), increased stem volume (+12%) and increased wood dry weight (+12%) compared to WT. Line M110rp2-3B had statistically significantly increased growth height (+12%). The overall results of the M11rp2 construct group suggest altered growth properties, for example Line M110rp2-3B showed increased growth height (+12%), increased stem volume (+15%), increased wood dry weight (15%), increased bark dry weight (+12%) and increased total shoot dry weight (+6%) compared to WT but these results were not statistically significant according to a t-test. However no reduction in any of the measured parameters could be shown.

Construct Group M030

Construct group M030 corresponds to transgenic poplar plants overexpressing gene G2552 (SEQ ID NO: 329). This construct induced increased growth. The average final diameter of the construct group was 16% higher than that of the wild type control group. The average diameter growth rate of the construct group was 36% higher than that of the wild type control group. The average final height was 13%

TABLE 32

Dry weight, leaf area and internode length effects of construct M110rp1

| Construction group/line | Wood | Bark | Total: Wood + Bark | 5 fully developed leaves | Remaining leaves | Total: Leaves | Total: Shoot | Leaf area | Specific Leaf Area | Inter-node Length |
|---|---|---|---|---|---|---|---|---|---|---|
| M110rp1 average | 110 | 108 | 109 | 107 | 108 | 108 | 109 | 106 | 102 | 104 |
| M110rp1-1A | 120 | 121 | 120 | 133 | 119 | 121 | 121 | 122 | 91 | 109 |
| M110rp1-1B | 160 | 147 | 156 | 113 | 149 | 145 | 149 | 122 | 117 | 96 |
| M110rp1-2A | 107 | 111 | 109 | 121 | 115 | 115 | 113 | 108 | 91 | 99 |
| M110rp1-3A | 80 | 77 | 79 | 73 | 78 | 77 | 78 | 85 | 115 | 104 |
| M110rp1-3B | 82 | 82 | 82 | 96 | 81 | 83 | 83 | 93 | 96 | 111 |

| Construction group/line | Root | Total: Shoot + root | Root/Shoot |
|---|---|---|---|
| M110rp1 average | 103 | 108 | 93 |
| M110rp1-1A | 105 | 118 | 86 |
| M110rp1-1B | 154 | 150 | 103 |
| M110rp1-2A | 110 | 112 | 97 |
| M110rp1-3A | 70 | 77 | 89 |
| M110rp1-3B | 74 | 81 | 89 |

Construct group lines M110rp1-1B showed significantly increased dry weight; "Wood", "Bark", "Total: Wood+Bark", "Remaining leaves", "Total:Leaves", "Total:Shoot", greater than that of the wild type control group. The maximum height growth rate was 15% higher than that of the wild type control group. The M030 construct group meets the more stringent level of growth difference selection criteria (2) and (3) and the less stringent level of growth criteria (1) and (4).

Tables 33 and 34 contain growth data for the specified construct group and corresponding wild type group. Table rows contain height and diameter measurements of individuals of the specified construct group and corresponding wild type group. Time of measurement as number of days in greenhouse is shown in the table headers.

TABLE 33

Height growth data (cm) for M030

| Individual | Days in Greenhouse | | | | | | |
|---|---|---|---|---|---|---|---|
| | 17 | 25 | 31 | 38 | 42 | 45 | 52 |
| M030-1A-1 | 10 | 24 | 36 | 49 | 58 | 66 | 83 |
| M030-1A-2 | 19 | 26 | 37 | 49 | 57 | 65 | 84 |
| M030-1A-3 | 15 | 24 | 36 | 50 | 58 | 67 | 87 |
| M030-2B-1 | 17 | 24 | 36 | 46 | 55 | 62 | 77 |
| M030-2B-2 | 16 | 22 | 31 | 41 | 50 | 56 | 72 |
| M030-2B-3 | 18 | 23 | 35 | 47 | 56 | 64 | 81 |
| M030-3A-1 | 18 | 22 | 34 | 48 | 59 | 67 | 85 |
| M030-3A-2 | 21 | 26 | 42 | 56 | N/A | 75 | 91 |
| M030-3A-3 | 19 | 26 | 39 | 52 | 63 | 70 | 88 |
| T89-13 | 19 | 27 | 34 | 51 | 63 | 68 | 85 |
| T89-14 | 17 | 15 | 20 | 25 | 32 | 37 | 50 |
| T89-15 | 18 | 24 | 37 | 50 | 56 | 64 | 81 |
| T89-16 | 19 | 26 | 37 | 48 | 58 | 64 | 79 |
| T89-17 | 18 | 24 | 35 | 48 | 54 | 60 | 72 |
| T89-18 | 16 | 19 | 30 | 42 | 50 | 57 | 65 |
| T89-19 | 18 | 26 | 37 | 48 | 59 | 66 | 82 |
| T89-20 | 15 | 22 | 33 | 45 | 55 | 63 | 78 |
| T89-21 | 17 | 23 | 35 | 47 | 53 | 61 | 79 |
| T89-22 | 12 | 16 | 23 | 32 | 40 | 47 | 59 |
| T89-23 | 19 | 27 | 39 | 51 | 57 | 61 | 70 |
| T89-24 | 18 | 25 | 37 | 49 | 57 | 64 | 81 |
| T89-25 | 16 | 21 | 29 | 41 | 51 | 58 | 74 |

TABLE 34

Diameter growth data for M030

| Individual | Days in Greenhouse | | |
|---|---|---|---|
| | 34 | 41 | 55 |
| M030-1A-1 | 4.7 | 6.2 | 7.7 |
| M030-1A-2 | 5.2 | 6.3 | 7.5 |
| M030-1A-3 | 4.3 | 5.7 | 6.5 |
| M030-2B-1 | 4.3 | 5.4 | 6.5 |
| M030-2B-2 | 3.9 | 5.5 | 5.8 |
| M030-2B-3 | 4.2 | 5.5 | 6.4 |
| M030-3A-1 | 5.1 | 5.8 | 7.3 |
| M030-3A-2 | 5.3 | 6.3 | 7.3 |
| M030-3A-3 | 4.1 | 6.2 | 6.3 |
| T89-13 | 4.7 | 5.1 | 5.8 |
| T89-14 | 2.5 | 3.1 | 4.5 |
| T89-15 | 4.5 | 5.4 | 7.0 |
| T89-16 | 4.2 | 5.5 | 5.8 |
| T89-17 | 4.8 | 5.5 | 6.3 |
| T89-18 | 4.5 | 6.2 | 5.2 |
| T89-19 | 4.3 | 5.5 | 6.2 |
| T89-20 | 4.6 | 5.4 | 6.6 |
| T89-21 | 4.5 | 5.4 | 6.3 |
| T89-22 | 3.1 | 4.4 | 5.1 |
| T89-23 | 4.4 | 4.4 | 5.3 |
| T89-24 | 4.4 | 4.9 | 6.3 |
| T89-25 | 5.2 | 5.2 | 6.4 |

Results from growth analysis are specified in the overview Table 35. The determined growth effects of the specified construct group are presented as ratios between construct and wild type group for AFH, AFD, AMHGR, ADGR, MFH, MFD, MMHGR and MDC.

TABLE 35

Overview table of growth effects of construct M030

| Construct group | Average Final Height | Average Final Diameter | Average Maximum Height Growth Rate | Average Diameter Growth Rate | Maximum Final Height | Maximum Final Diameter | Maximum of Maximum Height Growth Rate | Maximum Diameter Growth Rate |
|---|---|---|---|---|---|---|---|---|
| M030 | 1.13 | 1.16 | 1.15 | 1.36 | 1.07 | 1.11 | 1.08 | 1.19 |

Growth effects on dry weight, leaf area and internode length are presented in Table 36. For each parameter, the construct group average and construct group line averages are expressed as a percentage of corresponding wild type group average.

TABLE 36

Dry weight, leaf area and internode length effects of construct M030

| Construction group/line | Wood | Bark | Total: Wood + Bark | 5 fully developed leaves | Remaining leaves | Total: Leaves | Total: Shoot | Leaf area | Specific Leaf Area | Internode Length |
|---|---|---|---|---|---|---|---|---|---|---|
| M030 average | 151 | 139 | 147 | 131 | 130 | 130 | 134 | 136 | 106 | 106 |
| M030-1A | 157 | 138 | 151 | 131 | 132 | 132 | 137 | 139 | 110 | 113 |

TABLE 36-continued

Dry weight, leaf area and internode length effects of construct M030

| Construction group/line | Wood | Bark | Total: Wood + Bark | 5 fully developed leaves | Remaining leaves | Total: Leaves | Total: Shoot | Leaf area | Specific Leaf Area | Internode Length |
|---|---|---|---|---|---|---|---|---|---|---|
| M030-2B | 110 | 104 | 108 | 116 | 109 | 111 | 110 | 119 | 105 | 98 |
| M030-3A | 185 | 173 | 181 | 147 | 147 | 147 | 156 | 149 | 104 | 107 |

Construct group M030 showed a significant increase in "5 fully developed leaves" dry weight according to a t-test (p=0.032) Construct group M030 showed a significant increase in "Leaf area" according to a t-test (p=0.025) Construct group line M030-3A showed significantly increased dry weight in; "Bark" and "Wood++Bark" based on the line average, which is outside the 95% confidence intervals around wild type.

Construct Group M030rp1

Construct group M030rp1 corresponds to transgenic poplar plants overexpressing gene G2552 (SEQ ID NO: 329).

Growth effects on dry weight, leaf area and internode length are presented in Table 37. For each parameter, the construct group average and construct group line averages are expressed as a percentage of corresponding wild type group average.

altered total shoot dry weight (+12%) but these results were not statistically significant according to a t-test. Line M030rp2-3A had normal growth height, positively altered stem diameter (+7%), and stem volume (+16%) but these results were not statistically significant according to a t-test. Line M030rp2-2B showed a significant decrease in stem volume (−20%), leaves dry weight (−18%) and total shoot dry weight (−18%).

The result of M030 Q-PCR, in FIG. 2 and the Table 38, correlated well with the growth results. The Q-PCR results, gene/26s-ratio, of line M030-1A and M030-3A suggested that the expression levels of G2552 in these lines were higher than expression level in line M030-2B. These differences in expression levels in parallel with the growth studies confirm the suggestion that this gene affects growth.

TABLE 37

Dry weight, leaf area and internode length effects of construct M030rp1

| Construction group/line | Wood | Bark | Total: Wood + Bark | 5 fully developed leaves | Remaining leaves | Total: Leaves | Total: Shoot | Leaf area | Specific Leaf Area | Internode Length | Root | Total: Shoot + root | Root/ Shoot |
|---|---|---|---|---|---|---|---|---|---|---|---|---|---|
| M030rp1 average | 90 | 93 | 91 | 100 | 90 | 91 | 91 | 96 | 95 | 113 | 79 | 89 | 86 |
| M030rp1-1A | 101 | 97 | 100 | 113 | 94 | 96 | 98 | 109 | 95 | 115 | 85 | 96 | 85 |
| M030rp1-2B | 92 | 101 | 95 | 101 | 94 | 95 | 95 | 98 | 96 | 106 | 84 | 93 | 88 |
| M030rp1-3A | 98 | 96 | 97 | 97 | 97 | 97 | 97 | 86 | 89 | 105 | 77 | 93 | 79 |
| M030rp1-3B | 67 | 78 | 71 | 91 | 73 | 75 | 74 | 91 | 100 | 128 | 69 | 73 | 93 |

Construct group M030rp1 showed a significant decrease in "Root/Shoot" ratio according to a t-test (p=0.0057)

Construct group M030rp1 had a significant increase in "Internode length" according to a t-test (p=0.000086)

Construct group lines M030rp1-1A and M030rp1-3B showed significant increased; "Internode length", based on the line average, which is outside of 95% confidence interval around wild type.

In a second replant, the M030rp2 construct group showed statistically significantly increased growth height (+4%) compared to WT. Line M030rp2-1A had statistically significantly increased growth height (+9%), normal diameter, normal wood density and increased wood dry weight (+19%). Line M030rp2-1A also had positively altered stem volume (+13%), positively altered bark dry weight (+13%), positively altered leaves dry weight (+8%) and positively

TABLE 38

Q-PCR analysis of construct group M030

| | M030-1A | M030-2B | M030-3A | M030-3B |
|---|---|---|---|---|
| Ratio(gene/26S) | 0.0151 | 0.0038 | 0.0185 | 0.0028 |
| Error (sum of diff.) | 0.54 | 0.96 | 0.77 | 1.13 |

Construct Group M025

Construct group M025 corresponds to transgenic poplar plants overexpressing gene G2724 (SEQ ID NO: 399).

Growth effects on dry weight, leaf area and internode length are presented in Table 39. For each parameter, the construct group average and construct group line averages are expressed as a percentage of corresponding wild type group average.

TABLE 39

Dry weight, leaf area and internode length effects of construct M025

| Construction group/line | Wood | Bark | Total: Wood + Bark | 5 fully developed leaves | Remaining leaves | Total: Leaves | Total: Shoot | Leaf area | Specific Leaf Area | Internode Length |
|---|---|---|---|---|---|---|---|---|---|---|
| M025 average | 147 | 134 | 143 | 124 | 132 | 131 | 135 | 121 | 97 | 103 |

TABLE 39-continued

Dry weight, leaf area and internode length effects of construct M025

| Construction group/line | Wood | Bark | Total: Wood + Bark | 5 fully developed leaves | Remaining leaves | Total: Leaves | Total: Shoot | Leaf area | Specific Leaf Area | Internode Length |
|---|---|---|---|---|---|---|---|---|---|---|
| M025-1A | 142 | 136 | 140 | 113 | 121 | 120 | 127 | 117 | 103 | 102 |
| M025-2A | 163 | 142 | 157 | 132 | 144 | 143 | 148 | 123 | 93 | 102 |
| M025-6A | 136 | 125 | 133 | 128 | 130 | 130 | 131 | 122 | 96 | 107 |

Construct group M025 showed a significant increase in "Wood" dry weight according to a t-test (p=0.0027)

Construct group M025 showed a significant increase in "Bark" dry weight according to a t-test (p=0.0042)

Construct group M025 showed a significant increase in "Wood+Bark" dry weight according to a t-test (p=0.0027)

Construct group M025 showed a significant increase in "5 fully developed leaves" dry weight according to a t-test (p=0.045)

Construct group M025 showed a significant increase in "Remaining leaves" dry weight according to a t-test (p=0.0019)

Construct group M025 showed a significant increase in "Total:Leaves" dry weight according to a t-test (p=0.0024)

Construct group M025 showed a significant increase in "Total:Shoot" dry weight according to a t-test (p=0.0021)

Construct group M025 showed a significant increase in "Leaf area" according to a t-test (p=0.050)

Construct group line M025-2A showed significantly increased dry weight in; "Wood", "Wood+Bark", "Remaining leaves", "Total: Leaves" and "Total: Shoot", based on the line averages, which are outside the 95% confidences intervals around wild type.

Construct group line M025-6A showed significantly increased dry weight in; "Remaining leaves", according to the line averages, which are outside the 95% confidences intervals around wild type.

Construct Group M025rp1

Construct group M025rp1 corresponds to transgenic poplar plants overexpressing gene G2724 (SEQ ID NO: 399).

Growth effects on dry weight, leaf area and internode length are presented in Table 40. For each parameter, the construct group average and construct group line averages are expressed as a percentage of corresponding wild type group average.

compared to WT. Line M025rp2-1A had statistically significantly increased growth height (+18%), increased growth diameter (+10%), increased stem volume (+40%), normal wood density, increased wood dry weight (+36%), increased bark dry weight (+22%), increased dry weight of leaves (+18%) and increased total shoot dry weight (+24%) compared to WT. M025rp2 lines 2A and 6A showed a significant decrease in dry weight compared to WT. Line M025rp2-2A showed significant decreased bark dry weight (−16%) and leaf dry weight (−13%). Line M025rp-6A showed significant decreased wood dry weight (−15%), bark dry weight (−19%), leaf dry weight (−15%) and total shoot dry weight (−16%).

The result of M025 Q-PCR, in FIG. 3 and Table 41, correlated well to the result in growth increase. The Q-PCR result, gene/26s-ratio, of line M025-1A suggests that the expression level in this line was 6 times higher than expression level of line M025-2A and 260 times higher than expression level of line M025-6A. These differences in expression levels in parallel with the growth studies confirmed that this gene affects growth.

TABLE 41

Q-PCR of construct group M025: Tissue culture Material, one leaf

| | M025-1A | M025-2A | M025-6A | M025-6B |
|---|---|---|---|---|
| Ratio (Gene/26S) | 1.045 | 0.164 | 0.004 | 0.002 |
| Error (sum of diff.) | 0.19 | 0.51 | 0.99 | 2.87 |

Construct Group M075

Construct group M075 corresponds to transgenic poplar plants overexpressing gene G287 (SEQ ID NO: 435). This construct induced increased growth. The average final height of the construct group was 8% greater than that of the corresponding wild type control group. The maximum height growth rate of the construct group was 10% higher than that of the wild type control group. The M075 construct group meets growth difference selection criterion (1).

Tables 42 and 43 contain growth data for the specified construct group and corresponding wild type group. Table

TABLE 40

Dry weight, leaf area and internode length effects of construct M025rp1

| Construction group/line | Wood | Bark | Total: Wood + Bark | 5 fully developed leaves | Remaining leaves | Total: Leaves | Total: Shoot | Leaf area | Specific Leaf Area | Internode Length | Root | Total: Shoot + root | Root/ Shoot |
|---|---|---|---|---|---|---|---|---|---|---|---|---|---|
| M025rp1 average | 94 | 93 | 93 | 88 | 93 | 92 | 93 | 88 | 100 | 99 | 84 | 91 | 89 |
| M025rp1-1A | 97 | 90 | 95 | 81 | 95 | 93 | 94 | 81 | 100 | 104 | 79 | 91 | 84 |
| M025rp1-2A | 98 | 98 | 98 | 93 | 98 | 97 | 97 | 89 | 95 | 95 | 104 | 98 | 107 |
| M025rp1-6A | 94 | 92 | 93 | 82 | 95 | 93 | 93 | 94 | 116 | 99 | 78 | 90 | 83 |
| M025rp1-6B | 86 | 93 | 89 | 97 | 84 | 86 | 87 | 88 | 88 | 98 | 74 | 84 | 83 |

Construct group M025rp1 had a significant decrease in "Root/Shoot" ratio according to t-test (p=0.039) which is favorable in some growth conditions.

Construct Group M025rp2

In a second replant, the M025rp2 construct group had statistically significantly increased growth height (+4%)

rows contain height and diameter measurements of individuals of the specified construct group and corresponding wild type group. Time of measurement as number of days in greenhouse is shown in the table headers.

TABLE 42

Height growth data (cm) for M075

| | Days in greenhouse | | | | | | |
|---|---|---|---|---|---|---|---|
| Individual | 21 | 27 | 34 | 41 | 48 | 51 | 55 |
| M075-1B-1 | 31 | 49 | 77 | 110 | 138 | 152 | 163 |
| M075-1B-2 | 32 | 50 | 77 | 109 | 140 | 155 | 172 |
| M075-1B-3 | 25 | 41 | 68 | 101 | 129 | 142 | 158 |
| M075-2B-1 | 31 | 46 | 74 | 103 | 127 | 139 | 156 |
| M075-2B-2 | 30 | 47 | 78 | 105 | 134 | 148 | 161 |
| M075-2B-3 | 28 | 39 | 63 | 92 | 116 | 128 | 141 |
| M075-7-1 | 26 | 42 | 72 | 100 | 130 | 144 | 158 |
| M075-7-2 | 35 | 50 | 78 | 106 | 134 | 143 | 157 |
| M075-7-3 | 33 | 51 | 84 | 116 | 142 | 152 | 168 |
| T89-19 | 32 | 45 | 70 | 97 | 123 | 134 | 147 |
| T89-20 | 30 | 45 | 66 | 90 | 119 | 130 | 145 |
| T89-21 | 36 | 51 | 77 | 103 | 131 | 142 | 156 |
| T89-22 | 35 | 53 | 80 | 109 | 133 | 145 | 163 |
| T89-23 | 32 | 46 | 71 | 96 | 122 | 133 | 152 |
| T89-24 | 33 | 46 | 67 | 91 | 117 | 128 | 141 |
| T89-25 | 30 | 45 | 65 | 90 | 116 | 129 | 143 |
| T89-26 | 33 | 46 | 70 | 100 | 129 | 140 | 155 |
| T89-27 | 31 | 45 | 71 | 99 | N/A | 141 | 154 |
| T89-28 | 29 | 42 | 65 | 94 | 120 | 131 | 147 |
| T89-29 | 34 | 49 | 75 | 103 | 130 | 143 | 157 |
| T89-30 | 32 | 48 | 72 | 96 | 122 | 132 | 145 |
| T89-31 | 30 | 44 | 65 | 90 | 116 | 125 | 138 |
| T89-32 | 28 | 40 | 59 | 82 | 107 | 118 | 131 |
| T89-33 | 30 | 45 | 72 | 102 | 127 | 138 | 153 |
| T89-34 | 28 | 42 | 67 | 95 | N/A | 131 | 146 |
| T89-35 | 38 | 54 | 81 | 110 | 131 | 148 | 161 |
| T89-36 | 34 | 49 | 77 | 104 | 134 | 147 | 161 |
| T89-37 | 29 | 45 | 70 | 98 | 124 | 135 | 150 |
| T89-38 | 28 | 41 | 61 | 84 | 109 | 119 | 131 |
| T89-39 | 33 | 46 | 65 | 87 | 111 | 121 | 134 |

TABLE 43

Diameter growth data (mm) for M075

| | Days in greenhouse | | | |
|---|---|---|---|---|
| Individual | 34 | 41 | 48 | 55 |
| M075-1B-1 | 6.2 | 7.6 | 8.2 | 9.5 |
| M075-1B-2 | 6.1 | 7.5 | 8.7 | 10.0 |
| M075-1B-3 | 5.4 | 7.1 | 8.4 | 10.4 |
| M075-2B-1 | 5.1 | 6.1 | 7.4 | 10.1 |
| M075-2B-2 | 4.8 | 7.2 | 7.1 | 8.3 |
| M075-2B-3 | 4.8 | 6.0 | 7.7 | 7.9 |
| M075-7-1 | 5.0 | 6.3 | 7.8 | 8.8 |
| M075-7-2 | 5.4 | 6.0 | 7.2 | 8.4 |
| M075-7-3 | 5.3 | 7.0 | 7.8 | 9.6 |
| T89-19 | 5.9 | 6.4 | 6.9 | 8.4 |
| T89-20 | 5.4 | 6.5 | 6.9 | 9.0 |
| T89-21 | 5.8 | 7.1 | 8.1 | 9.5 |
| T89-22 | 5.9 | 5.7 | 8.5 | 10.1 |
| T89-23 | 4.9 | 5.9 | 6.8 | 8.8 |
| T89-24 | 5.4 | 6.2 | 7.2 | 8.8 |
| T89-25 | 4.7 | 5.9 | 6.6 | 8.6 |
| T89-26 | 5.7 | 6.5 | 7.8 | 8.5 |
| T89-27 | 5.5 | 6.5 | 8.8 | 9.3 |
| T89-28 | 5.6 | 7.5 | 7.5 | 9.4 |
| T89-29 | 5.1 | 6.2 | 7.7 | 9.7 |
| T89-30 | 6.1 | 6.3 | 7.7 | 8.3 |
| T89-31 | 5.0 | 6.6 | 6.6 | 8.4 |
| T89-32 | 4.8 | 5.8 | 6.0 | 7.2 |
| T89-33 | 5.6 | 6.1 | 7.7 | 9.2 |
| T89-34 | 4.7 | 6.2 | 7.9 | 9.5 |
| T89-35 | 5.6 | 6.6 | 8.2 | 9.3 |
| T89-36 | 5.5 | 6.6 | 8.3 | 11.3 |
| T89-37 | 5.8 | 6.7 | 7.5 | 10.0 |
| T89-38 | 5.2 | 6.4 | 6.5 | 8.1 |
| T89-39 | 5.1 | 6.0 | 6.4 | 7.8 |

Results from growth analysis are summarized in the overview Table 44. The determined growth effects of the specified construct group are presented as ratios between the construct group and wild type group for AFH, AFD, AMHGR, ADGR, MFH, MFD, MMHGR and MDC.

TABLE 44

Overview table of growth effects of construct M075

| Construct group | Average Final Height | Average Final Diameter | Average Maximum Height Growth Rate | Average Diameter Growth Rate | Maximum Final Height | Maximum Final Diameter | Maximum of maxumim Height Growth Rate | Maximum Diameter Growth Rate |
|---|---|---|---|---|---|---|---|---|
| M075 | 1.08 | 1.03 | 1.10 | 1.04 | 1.06 | 0.92 | 1.10 | 0.86 |

Growth effects on dry weight, leaf area and internode length are presented in Table 45. For each parameter, the construct group average and construct group line averages are expressed as a percentage of corresponding wild type group average.

TABLE 45

Dry weight, leaf area and internode length effects of construct M075

| Construction group/line | Wood | Bark | Total: Wood + Bark | 5 fully developed leaves | Remaining leaves | Total: Leaves | Total: Shoot | Leaf area | Specific Leaf Area | Internode Length |
|---|---|---|---|---|---|---|---|---|---|---|
| M075 average | 113 | 111 | 112 | 100 | 104 | 103 | 107 | 99 | 98 | 104 |
| M075-1B | 129 | 125 | 128 | 103 | 122 | 120 | 123 | 103 | 99 | 108 |

TABLE 45-continued

Dry weight, leaf area and internode length effects of construct M075

| Construction group/line | Wood | Bark | Total: Wood + Bark | 5 fully developed leaves | Remaining leaves | Total: Leaves | Total: Shoot | Leaf area | Specific Leaf Area | Internode Length |
|---|---|---|---|---|---|---|---|---|---|---|
| M075-2B | 100 | 99 | 100 | 96 | 89 | 90 | 94 | 97 | 100 | 104 |
| M075-7 | 110 | 109 | 110 | 101 | 99 | 99 | 104 | 96 | 95 | 99 |

Construct Group M075rp1

Construct group M075rp1 corresponds to transgenic poplar plants overexpressing gene G287 (SEQ ID NO: 435).

Growth effects on dry weight, leaf area and internode length are presented in Table 46. For each parameter, the construct group average and construct group line averages are expressed as a percentage of corresponding wild type group average.

Construct Group M046

Construct group M046 corresponds to transgenic poplar plants overexpressing gene G748 (SEQ ID NO: 513). This construct induced increased growth. The average final height of the construct group was 14% higher than that of the wild type control group. The maximum height growth rate of the construct group was 17% higher than that of the wild type control group. The diameter growth rate of the con-

TABLE 46

Dry weight, leaf area and internode length effects of construct M075rp1

| Construction group/line | Wood | Bark | Total: Wood + Bark | 5 fully developed leaves | Remaining leaves | Total: Leaves | Total: Shoot | Leaf area | Specific Leaf Area | Internode Length | Root | Total: Shoot + root | Root/ Shoot |
|---|---|---|---|---|---|---|---|---|---|---|---|---|---|
| M075rp1 average | 143 | 139 | 142 | 117 | 131 | 129 | 134 | 107 | 91 | 99 | 132 | 134 | 97 |
| M075rp1-1B | 172 | 166 | 170 | 109 | 156 | 150 | 158 | 100 | 92 | 101 | 166 | 160 | 104 |
| M075rp1-2B | 194 | 187 | 192 | 120 | 162 | 157 | 171 | 106 | 88 | 90 | 180 | 173 | 105 |
| M075rp1-3B | 87 | 87 | 87 | 103 | 100 | 100 | 95 | 104 | 100 | 98 | 93 | 94 | 98 |
| M075rp1-5B | 148 | 140 | 145 | 134 | 133 | 133 | 138 | 121 | 90 | 102 | 128 | 136 | 93 |
| M075rp1-7 | 114 | 115 | 114 | 118 | 104 | 106 | 109 | 104 | 88 | 105 | 94 | 106 | 84 |

Construct group M075rp1 showed a significant increase in dry weight "Wood" according to t-test (p=0.001)

Construct group M075rp1 showed a significant increase in dry weight "Bark" according to t-test (p=0.0010)

Construct group M075rp1 showed a significant increase in dry weight "Total: Wood+Bark" according to t-test (p=0.00093)

Construct group M075rp1 showed a significant increase in dry weight "5 fully developed leaves" according to t-test (p=0.011)

Construct group M075rp1 showed a significant increase in dry weight "Remaining leaves" according to t-test (p=0.0018)

Construct group M075rp1 showed a significant increase in dry weight "Total:Leaves" according to t-test (p=0.0016)

Construct group M075rp1 showed a significant increase in dry weight "Total:Shoot" according to t-test (p=0.0011)

Construct group M075rp1 showed a significant increase in dry weight "Total:Shoot including root" according to t-test (p=0.0013)

Construct group M075rp1 showed a significant increase in dry weight "Root" according to t-test (p=0.0051)

Construct group lines M075rp1-1B and M075rp1-2B had significantly increased dry weight; "Wood", "Bark", "Total: Wood+Bark", "Remaining leaves", "Total:Leaves", "Total: Shoot", "Total:Shoot including root" and "Root", with line averages outside of the 95% confidence intervals around wild type.

Construct group line M075rp1-5B had significant increased dry weight; "Wood" and "Total: Wood+Bark", with a line average outside of the 95% confidence intervals around wild type.

struct group was 13% higher than that of the wild type control group. The M046 construct group meets growth criterion (1).

Tables 47 and 48. contain growth data for the specified construct group and corresponding wild type group. Table rows contain height and diameter measurements of individuals of the specified construct group and corresponding wild type group. Time of measurement as number of days in greenhouse is shown in the table headers.

TABLE 47

Height growth data (cm) for M046

| | Days in Greenhouse | | | | | | |
|---|---|---|---|---|---|---|---|
| Individual | 23 | 28 | 32 | 35 | 42 | 51 | 63 |
| M046-3A-1 | N/A | 29 | 40 | 47 | 70 | 115 | 148 |
| M046-3A-2 | 28 | 38 | 47 | 54 | 77 | 111 | 134 |
| M046-3A-3 | 13 | 22 | 30 | 37 | 59 | 91 | N/A |
| M046-3B-1 | 22 | 32 | 42 | 52 | 76 | 116 | 147 |
| M046-3B-2 | 19 | 27 | 38 | 44 | 67 | 107 | 134 |
| M046-3B-3 | N/A | N/A | N/A | N/A | N/A | N/A | N/A |
| M046-5B-1 | 21 | 29 | 35 | 41 | 58 | 95 | 125 |
| M046-5B-2 | N/A | 29 | N/A | N/A | N/A | N/A | N/A |
| M046-5B-3 | N/A | 31 | 40 | 48 | 71 | 106 | 141 |
| T89-20 | N/A | N/A | N/A | N/A | N/A | N/A | N/A |
| T89-21 | 18 | 26 | 34 | 38 | 57 | 85 | 106 |
| T89-22 | 19 | 28 | 36 | 42 | 63 | 97 | 126 |
| T89-23 | 21 | 30 | 40 | 46 | 65 | 87 | 108 |
| T89-24 | N/A | 29 | 34 | 39 | 55 | 83 | 105 |
| T89-25 | 21 | 29 | 38 | 44 | 61 | 90 | 120 |
| T89-26 | N/A | 24 | 34 | 37 | 59 | 83 | 117 |
| T89-27 | N/A | N/A | 31 | 37 | 56 | 91 | 123 |
| T89-28 | N/A | 28 | N/A | 42 | 63 | 101 | 135 |
| T89-29 | N/A | 32 | 40 | 46 | 66 | 103 | 134 |
| T89-30 | 23 | 33 | 40 | 48 | 69 | 109 | 133 |

TABLE 47-continued

Height growth data (cm) for M046

| Individual | \multicolumn{7}{c}{Days in Greenhouse} |
|---|---|---|---|---|---|---|---|
| | 23 | 28 | 32 | 35 | 42 | 51 | 63 |
| T89-31 | 23 | 32 | 40 | 46 | 68 | 101 | 129 |
| T89-32 | 19 | 31 | 39 | 45 | 63 | 93 | 120 |
| T89-33 | 21 | 31 | 38 | 42 | 58 | 81 | 103 |
| T89-34 | 19 | 27 | 32 | 38 | 56 | 83 | 108 |
| T89-35 | N/A | 23 | 30 | 35 | 53 | 87 | 119 |
| T89-36 | 16 | 21 | 27 | 33 | 51 | 86 | 114 |
| T89-37 | N/A | 23 | 28 | 35 | 56 | 89 | 117 |
| T89-38 | N/A | 32 | 41 | 47 | 67 | 102 | 138 |
| T89-39 | 24 | 34 | 43 | 48 | N/A | 103 | 125 |
| T89-40 | 21 | 29 | 36 | 43 | 61 | 88 | 112 |
| T89-41 | 17 | 24 | 31 | 38 | 55 | 83 | 115 |
| T89-42 | 23 | 31 | 40 | 44 | 60 | 84 | 117 |
| T89-43 | 19 | 26 | 32 | 35 | 53 | 84 | 117 |
| T89-44 | 19 | 29 | 36 | 43 | 62 | 94 | 125 |
| T89-45 | 20 | 26 | 34 | 39 | 57 | 92 | 124 |
| T89-46 | N/A | 28 | 36 | 44 | 64 | 95 | 126 |

TABLE 48

Diameter growth data (mm) for M046

| Individual | Days in Greenhouse | | |
|---|---|---|---|
| | 35 | 42 | 63 |
| M046-3A-1 | 4.3 | 5.5 | 8.9 |
| M046-3A-2 | 4.6 | 6.0 | 8.7 |
| M046-3A-3 | 3.8 | 5.0 | N/A |
| M046-3B-1 | 4.6 | 5.6 | 9.6 |
| M046-3B-2 | 4 | 7.1 | 8.6 |
| M046-3B-3 | N/A | N/A | N/A |
| M046-5B-1 | N/A | N/A | 9 |
| M046-5B-2 | N/A | N/A | N/A |
| M046-5B-3 | N/A | 5.6 | 8.5 |
| T89-20 | N/A | N/A | N/A |
| T89-21 | 3.4 | 4.7 | 5.7 |
| T89-22 | 4.2 | 5.7 | 9.2 |
| T89-23 | 4.2 | 5.4 | 6.3 |
| T89-24 | 3.2 | 6.3 | 8.5 |
| T89-25 | 4.3 | N/A | 8.3 |
| T89-26 | N/A | 5.1 | 8.7 |
| T89-27 | N/A | 5.4 | 8.8 |
| T89-28 | N/A | 5.4 | 9.6 |
| T89-29 | 4.8 | 5.2 | 8.2 |
| T89-30 | 4.6 | 5.9 | 8.1 |
| T89-31 | 4.6 | 6.2 | 9.1 |
| T89-32 | 4.4 | 5.7 | 9.6 |
| T89-33 | 3.6 | N/A | 6.5 |
| T89-34 | 3 | 5.1 | 7.8 |
| T89-35 | N/A | N/A | 8.1 |
| T89-36 | N/A | 5.1 | 7.8 |
| T89-37 | N/A | 5.7 | 7.2 |
| T89-38 | 5.5 | 5.9 | 9.4 |
| T89-39 | 4.6 | 5.8 | 7.0 |
| T89-40 | 4.0 | 5.3 | 6.5 |
| T89-41 | 3.8 | 5.9 | 8.1 |
| T89-42 | 3.8 | 5.5 | 8.2 |
| T89-43 | N/A | N/A | 7.7 |
| T89-44 | N/A | N/A | 9.2 |
| T89-45 | N/A | 6.2 | 8.1 |
| T89-46 | N/A | 5.6 | 8.9 |

Results from growth analysis are summarized in the overview Table 49. The determined growth effects of the specified construct group are presented as ratios between construct and wild type group for AFH, AFD, AMHGR, ADGR, MFH, MFD, MMHGR and MDC.

TABLE 49

Overview table of growth effects of construct M046

| Construct group | Average Final Height | Average Final Diameter | Average Maximum Height Growth Rate | Average Diameter Growth Rate | Maximum Final Height | Maximum Final Diameter | Maximum of maximum Height Growth Rate | Maximum Diameter Growth Rate |
|---|---|---|---|---|---|---|---|---|
| M046 | 1.14 | 1.06 | 1.17 | 1.13 | 1.07 | 0.92 | 1.09 | 0.86 |

Construct Group M046rp1

Construct group M046rp1 corresponds to transgenic poplar plants overexpressing gene G748 (SEQ ID NO: 513).

Growth effects on dry weight, leaf area and internode length are presented in Table 50. For each parameter, the construct group average and construct group line averages are expressed as a percentage of corresponding wild type group average.

TABLE 50

Dry weight, leaf area and internode length effects of construct M046rp1

| Construction group/line | Wood | Bark | Total: Wood + Bark | 5 fully developed leaves | Remaining leaves | Total: Leaves | Total: Shoot | Leaf area | Specific Leaf Area | Internode Length | Root | Total: Shoot + root | Root/Shoot |
|---|---|---|---|---|---|---|---|---|---|---|---|---|---|
| M046rp1 | 110 | 102 | 107 | 104 | 107 | 107 | 107 | 104 | 99 | 101 | 101 | 106 | 93 |
| M046rp1-1A | 125 | 117 | 123 | 107 | 121 | 119 | 120 | 109 | 102 | 100 | 125 | 121 | 103 |
| M046rp1-3A | 128 | 118 | 125 | 123 | 130 | 129 | 127 | 116 | 93 | 105 | 119 | 126 | 92 |
| M046rp1-3B | 129 | 117 | 125 | 109 | 114 | 113 | 118 | 104 | 95 | 102 | 110 | 117 | 92 |

TABLE 50-continued

Dry weight, leaf area and internode length effects of construct M046rp1

| Construction group/line | Wood | Bark | Total: Wood + Bark | 5 fully developed leaves | Remaining leaves | Total: Leaves | Total: Shoot | Leaf area | Specific Leaf Area | Internode Length | Root | Total: Shoot + root | Root/Shoot |
|---|---|---|---|---|---|---|---|---|---|---|---|---|---|
| M046rp1-4B | 85 | 80 | 84 | 95 | 89 | 90 | 87 | 101 | 105 | 102 | 75 | 85 | 86 |
| M046rp1-5B | 82 | 77 | 80 | 88 | 82 | 82 | 82 | 88 | 99 | 97 | 77 | 81 | 93 |

TABLE 51

Density M046rp1

| Individual | Density (g/cm3) |
|---|---|
| M046rp1-1A-2 | 0.288 |
| M046rp1-3A-3 | 0.295 |
| M046rp1-3B-2 | 0.309 |
| M046rp1-4B-3 | 0.299 |
| M046rp1-5B-2 | 0.314 |
| T89-02 | 0.270 |
| T89-04 | 0.278 |
| T89-05 | 0.272 |
| T89-10 | 0.261 |
| T89-17 | 0.272 |
| T89-19 | 0.275 |
| T89-21 | 0.274 |
| T89-25 | 0.262 |
| T89-27 | 0.266 |
| T89-30 | 0.277 |
| T89-36 | 0.252 |
| T89-37 | 0.289 |
| T89-41 | 0.281 |
| T89-42 | 0.280 |

Construct group M046pr1 had increased wood density, on average 10.6% higher density than wild type. This is a significant change according to t-test (p=0.000031). 4 out of the 5 samples in construct group M046rp1 had wood density values outside the 95% confidence interval around wild type.

Construct Group M046rp2

In a replant, the M046rp2 construct group once again showed increased growth, with statistically significantly increased growth height (+3.5%) and statistically significantly increased wood density (9%) compared to WT. Line M046rp2-3A had statistically significantly increased growth height (+6%), increased stem volume (+21%) and increased total shoot dry weight (+14%). All lines showed increased wood density i.e. M046rp2-1A (+7%), M046rp2-3A (+12%) and M046rp2-3B (6%) but these results were not statistically significant on line basis according to a t-test.

Construct Group M096

Construct group M096 corresponds to transgenic poplar plants overexpressing gene G878 (SEQ ID NO: 605). This construct induced increased growth. The average final height of the construct group was 21% higher than that of the wild type control group. The maximum height growth rate of the construct group was 25% higher than that of the wild type control group. The M096 construct group meets the more stringent level of growth difference selection criteria (1) and (3) and the less stringent level of growth criterion (4).

Tables 52 and 53 contain growth data for the specified construct group and corresponding wild type group. Table rows contain height and diameter measurements of individuals of the specified construct group and corresponding wild type group. Time of measurement as number of days in greenhouse is shown in the table headers.

TABLE 52

Height growth data (cm) for M096

| Individual | Days in Greenhouse | | | | | |
|---|---|---|---|---|---|---|
| | 20 | 27 | 34 | 41 | 48 | 55 |
| M096-1B-1 | 25 | 41 | 63 | 86 | 114 | 138 |
| M096-1B-2 | 19 | 30 | 47 | 66 | 84 | 108 |
| M096-1B-3 | 23 | 40 | 64 | 89 | 113 | 136 |
| M096-3A-1 | 23 | 38 | 57 | 79 | 104 | 127 |
| M096-3A-2 | 23 | 37 | 57 | 84 | 112 | 135 |
| M096-3A-3 | 25 | 39 | 60 | 82 | 109 | 131 |
| M096-3B-1 | 22 | 31 | 47 | 69 | N/A | 111 |
| M096-3B-2 | 21 | 38 | 58 | 81 | 104 | 126 |
| M096-3B-3 | 25 | 37 | 54 | 76 | 98 | 122 |
| T89-31 | N/A | 33 | 46 | 64 | 80 | 101 |
| T89-32 | 22 | 32 | 45 | 62 | 83 | 102 |
| T89-33 | 22 | 31 | 47 | 70 | 92 | 113 |
| T89-34 | 19 | 33 | 48 | 67 | 84 | 106 |
| T89-35 | 21 | 35 | 51 | 72 | 92 | 113 |
| T89-36 | 24 | 35 | 49 | 67 | 83 | 103 |
| T89-37 | 22 | 32 | 47 | 63 | 80 | 100 |
| T89-38 | 23 | 29 | 41 | 57 | N/A | 89 |
| T89-39 | 22 | 31 | 49 | 69 | 85 | 102 |
| T89-40 | 21 | 30 | 45 | 61 | 79 | 98 |
| T89-41 | 25 | 36 | 52 | 69 | 83 | 108 |
| T89-42 | 22 | 32 | 48 | 69 | 87 | 109 |
| T89-43 | 19 | 28 | 43 | 62 | 81 | 100 |

TABLE 53

Diameter growth data (mm) for M096

| Individual | Days in Greenhouse | | |
|---|---|---|---|
| | 34 | 41 | 55 |
| M096-1B-1 | 5.3 | 7.1 | 9.3 |
| M096-1B-2 | 4.0 | 5.1 | 7.2 |
| M096-1B-3 | 4.9 | 6.5 | 9.4 |
| M096-3A-1 | 3.7 | 6.0 | 9.0 |
| M096-3A-2 | 4.2 | 6.0 | 9.3 |
| M096-3A-3 | 4.9 | 6.9 | 9.6 |
| M096-3B-1 | 3.5 | 5.3 | 8.4 |
| M096-3B-2 | 4.9 | 6.6 | 8.0 |
| M096-3B-3 | 4.1 | 6.0 | 8.5 |
| T89-31 | 4.1 | 5.5 | 8.6 |
| T89-32 | 4.2 | 6.2 | 8.7 |
| T89-33 | 4.3 | 5.8 | 8.2 |
| T89-34 | 4.1 | 6.5 | 7.9 |
| T89-35 | 4.3 | 5.8 | 8.4 |
| T89-36 | 4.0 | 5.3 | 7.7 |
| T89-37 | 4.1 | 6.2 | 8.0 |
| T89-38 | 4.0 | 5.5 | 7.2 |
| T89-39 | 4.2 | 6.3 | 7.2 |
| T89-40 | 4.1 | 5.8 | 8.5 |
| T89-41 | 4.3 | 6.3 | 8.4 |
| T89-42 | 4.1 | 5.6 | 7.8 |
| T89-43 | 3.8 | 5.3 | 6.9 |

Results from the growth analysis are summarized in the overview Table 54. The determined growth effects of the specified construct group are presented as ratios between construct and wild type group for AFH, AFD, AMHGR, ADGR, MFH, MFD, MMHGR and MDC.

TABLE 54

Overview table of growth effects of construct M096

| Construct group | Average Final Height | Average Final Diameter | Average Maximum Height Growth Rate | Average Diameter Growth Rate | Maximum Final Height | Maximum Final Diameter | Maximum of Maximum Height Growth Rate | Maximum Diameter Growth Rate |
|---|---|---|---|---|---|---|---|---|
| M096 | 1.21 | 1.09 | 1.25 | 1.12 | 1.14 | 1.01 | 1.19 | 0.97 |

Construct Group M096rp1

Construct group M096rp1 corresponds to transgenic poplar plants overexpressing gene G878 (SEQ ID NO: 605) being replanted in the greenhouse. Again this construct induced increased growth. The average final height of the construct group was 7% greater than that of the wild type control group. The maximum height growth rate of the construct group was 8% higher than that of the wild type control group. The M096rp1 construct group meets growth criterion (1).

Tables 55 and 56 contain growth data for the specified construct group and corresponding wild type group. Table rows contain height and diameter measurements of individuals of the specified construct group and corresponding wild type group. Time of measurement as number of days in greenhouse is shown in the table headers.

TABLE 55

Height growth data (cm) for M096rp1

| | Days in Greenhouse | | | | | | | | |
|---|---|---|---|---|---|---|---|---|---|
| Individual | 19 | 22 | 26 | 29 | 33 | 36 | 44 | 48 | 54 |
| M096rp1-1A-1 | 28 | 33 | 46 | 58 | 75 | 87 | 119 | 134 | 152 |
| M096rp1-1A-2 | 23 | 27 | 35 | 45 | 58 | N/A | 102 | 115 | 137 |
| M096rp1-1A-3 | 24 | 27 | 35 | 44 | 54 | 65 | 95 | 106 | 119 |
| M096rp1-1B-1 | 29 | 36 | 46 | 61 | 79 | 93 | 128 | 140 | 159 |
| M096rp1-1B-2 | 30 | 36 | 48 | 60 | 78 | 91 | 126 | 137 | 159 |
| M096rp1-1B-3 | 24 | 29 | 38 | 48 | 63 | 74 | 109 | 121 | 141 |
| M096rp1-2B-1 | 25 | 30 | 38 | 48 | 61 | 72 | 104 | 116 | 138 |
| M096rp1-2B-2 | 21 | 25 | 31 | 42 | 55 | 66 | 96 | 103 | 128 |
| M096rp1-2B-3 | 29 | 35 | 46 | 58 | 77 | 93 | 126 | 140 | 161 |
| M096rp1-3A-1 | 23 | 27 | 36 | 47 | 63 | 76 | 109 | 125 | 142 |
| M096rp1-3A-2 | 24 | 28 | 38 | 50 | 65 | 79 | 110 | 122 | 145 |
| M096rp1-3A-3 | 25 | 31 | 40 | 53 | 68 | 78 | 105 | 115 | 129 |
| M096rp1-3B-1 | 23 | 27 | 37 | 50 | 66 | 80 | 114 | 131 | 149 |
| M096rp1-3B-2 | 25 | 30 | 36 | 49 | 64 | 77 | 113 | N/A | 153 |
| M096rp1-3B-3 | 24 | 28 | 36 | 45 | 62 | 74 | 107 | 122 | 143 |
| T89-01 | 26 | 31 | 40 | 49 | 63 | 75 | 106 | 121 | 147 |
| T89-02 | 24 | 31 | 39 | 51 | 65 | 76 | 108 | 120 | 140 |
| T89-03 | 25 | 30 | 38 | 49 | 66 | 78 | 111 | 122 | 138 |
| T89-04 | 24 | 29 | 36 | 46 | 61 | 74 | 103 | 115 | 135 |
| T89-05 | 22 | 25 | 33 | 41 | 55 | 67 | 99 | 113 | 133 |
| T89-06 | 24 | 28 | 36 | 48 | 64 | 76 | 111 | 128 | 143 |
| T89-07 | 24 | 32 | 40 | 53 | 71 | 84 | 119 | 137 | 153 |
| T89-08 | 22 | 27 | 36 | 47 | 62 | 72 | 101 | 114 | 133 |
| T89-09 | 22 | 26 | 34 | 44 | 57 | 67 | 97 | 108 | 131 |
| T89-10 | 23 | 28 | 35 | 45 | 56 | 70 | 96 | 107 | 126 |
| T89-11 | 22 | 28 | 37 | 47 | 63 | 76 | 106 | 120 | 139 |
| T89-12 | 23 | 28 | 36 | 45 | 58 | 67 | 94 | 106 | 120 |
| T89-13 | 27 | 31 | 40 | 49 | 61 | 71 | 102 | 114 | 132 |
| T89-14 | 23 | 28 | 37 | 46 | 59 | 70 | 101 | 114 | 133 |
| T89-15 | 25 | 30 | 39 | 51 | 67 | 78 | 106 | 122 | 140 |
| T89-16 | 23 | 26 | 35 | 44 | 56 | 67 | 100 | 112 | 136 |
| T89-17 | 22 | 25 | 34 | 44 | 57 | 70 | 102 | 115 | 136 |
| T89-18 | 21 | 26 | 34 | 43 | 57 | 69 | 100 | 113 | 134 |
| T89-19 | 23 | 28 | 37 | 46 | 61 | 73 | 105 | 120 | 139 |
| T89-20 | 24 | 29 | 40 | 50 | 66 | 79 | 113 | 126 | 144 |
| T89-21 | 26 | 33 | 41 | 53 | 70 | 81 | 114 | 133 | 149 |
| T89-22 | 23 | 28 | 36 | 46 | 60 | 71 | 101 | 116 | 136 |
| T89-23 | 23 | 29 | 35 | 46 | 60 | 71 | 100 | 115 | 135 |
| T89-24 | 23 | 27 | 35 | 44 | 55 | 62 | 84 | 92 | 102 |
| T89-25 | 22 | 26 | 33 | 41 | 55 | 66 | 95 | 107 | 128 |
| T89-26 | 25 | 28 | 37 | 46 | 59 | 70 | 100 | 117 | 135 |
| T89-27 | 24 | 30 | 38 | 47 | 63 | 71 | 102 | 115 | 133 |
| T89-28 | 21 | 27 | 33 | 43 | 55 | 67 | 96 | 114 | 127 |
| T89-29 | 23 | 27 | 35 | 44 | 57 | 68 | 97 | 109 | 129 |
| T89-30 | 24 | 28 | 37 | 49 | 64 | 76 | 109 | 120 | 137 |
| T89-31 | 22 | 25 | 33 | 42 | 57 | 65 | 97 | 105 | 128 |

TABLE 55-continued

Height growth data (cm) for M096rp1

| Individual | Days in Greenhouse | | | | | | | | |
|---|---|---|---|---|---|---|---|---|---|
| | 19 | 22 | 26 | 29 | 33 | 36 | 44 | 48 | 54 |
| T89-32 | 23 | 28 | 36 | 48 | 62 | 76 | 107 | 120 | 140 |
| T89-33 | 24 | 28 | 37 | 47 | 59 | 71 | 104 | 117 | 138 |
| T89-34 | N/A | N/A | N/A | N/A | N/A | N/A | N/A | N/A | N/A |
| T89-35 | 23 | 29 | 36 | 47 | 63 | 76 | 107 | 123 | 141 |
| T89-36 | 21 | 25 | 33 | 42 | 56 | 69 | 97 | 113 | 131 |
| T89-37 | 25 | 28 | 35 | 45 | 61 | 72 | 104 | 117 | 135 |
| T89-38 | 23 | 28 | 35 | 45 | 60 | 72 | 100 | 113 | 133 |
| T89-39 | 26 | 29 | 38 | 48 | 63 | 75 | 105 | 117 | 136 |
| T89-40 | 23 | 28 | 37 | 47 | 56 | 68 | 98 | 110 | 130 |
| T89-41 | 27 | 31 | 40 | 51 | 66 | 81 | 113 | N/A | 142 |
| T89-42 | 21 | 25 | 33 | 41 | 51 | 63 | 91 | 102 | 116 |

TABLE 56

Diameter growth data (mm) for M096rp1

| Individual | Days in Greenhouse | | |
|---|---|---|---|
| | 35 | 42 | 63 |
| M096rp1-1A-1 | 3.5 | 5.0 | 7.3 |
| M096rp1-1A-2 | 2.8 | 4.0 | 6.6 |
| M096rp1-1A-3 | 2.6 | 3.8 | 8.4 |
| M096rp1-1B-1 | 3.7 | 4.9 | 7.8 |
| M096rp1-1B-2 | 4.2 | 4.6 | 8.0 |
| M096rp1-1B-3 | 3.2 | 4.4 | 8.5 |
| M096rp1-2B-1 | 3.2 | 4.2 | 7.0 |
| M096rp1-2B-2 | 3.0 | 3.9 | 7.2 |
| M096rp1-2B-3 | 4.0 | 5.1 | 8.6 |
| M096rp1-3A-1 | 3.4 | 4.4 | 8.3 |
| M096rp1-3A-2 | 3.4 | 4.3 | 7.7 |
| M096rp1-3A-3 | 3.1 | 5.3 | 6.7 |
| M096rp1-3B-1 | 3.1 | 4.3 | 8.1 |
| M096rp1-3B-2 | 3.2 | 3.6 | 7.5 |
| M096rp1-3B-3 | 2.9 | 6.9 | 6.6 |
| T89-01 | 3.4 | 4.5 | 7.2 |
| T89-02 | 3.4 | 4.8 | 8.6 |
| T89-03 | 3.6 | 4.9 | 7.7 |
| T89-04 | 3.0 | 4.3 | 7.0 |
| T89-05 | 3.3 | 4.2 | 7.6 |
| T89-06 | 3.0 | 4.6 | 8.9 |
| T89-07 | 3.4 | 5.2 | 9.0 |
| T89-08 | 2.9 | 4.8 | 7.5 |
| T89-09 | 3.2 | 4.4 | 7.0 |
| T89-10 | 3.2 | 4.3 | 7.1 |
| T89-11 | 3.7 | 5.6 | 6.1 |
| T89-12 | 3.0 | 3.9 | 6.3 |
| T89-13 | 3.1 | 4.6 | 7.7 |
| T89-14 | 3.1 | 4.3 | 8.9 |
| T89-15 | 3.4 | 4.9 | 10.3 |
| T89-16 | 2.9 | 4.2 | 7.0 |
| T89-17 | 3.0 | 4.8 | 8.2 |
| T89-18 | 3.2 | 4.6 | 7.5 |
| T89-19 | 3.2 | 4.6 | 8.6 |
| T89-20 | 3.3 | 4.1 | 7.5 |
| T89-21 | 4.1 | 5.0 | 9.5 |
| T89-22 | 3.2 | 5.0 | 8.4 |
| T89-23 | 3.0 | 4.2 | 7.2 |
| T89-24 | 3.4 | 3.7 | 6.3 |
| T89-25 | 2.7 | 3.9 | 7.3 |
| T89-26 | 3.2 | 5.0 | 6.9 |
| T89-27 | 3.0 | 4.0 | 7.1 |
| T89-28 | 2.9 | 4.3 | 8.9 |
| T89-29 | 3.3 | 4.7 | 9.1 |
| T89-30 | 3.1 | 4.3 | 6.6 |
| T89-31 | 2.8 | 4.2 | 7.0 |
| T89-32 | 3.1 | 4.8 | 8.0 |
| T89-33 | 3.1 | 4.7 | 6.8 |
| T89-34 | N/A | N/A | N/A |
| T89-35 | 3.3 | 4.9 | 8.5 |
| T89-36 | 3.1 | 4.0 | 8.7 |
| T89-37 | 2.7 | 4.0 | 6.4 |
| T89-38 | 3.0 | 4.5 | 7.4 |
| T89-39 | 2.9 | 4.0 | 7.2 |
| T89-40 | 3.3 | 4.3 | 6.8 |
| T89-41 | 3.6 | 5.2 | 9.0 |
| T89-42 | 2.6 | 3.9 | 5.6 |

Results from growth analysis are summarized in the overview Table 57. The determined growth effects of the specified construct group are presented as ratios between construct and wild type group for AFH, AFD, AMHGR, ADGR, MFH, MFD, MMHGR and MDC.

TABLE 57

Overview table of growth effects of construct M096rp1

| Construct group | Average Final Height | Average Final Diameter | Average Maximum Height Growth Rate | Average Diameter Growth Rate | Maximum Final Height | Maximum Final Diameter | Maximum of maxumim Height Growth Rate | Maximum Diameter Growth Rate |
|---|---|---|---|---|---|---|---|---|
| M096rp1 | 1.07 | 0.99 | 1.08 | 0.96 | 1.05 | 0.83 | 1.07 | 0.84 |

Growth effects on dry weight, leaf area and internode length are presented in Table 58. For each parameter, the construct group average and construct group line averages are expressed as a percentage of corresponding wild type group average.

TABLE 58

Dry weight, leaf area and internode length effects of construct M096rp1

| Construction group/line | Wood | Bark | Total: Wood + Bark | 5 fully developed leaves | Remaining leaves | Total: Leaves | Total: Shoot | Leaf area | Specific Leaf Area | Internode Length | Root | Total: Shoot + root | Root/Shoot |
|---|---|---|---|---|---|---|---|---|---|---|---|---|---|
| M096rp1 | 111 | 107 | 110 | 106 | 96 | 98 | 103 | 102 | 96 | 108 | 97 | 102 | 95 |
| M096rp1-1A | 96 | 96 | 96 | 98 | 81 | 83 | 89 | 91 | 92 | 115 | 87 | 88 | 92 |
| M096rp1-1B | 137 | 127 | 134 | 131 | 119 | 120 | 126 | 123 | 94 | 110 | 118 | 124 | 94 |
| M096rp1-2B | 113 | 104 | 110 | 113 | 104 | 105 | 107 | 104 | 92 | 105 | 86 | 103 | 80 |
| M096rp1-3A | 93 | 99 | 95 | 86 | 80 | 81 | 87 | 80 | 92 | 102 | 105 | 90 | 124 |
| M096rp1-3B | 113 | 111 | 113 | 104 | 98 | 99 | 104 | 113 | 109 | 108 | 90 | 102 | 85 |

Construct group M096rp1 showed a significantly increased "Internode Length" according to a t-test (p=0.0050)

Construct group line M096rp1-1A showed a significantly increased "Internode Length", based on the line average, which is outside 95% confidence intervals around wild type.

TABLE 59

Density M096rp1

| Individual | Density (g/cm3) |
|---|---|
| M096rp1-1A-2 | 0.309 |
| M096rp1-1B-2 | 0.293 |
| M096rp1-2B-1 | 0.288 |
| M096rp1-3A-1 | 0.273 |
| M096rp1-3B-1 | 0.267 |
| T89-02 | 0.270 |
| T89-04 | 0.278 |
| T89-05 | 0.272 |
| T89-10 | 0.261 |
| T89-17 | 0.272 |
| T89-19 | 0.275 |
| T89-21 | 0.274 |
| T89-25 | 0.262 |
| T89-27 | 0.266 |
| T89-30 | 0.277 |
| T89-36 | 0.252 |
| T89-37 | 0.289 |
| T89-41 | 0.281 |
| T89-42 | 0.280 |

Construct group M096rp 1 had increased wood density, on average 5.1% higher density than wild type. This is a significant change according to a t-test (p=0.037). 1 sample out of 5 in the construct group M096rp1 showed wood density values outside a 95% confidence interval around wild type.

Example III

Transformation of Eudicots for Greater Biomass, or Abiotic Stress Tolerance

Crop species including soybean plants, tomato plants, and forestry crops such as poplar or *eucalyptus* that overexpress any of a considerable number of the disclosed transcription factor polypeptides may produce plants with increased drought tolerance and/or biomass or other desirable traits. Such genes, when overexpressed, will result in improved quality and larger yields than non-transformed plants in non-stressed or stressed conditions; the latter may occur in the field to even a low, imperceptible degree at any time in the growing season.

Thus, transcription factor polynucleotide sequences listed in the Sequence Listing recombined into, for example, one of the disclosed expression vectors, or another suitable expression vector, may be transformed into a plant for the purpose of modifying plant traits for the purpose of improving yield and/or quality. The expression vector may contain a constitutive, tissue-enhanced or inducible promoter operably linked to the transcription factor polynucleotide. The cloning vector may be introduced into a variety of plants by means well known in the art such as, for example, direct DNA transfer or *Agrobacterium tumefaciens*-mediated transformation. It is now routine to produce transgenic plants using most eudicot plants (see Weissbach and Weissbach, (1989); Gelvin et al. (1990); Herrera-Estrella et al. (1983); Bevan (1984); and Klee (1985)). Methods for analysis of traits are routine in the art and examples are disclosed above.

Numerous protocols for the transformation of tomato, soy plants and Poplar have been previously described, and are well known in the art. Gruber et al. (1993), and Glick and Thompson (1993) describe several expression vectors and culture methods that may be used for cell or tissue transformation and subsequent regeneration. For soybean transformation, methods are described by Miki et al. (1993); and U.S. Pat. No. 5,563,055, (Townsend and Thomas), issued Oct. 8, 1996. For Poplar transformation, methods are described by Nilsson et al. (1992).

There are a substantial number of alternatives to *Agrobacterium*-mediated transformation protocols. One such method is microprojectile-mediated transformation, in which DNA on the surface of microprojectile particles is driven into plant tissues with a biolistic device (see, for example, Sanford et al. (1987); Christou et al. (1992); Sanford (1993); Klein et al. (1987); U.S. Pat. No. 5,015,580 (Christou et al), issued May 14, 1991; and U.S. Pat. No. 5,322,783 (Tomes et al.), issued Jun. 21, 1994).

Alternatively, sonication methods (see, for example, Zhang et al. (1991)); direct uptake of DNA into protoplasts using $CaCl_2$ precipitation, polyvinyl alcohol or poly-L-ornithine (Hain et al. (1985); Draper et al. (1982)); liposome or spheroplast fusion (see, for example, Deshayes et al. (1985); Christou et al. (1987)); and electroporation of protoplasts and whole cells and tissues (see, for example, Donn et al. (1990); D'Halluin et al. (1992); and Spencer et al. (1994)) have been used to introduce foreign DNA and expression vectors into plants.

After a plant or plant cell is transformed (and the latter regenerated into a plant), the transformed plant may be crossed with itself or a plant from the same line, a non-transformed or wild-type plant, or another transformed plant from a different transgenic line of plants. Crossing provides the advantages of producing new and often stable transgenic varieties. Genes and the traits they confer that have been introduced into a tomato or soybean line may be moved into distinct line of plants using traditional backcrossing techniques well known in the art.

Transformation of soybean plants may be conducted using the methods found in, for example, U.S. Pat. No. 5,563,055 (Townsend et al., issued Oct. 8, 1996), described in brief here. In this method soybean seed is surface sterilized by exposure to chlorine gas evolved in a glass bell jar. Seeds are germinated by plating on 1/10 strength agar solidified medium without plant growth regulators and culturing at 28° C. with a 16 hour day length. After three or four days, seed may be prepared for cocultivation. The seedcoat is removed and the elongating radicle removed 3-4 mm below the cotyledons.

Overnight cultures of *Agrobacterium tumefaciens* harboring the expression vector comprising a disclosed polynucleotide are grown to log phase, pooled, and concentrated by centrifugation. Inoculations are conducted in batches such that each plate of seed is treated with a newly resuspended pellet of *Agrobacterium*. The pellets are resuspended in 20 ml inoculation medium. The inoculum is poured into a Petri dish containing prepared seed and the cotyledonary nodes are macerated with a surgical blade. After 30 minutes the explants are transferred to plates of the same medium that has been solidified. Explants are embedded with the adaxial side up and level with the surface of the medium and cultured at 22° C. for three days under white fluorescent light. These plants may then be regenerated according to methods well established in the art, such as by moving the explants after three days to a liquid counter-selection medium (see U.S. Pat. No. 5,563,055).

The explants may then be picked, embedded and cultured in solidified selection medium. After one month on selective media transformed tissue becomes visible as green sectors of regenerating tissue against a background of bleached, less healthy tissue. Explants with green sectors are transferred to an elongation medium. Culture is continued on this medium with transfers to fresh plates every two weeks. When shoots are 0.5 cm in length they may be excised at the base and placed in a rooting medium.

Example XIV

Transformation of Monocots for Greater Biomass, or Abiotic Stress Tolerance

Cereal plants such as, but not limited to, corn, wheat, rice, sorghum, barley, switchgrass or *Miscanthus* may be transformed with the present polynucleotide sequences, including monocot or eudicot-derived sequences such as those presented in the present Tables, cloned into a vector such as pGA643 and containing a kanamycin-resistance marker, and expressed constitutively under, for example, the CaMV 35S or COR15 promoters, or with tissue-enhanced or inducible promoters. The expression vectors may be one found in the Sequence Listing, or any other suitable expression vector may be similarly used. For example, pMEN020 may be modified to replace the NptII coding region with the BAR gene of *Streptomyces hygroscopicus* that confers resistance to phosphinothricin. The KpnI and BglII sites of the Bar gene are removed by site-directed mutagenesis with silent codon changes.

The cloning vector may be introduced into a variety of cereal plants by means well known in the art including direct DNA transfer or *Agrobacterium tumefaciens*-mediated transformation. The latter approach may be accomplished by a variety of means, including, for example, that of U.S. Pat. No. 5,591,616, in which monocotyledon callus is transformed by contacting dedifferentiating tissue with the *Agrobacterium* containing the cloning vector.

The sample tissues are immersed in a suspension of $3 \times 10^9$ cells of *Agrobacterium* containing the cloning vector for 3-10 minutes. The callus material is cultured on solid medium at 25° C. in the dark for several days. The calli grown on this medium are transferred to Regeneration medium. Transfers are continued every 2-3 weeks (2 or 3 times) until shoots develop. Shoots are then transferred to Shoot-Elongation medium every 2-3 weeks. Healthy looking shoots are transferred to rooting medium and after roots have developed, the plants are placed into moist potting soil.

The transformed plants are then analyzed for the presence of the NPTII gene/kanamycin resistance by ELISA, using the ELISA NPTII kit from 5Prime-3Prime Inc. (Boulder, Colo.).

It is also routine to use other methods to produce transgenic plants of most cereal crops (Vasil (1994)) such as corn, wheat, rice, sorghum (Cassas et al. (1993)), and barley (Wan and Lemeaux (1994)). DNA transfer methods such as the microprojectile method can be used for corn (Fromm et al. (1990); Gordon-Kamm et al. (1990); Ishida (1990)), wheat (Vasil et al. (1992); Vasil et al. (1993); Weeks et al. (1993)), and rice (Christou (1991); Hiei et al. (1994); Aldemita and Hodges (1996); and Hiei et al. (1997)). For most cereal plants, embryogenic cells derived from immature scutellum tissues are the preferred cellular targets for transformation (Hiei et al. (1997); Vasil (1994)). For transforming corn embryogenic cells derived from immature scutellar tissue using microprojectile bombardment, the A188XB73 genotype is the preferred genotype (Fromm et al. (1990); Gordon-Kamm et al. (1990)). After microprojectile bombardment the tissues are selected on phosphinothricin to identify the transgenic embryogenic cells (Gordon-Kamm et al. (1990)). Transgenic plants are regenerated by standard corn regeneration techniques (Fromm et al. (1990); Gordon-Kamm et al. (1990)).

Example XV

Expression and Analysis of Sequences that Confer Significant Improvements to Non-A Rabidopsis Species Northern blot analysis, RT-PCR or microarray analysis of the regenerated, transformed plants may be used to show expression of a disclosed transcription factor polypeptide and related genes that are capable of inducing abiotic stress tolerance, and/or larger size.

To verify the ability to confer stress resistance, mature plants overexpressing a disclosed transcription factor, or alternatively, seedling progeny of these plants, may be challenged by a stress such as a disease pathogen, drought, heat, cold, high salt, or desiccation. Alternatively, these plants may be challenged in a hyperosmotic stress condition that may also measure altered sugar sensing, such as a high sugar condition. By comparing control plants (for example, wild type) and transgenic plants similarly treated, the transgenic plants may be shown to have greater tolerance to the particular stress.

After a eudicot plant, monocot plant or plant cell has been transformed (and the latter regenerated into a plant) and shown to have greater size or tolerance to abiotic stress, or produce greater yield relative to a control plant under the stress conditions, the transformed monocot plant may be crossed with itself or a plant from the same line, a non-transformed or wild-type monocot plant, or another transformed monocot plant from a different transgenic line of plants.

The function of specific disclosed transcription factors have been analyzed and may be further characterized and incorporated into crop plants. The ectopic overexpression of these sequences may be regulated using constitutive, inducible, or tissue specific regulatory elements. Genes that have been examined and have been shown to modify plant traits (including increasing biomass, and/or abiotic stress tolerance) encode transcription factor polypeptides found in the Sequence Listing. In addition to these sequences, it is expected that newly discovered polynucleotide and polypeptide sequences closely related to polynucleotide and polypeptide sequences found in the Sequence Listing can also confer alteration of traits in a similar manner to the sequences found in the Sequence Listing, when transformed into a any of a considerable variety of plants of different species, and including eudicots and monocots. The polynucleotide and polypeptide sequences derived from monocots (e.g., the rice sequences) may be used to transform both monocot and eudicot plants, and those derived from eudicots (e.g., the *Arabidopsis* and soy genes) may be used to transform either group, although it is expected that some of these sequences will function best if the gene is transformed into a plant from the same group as that from which the sequence is derived.

To determine drought-related tolerance, seeds of these transgenic plants may be subjected to germination assays to measure sucrose sensing. Sterile monocot seeds, including, but not limited to, corn, rice, wheat, rye and sorghum, as well as eudicots including, but not limited to poplar, soybean and alfalfa, are sown on 80% MS medium plus vitamins with 9.4% sucrose; control media lack sucrose. All assay plates are then incubated at 22° C. under 24-hour light, 120-130.mu.Ein/m.sup.2/s, in a growth chamber. Evaluation of germination and seedling vigor is then conducted three days after planting. Plants overexpressing some of the disclosed sequences may be found to be more tolerant to high sucrose by having better germination, longer radicles, and more cotyledon expansion. These methods have been used to show that overexpressors of numerous disclosed sequences are involved in sucrose-specific sugar sensing. It is expected that structurally similar orthologs of these sequences, including those found in the Sequence Listing, are also involved in sugar sensing, an indication of altered osmotic stress tolerance.

Plants overexpressing disclosed transcription factor sequences may also be subjected to soil-based drought assays to identify those lines that are more tolerant to water deprivation than wild-type control plants. A number of the lines of plants overexpressing disclosed transcription factor polypeptides, including newly discovered closely-related species, will be significantly larger and greener, with less wilting or desiccation, than wild-type control plants, particularly after a period of water deprivation is followed by rewatering and a subsequent incubation period. The sequence of the transcription factor may be overexpressed under the regulatory control of constitutive, tissue specific or inducible promoters, or may comprise a GAL4 transactivation domain fused to either the N- or the C terminus of the polypeptide. The results presented in Examples above indicate that these transcription factors may confer abiotic stress tolerance when they are overexpressed under the regulatory control of non-constitutive promoters or a transactivation domain fused to the clade member, without having a significant adverse impact on plant morphology and/or development. The lines that display useful traits may be selected for further study or commercial development.

To verify the ability to confer abiotic stress tolerance, mature plants or seedling progeny of these plants expressing a monocot-derived equivalog gene may be challenged using methods described in the above Examples. By comparing wild type plants and the transgenic plants, the latter are shown be more tolerant to abiotic stress, and/or have greater biomass, as compared to wild type control plants similarly treated. These experiments would demonstrate that disclosed transcription factor polypeptides can be identified and shown to confer larger size, greater yield, and/or abiotic stress tolerance in eudicots or monocots, including tolerance or resistance to multiple stresses.

It is expected that the same methods may be applied to identify other useful and valuable sequences of the present transcription factor clades, and the sequences may be derived from a diverse range of species.

Further Embodiments of the Invention

Other subject matter contemplated by the present invention may is set out in the following numbered embodiments:
1. A nucleic acid construct comprising a recombinant nucleic acid sequence encoding a polypeptide, wherein:
the polypeptide shares an amino acid identity with any of SEQ ID NO: 298, 120, 175, 226, 330, 400, 436, 514, or 606, wherein the percent amino acid identity is selected from the group consisting of at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, and about 100%; or
the polypeptide comprises a conserved domain that shares an amino acid identity with a conserved domain of any of SEQ ID NO: 298, 120, 175, 226, 330, 400, 436, 514, or 606, wherein the percent amino acid identity is selected from the group consisting of at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, and about 100%; or the recombinant nucleic acid sequence specifically hybridizes to the complement of the sequence set forth in SEQ ID NO: 297, 119, 174, 225, 329, 399, 435, 513, or 605, under stringent conditions comprising two wash steps at least as stringent as 6×SSC at 65° C. of 10-30 minutes for each wash step; or the recombinant nucleic acid sequence specifically hybridizes to the complement of the sequence set forth in SEQ ID NO: 297, 119, 174, 225, 329, 399, 435, 513, or 605, under stringent conditions comprising two wash steps of 0.2× to 2×SSC and 0.1% SDS at 50° C. to 65° C. for 10-30 minutes per wash step;

wherein when the polypeptide is overexpressed in a plant, the polypeptide regulates transcription and confers at least one regulatory activity resulting in an altered trait in the plant as compared to a control plant.

2. The nucleic acid construct of embodiment 1, wherein the altered trait is altered tolerance to an abiotic stress.

3. The nucleic acid construct of embodiment 2, wherein the altered tolerance to an abiotic stress is increased tolerance to water deprivation, increased water use efficiency, increased tolerance to hyperosmotic stress, increased tolerance to low nutrient conditions, increased nutrient uptake, or increased cold tolerance.

4. The nucleic acid construct of embodiment 3, wherein the increased tolerance to water deprivation is characterized by increased time to wilting, increased tolerance to dehydration, increased tolerance to soil drought, lower soil water content at wilting, or increased time to wilting.

5. The nucleic acid construct of embodiment 3, wherein the increased water use efficiency is characterized by reduced .sup.13C discrimination.

6. The nucleic acid construct of embodiment 3, wherein the increased tolerance to hyperosmotic stress is increased tolerance to sodium chloride.

7. The nucleic acid construct of embodiment 3, wherein the increased nutrient uptake or increased tolerance to low nutrient conditions is altered C/N sensing, increased tolerance to low nitrogen condition, or increased tolerance to phosphate-free medium.

8. The nucleic acid construct of embodiment 1, wherein the altered trait is enhanced growth, altered light response, larger size, later senescence, altered development or morphology in leaf, stem, fruit, stem, seedling, trichome, root, or flower relative to a control plant.

9. The nucleic acid construct of embodiment 8, wherein the alteration in fruit development or morphology is increased fruit weight, or increased fruit set.

10. The nucleic acid construct of embodiment 8, wherein the alteration in growth is characterized by increased diameter, increased growth rate, increased height, increased dry weight, increased leaf dry weight, increased wood density, increased plant size, increased leaf area, increased specific leaf area, increased internode length, decreased "Root/Shoot" ratio, or increased biomass.

11. The nucleic acid construct of embodiment 8, wherein the altered development or morphology in leaf, stem, fruit, stem, seedling, trichome, root, or flower is increased density of trichome, altered leaf orientation, increased root mass, short root, abnormal leaf shape, darker green leaves, or larger leaves, increased biomass, increased petiole height, increased vascular bundles in stem, increased seedling vigor, increased specific leaf area, or increased flower size or number.

12. The nucleic acid construct of embodiment 1, wherein the altered trait is altered biochemistry or hormone sensitivity.

13. The nucleic acid construct of embodiment 12, wherein the altered biochemistry or hormone sensitivity is increased leaf glucosinolate M39480 level, decreased sensitivity to ABA, or higher seed lutein content.

14. The nucleic acid construct of embodiment 1, wherein the stringent conditions comprising two wash steps of 0.5×SSC, 0.1% SDS at 65° C. of 10-30 minutes for each wash step.

15. The nucleic acid construct of embodiment 1, wherein expression of the polypeptide is regulated by a constitutive, inducible, or tissue-enhanced promoter.

16. A recombinant host cell comprising a nucleic acid construct of embodiment 1.

17. A transgenic plant having an altered trait as compared to a control plant, wherein the transgenic plant comprises:

at least one nucleic acid construct comprising a recombinant nucleic acid sequence encoding a polypeptide, wherein:

the polypeptide shares an amino acid identity with any of SEQ ID NO: 298, 120, 175, 226, 330, 400, 436, 514, or 606, wherein the percent amino acid identity is selected from the group consisting of at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, and about 100%; or the polypeptide comprises a conserved domain that shares an amino acid identity with a conserved domain of any of SEQ ID NO: 298, 120, 175, 226, 330, 400, 436, 514, or 606, wherein the percent amino acid identity is selected from the group consisting of at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, and about 100%; or the recombinant nucleic acid sequence specifically hybridizes to the complement of the sequence set forth in SEQ ID NO: 297, 119, 174, 225, 329, 399, 435, 513, or 605 under stringent conditions comprising two wash steps at least as stringent as 6×SSC at 65° C. of 10-30 minutes for each wash step; or the recombinant nucleic acid sequence specifically hybridizes to the complement of the sequence set forth in SEQ ID NO: 297, 119, 174, 225, 329, 399, 435, 513, or 605, under stringent conditions comprising two wash steps of 0.2× to 2×SSC and 0.1% SDS at 50° C. to 65° C. for 10-30 minutes per wash step; and wherein when the polypeptide is overexpressed in a plant, the polypeptide regulates transcription and confers at least one regulatory activity resulting in the altered trait in the plant as compared to a control plant.

18. The transgenic plant of embodiment 17, wherein the altered trait is selected from the group consisting of: altered sugar sensing, altered tolerance to abiotic stress, altered development and morphology, early flowering, late flowering, or altered biochemistry or hormone sensitivity.

19. The transgenic plant of embodiment 18, wherein the transgenic plant is a eudicot.

20. The transgenic plant of embodiment 18, wherein the transgenic plant is a tree.

21. The transgenic plant of embodiment 20, wherein the transgenic plant is a poplar plant.

22. The transgenic plant of embodiment 18, wherein the transgenic plant is a legume.

23. The transgenic plant of embodiment 18, wherein the transgenic plant is a monocot.

24. A transgenic seed derived from the transgenic plant of embodiment 18, wherein the transgenic seed comprising the recombinant nucleic acid sequence.

25. A method for conferring to a plant an altered trait as compared to a control plant, the method comprising:

(a) providing at least one nucleic acid construct comprising a recombinant nucleic acid sequence encoding a polypeptide, wherein:

the polypeptide shares an amino acid identity with any of SEQ ID NO: 298, 120, 175, 226, 330, 400, 436, 514, or 606, wherein the percent amino acid identity is selected from the group consisting of at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, and about 100%; or the polypeptide comprises a conserved domain that shares an amino acid identity with a conserved domain of any of SEQ ID NO: 298, 120, 175, 226, 330, 400, 436, 514, or 606, wherein the percent amino acid identity is selected from the group consisting of at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, and about 100%; or the recombinant nucleic acid sequence specifically hybridizes to the complement of the sequence set forth in SEQ ID NO: 297, 119, 174, 225, 329, 399, 435, 513, or 605, under stringent conditions comprising two wash steps at least as stringent as 6×SSC at 65° C. of 10-30 minutes for each wash step; or the recombinant nucleic acid sequence specifically hybridizes to the complement of the sequence set forth in SEQ ID NO: 297, 119, 174, 225, 329, 399, 435, 513, or 605, under stringent conditions comprising two wash steps of 0.2× to 2×SSC and 0.1% SDS at 50° C. to 65° C. for 10-30 minutes per wash step;

wherein when the polypeptide is overexpressed in a plant, the polypeptide regulates transcription and confers at least one regulatory activity resulting in the altered trait in the plant as compared to a control plant; and (b) transforming a target plant with at least one nucleic acid construct to produce a transgenic plant having the altered trait as compared to the control plant.

26. The method of embodiment 25, wherein the altered trait is selected from the group consisting of: altered sugar sensing, altered tolerance to abiotic stress, altered development and morphology, altered flowering time, or altered biochemistry or hormone sensitivity relative to a control plant.

27. The method of embodiment 2, wherein the stringent conditions comprising two wash steps of 0.5×SSC, 0.1% SDS at 65° C. of 10-30 minutes for each wash step.

28. The method of embodiment 25, wherein the methods further comprises the step of:

(c) selecting a transgenic plant that ectopically expresses the polypeptide, and/or has the altered trait relative to the control plant.

29. The method of embodiment 25, wherein the method steps further comprises the step of:

(c) selfing or crossing the transgenic plant with itself or another plant, respectively, to produce a transgenic seed.

30. A method of imparting an altered trait to a poplar plant by crossing a first transgenic poplar plant with a second poplar plant, wherein said first transgenic poplar plant contains a recombinant DNA that expresses a polypeptide; wherein the altered trait is selected from the group consisting of increased tolerance to water deprivation, increased tolerance to hyperosmotic stress, increased tolerance to low nutrient conditions, increased nutrient uptake, increased water use efficiency, increased cold tolerance, altered biochemistry, hormone sensitivity, enhanced growth, altered light response, larger size, later senescence, altered development or morphology in leaf, stem, fruit, stem, seedling, trichome, root, or flower relative to a control plant;

wherein the polypeptide shares an amino acid identity with any of SEQ ID NO: 298, 120, 175, 226, 330, 400, 436, 514, or 606, wherein the percent amino acid identity is selected from the group consisting of at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, and about 100%; or the polypeptide comprises a conserved domain that shares an amino acid identity with a conserved domain of any of SEQ ID NO: 298, 120, 175, 226, 330, 400, 436, 514, or 606, wherein the percent amino acid identity is selected from the group consisting of at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, and about 100%; or the recombinant nucleic acid sequence specifically hybridizes to the complement of the sequence set forth in SEQ ID NO: 297, 119, 174, 225, 329, 399, 435, 513, or 605, under stringent conditions comprising two wash steps at least as stringent as 6×SSC at 65° C. of 10-30 minutes for each wash step; or the recombinant nucleic acid sequence specifically hybridizes to the complement of the sequence set forth in SEQ ID NO: 297, 119, 174, 225, 329, 399, 435, 513, or 605, under stringent conditions comprising two wash steps of 0.2× to 2×SSC and 0.1% SDS at 50° C. to 65° C. for 10-30 minutes per wash step;

wherein said method further comprises a screening process for identification of the altered trait.

31. The method of embodiment 30, wherein the increased tolerance to hyperosmotic stress is increased tolerance to sodium chloride.

32. The method of embodiment 30, wherein the increased nutrient uptake or increased tolerance to low nutrient conditions is altered C/N sensing, increased tolerance to low nitrogen condition or increased tolerance to phosphate-free medium 33. The method of embodiment 30, wherein the increased tolerance to water deprivation is characterized by increased time to wilting, increased tolerance to dehydration, increased tolerance to soil drought, lower soil water content at wilting, increased time to wilting.

34. The method of embodiment 30, wherein the increased water use efficiency is characterized by reduced $^{13}$C discrimination.

35. The method of embodiment 30, wherein the alteration in fruit development or morphology is increased fruit weight.

36. The method of embodiment 30, wherein the alteration in growth is characterized by increased diameter, increased growth rate, increased height, increased dry weight, increased leaf My weight, increased leaf area, increased specific leaf area, increased internode length, decreased "Root/Shoot" ratio, decreased biomass, or increased biomass.

37. The method of embodiment 30, wherein the altered development or morphology in leaf, stem, fruit, stem, seedling, trichome, root, or flower is increased density of trichome, altered leaf orientation, increased root mass, short root, abnormal leaf shape, darker green leaves, or larger leaves, increased biomass, increased vascular bundles in stem, increased seedling vigor, or increased flower size or number.

38. The method of embodiment 30, wherein the altered biochemistry or hormone sensitivity is increased leaf glucosinolate M39480 level, decreased sensitivity to ABA, or higher seed lutein content.

39. The method of embodiment 30, wherein a transgenic seed comprising the recombinant DNA is produced as a result of the crossing of the first transgenic poplar plant with the second poplar plant.

40. Wood, pulp, or bioenergy feedstock derived from the transgenic plant of embodiment 17.

41. A method of producing a transformed plant having enhanced tolerance to an environmental stress, the method comprising:

(a) introducing into one or more plant cells a recombinant polynucleotide encoding a polypeptide with an amino acid identity to SEQ ID NO: 298, 120, 175, 226, 330, 400, 436, 514, or 606;

wherein the amino acid identity is at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or about 100%;

wherein the environmental stress is selected from the group consisting of: water deficit, drought, shade, fungal disease, viral disease, bacterial disease, insect infestation, nematode infestation, cold (e.g., 4.degree.-8° C.), heat (e.g., >=32° C.), hyperosmotic stress, nitrogen-limited conditions, and phosphorus-limited conditions;

(b) exposing a plant or plants containing the one or more plant cells to the environmental stress; and (c) selecting from the plant or plants a transformed plant that expresses the polypeptide which, when expressed in the transformed plant, confers greater tolerance to the environmental stress to the transformed plant than the tolerance of a control plant which does not contain the recombinant polynucleotide.

REFERENCES CITED

Aida M, Ishida T, Fukaki H, Fujisawa H, and Tasaka M. 1997. The Plant Cell 9: 841-857

Altschul (1990) J Mol. Biol. 215: 403-410

Altschul (1993) J. Mol. Evol. 36: 290-300

Altschul et al. (1997) Nucleic Acids Res. 25: 3389-3402

Anderson and Young 1985 "Quantitative Filter Hybridisation", In: Hames and Higgins, ed., Nucleic Acid Hybridisation, A Practical Approach. Oxford, IRL Press, 73-111

Ausubel et al. (1997) Short Protocols in Molecular Biology, John Wiley & Sons, New York, N.Y., unit 7.7

Bairoch et al. (1997) Nucleic Acids Res. 25: 217-221

Berger and Kimmel (1987) "Guide to Molecular Cloning Techniques", in Methods in Enzymology, vol. 152, Academic Press, Inc., San Diego, Calif.

Bevan (1984) Nucleic Acids Res. 12: 8711-8721

Bhattacharjee et al. (2001) Proc. Natl. Acad. Sci. USA 98: 13790-13795
Borevitz et al. (2000) Plant Cell 12: 2383-2393Boss and Thomas (2002) Nature 416: 847-850
Breen and Crouch (1992) Plant Mol. Biol. 19:1049-1055
Bruce et al. (2000) Plant Cell 12: 65-79
Byrne (2000) Nature 408: 967-971
Cassas et al. (1993) Proc. Natl. Acad. Sci. USA 90: 11212-11216
Christou et al. (1987) Proc. Natl. Acad. Sci. USA 84: 3962-3966
Christou (1991) Bio/Technol. 9:957-962
Christou et al. (1992) Plant. J. 2: 275-281
Corona et al. (1996) Plant J. 9: 505-512
Coruzzi et al. (2001) Plant Physiol. 125: 61-64
Coupland (1995) Nature 377: 482-483
Dayhoff et al. (1978) "A model of evolutionary change in proteins," in "Atlas of Protein Sequence and Structure," Vol. 5, Suppl. 3 (ed. M. O. Dayhoff), pp. 345-352. Natl. Biomed. Res. Found., Washington, D.C.
Dehesh K, Bruce W B, Quail P H (1990) Science December 7; 250 (4986):1397-1399
Deshayes et al. (1985) EMBO J.: 4: 2731-2737
D'Halluin et al. (1992) Plant Cell 4: 1495-1505
Donn et al. (1990) in Abstracts of VIIth International Congress on Plant Cell and Tissue Culture IAPTC, A2-38: 53
Doolittle, ed. (1996) Methods in Enzymology, vol. 266: "Computer Methods for Macromolecular Sequence Analysis" Academic Press, Inc., San Diego, Calif., USA
Draper et al. (1982) Plant Cell Physiol. 23: 451-458
Duboule, D. (1994). Guidebook to the Homeobox Genes. Oxford, Oxford University Press.
Eddy (1996) Curr. Opin. Str. Biol. 6: 361-365
Eisen (1998) Genome Res. 8: 163-167
Farquhar and Richards (1984) Aust J of plant phys. 11: 539-552
Farquhar et al. (1989). Ann Rev Plant Physiol Plant Mol Biol 40:503-537
Feng and Doolittle (1987) J. Mol. Evol. 25: 351-360
Foster et al. (1994) FASEB J. 8: 192-200
Fromm et al. (1990) Bio/Technol. 8: 833-839
Fu et al. (2001) Plant Cell 13: 1791-1802
Gelvin et al. (1990) Plant Molecular Biology Manual, Kluwer Academic Publishers
Gilmour et al. (1998) Plant J. 16: 433-442
Glick and Thompson, eds. (1993) Methods in Plant Molecular Biology and Biotechnology, CRC Press, Inc., Boca Raton
Goodrich et al. (1993) Cell 75: 519-530
Gordon-Kamm et al. (1990) Plant Cell 2: 603-618
Gruber et al. ((1993) in Methods in Plant Molecular Biology and Biotechnology, p. 89-119
Hain et al. (1985) Mol. Gen. Genet. 199: 161-168
Hein (1990) Methods Enzymol. 183: 626-645
Hempel (1997) Development 124: 3845-3853
Henikoff and Henikoff (1992) Proc. Natl. Acad. Sci. USA 89:10915)
Herrera-Estrella et al. (1983) Nature 303: 209
Hiei et al. (1994) Plant J. 6:271-282
Hiei et al. (1997) Plant Mol. Biol. 35:205-218
Higgins et al. (1996) Methods Enzymol. 266: 383-402
Hwang and Goodman (1995) Plant J. 8: 37-43
Kim et al. (2001) Plant J. 25: 247-259
Kyozuka and Shimamoto (2002) Plant Cell Physiol. 43: 130-135
Haymes et al. "Nucleic Acid Hybridization: A Practical Approach", IRL Press, Washington, D.C. (1985)
He et al. (2000) Transgenic Res. 9: 223-227
Henikoff and Henikoff (1991) Nucleic Acids Res. 19: 6565-6572
Henikoff and Henikoff (1992) Proc. Natl. Acad. Sci. USA 89:10915
Hwang, I., and J. Sheen (2001) Nature 413: 383-389
Ishida (1990) Nature Biotechnol. 14:745-750
Ishiguro, S., and Nakamura, K. (1994). Mol Gen Genet. 244, 563-571
Jaglo et al. (2001) Plant Physiol. 127: 910-917
Jensen, R. B., Jensen, K. L., Jesperson, H. M., Skriver, K. (1998) FEBS letters 436:283-287
Karimi, M. et al. (2002), Trends In plant Sciences, 7 (5): 193-195
Kashima et al. (1985) Nature 313: 402-404
Kasuga et al. (1999) Nature Biotechnol. 17: 287-291
Kimmel (1987) Methods Enzymol. 152: 507-511
Klug, A. and Schwabe, J. W. R. (1995). Zinc fingers. FASEB Journal 9, 597-604.
Klug, A. and Schwabe, J. W. R. (1995). Zinc fingers. FASEB Journal 9, 597-604.
Klee (1985) Bio/Technology 3: 637-642
Klein et al. (1987) Nature 327: 70-73
Klug and Schwabe (1995) FASEB J. 9: 597-604 Kosugi S, Ohashi Y. J Biol. Chem. 2002 May 10; 277(19):16553-8.
Lam et al. Plant Physiology 2003, vol. 132: 926-935.
Lee et al. (2002) Genome Res. 12: 493-502
Lin et al. (1991) Nature 353: 569-571
Lippuner, V., Cyert, M. S., and Gasser, C. S. (1996). Two classes of plant cDNA clones differentially complement yeast calcineurin mutants and increase salt tolerance of wild-type yeast. Journal of Biological Chemistry 271, 12859-12866.
Littlewood, T. D. and Evan, G. I. (1994) Prot. Profile, 1: 639-709
Littlewood and Evan (1998) Helix-Loop-Helix Transcription Factors (New York: Oxford University Press)
Long et al. (1996) Nature 379: 66-69
Long and Barton (2000) Dev. Biol. 218: 341-353 Magyar, Z., Atanassova, A., De Veylder, L., Rombauts, S, and Inze, D. (2000). FEBS Lett. 486:79-87
Mandel (1992) Nature 360: 273-277
Mandel et al. (1992) Cell 71-133-143
Mariconti L, Pellegrini B, Cantoni R, Stevens R, Bergounioux C, Cella R, Albani D. J Biol Chem 2002 Mar. 22; 277(12):9911-9.
Martin and Paz-Ares (1997) Trends Genet. 13: 67-73 Martinez-Garcia, M., Garciduenas-Pina, C., and Guzman, P. (1996). Molecular & General Genetics 252, 587-596
McNellis, T. W., Torii, K. U., and Deng, X. W. (1996). Plant Cell 8, 1491-1503
Meyers (1995) Molecular Biology and Biotechnology, Wiley VCH, New York, N.Y., p 856-853
Miki et al. (1993) in Methods in Plant Molecular Biology and Biotechnology, p. 67-88,
Montgomery et al. (1993) Plant Cell 5: 1049-1062
Mount (2001), in Bioinformatics: Sequence and Genome Analysis, Cold Spring Harbor Laboratory Press, Cold Spring Harbor, N.Y., page 543
Muller et al. (2001) Plant J. 28: 169-179
Nandi et al. (2000) Curr. Biol. 10: 215-218
Nicholass et al. (1995) Plant Mol. Biol. 28: 423-435
Nilsson, O. et al. (1992) Transgenic Research 1: 209-220
Odell et al. (1985) Nature 313: 810-812
Oliver D J, Raman R (1995) Bioenerg Biomembr 27(4): 407-14

Omichinski, J. G., Trainor, C., Evans, T., Gronenborn, A. M., Clore, G. M., and
Felsenfeld, G. (1993). Proceedings of the National Academy of Sciences of the United States of America 90, 1676-1680.
Pavletich, N. P., and Pabo, C. O. (1993). Science (Washington D.C.) 261, 1701-1707.
Peng et al. (1997) Genes Development 11: 3194-3205)
Peng et al. (1999) Nature: 400: 256-261
Ratcliffe et al. (2001) Plant Physiol. 126: 122-132
Reeves and Beckerbauer (2001) Biochim Biophys Acta 1519: 13-29.
Reeves (2001) Gene 277: 63-81.
Remm et al. (2001) J. Mol. Biol. 314: 1041-1052
Riechmann, J. L., J. Heard, G. Martin, L. Reuber, C.-Z. Jiang, J. Keddie, L. Adam, O. Pineda, O. J. Ratcliffe, R. R. Samaha, R. Creelman, M. Pilgrim, P. Broun, J. Z. Zhang, D. Ghandehari, B. K. Sherman, and G.-L. Yu (2000a) Science 290: 2105-2110.
Riechmann and Ratcliffe (2000b) Curr. Opin. Plant Biol. 3: 423-434
Rieger et al. (1976) Glossary of Genetics and Cytogenetics: Classical and Molecular, 4th ed., Springer Verlag, Berlin
Robson et al. (2001) Plant 28: 619-631
Rolland, F., B. Moore, and J. Sheen (2002) Plant Cell Supplement 2002: S185-S205.
Sadowski et al. (1988) Nature 335: 563-564
Sanford et al. (1987) Part. Sci. Technol. 5:27-37
Sanford (1993) Methods Enzymol. 217: 483-509
Sakai, H., T. Aoyama, and A. Oka. (2000) Plant J. 24: 703-711.
Sakai, H., T. Honma, T. Aoyama, S. Sato, T. Kato, S. Tabata, and A. Oka. (2001) Science 294: 1519-1521
Sambrook et al. (1989) Molecular Cloning: A Laboratory Manual, 2nd Ed., Cold Spring Harbor Laboratory, Cold Spring Harbor, N.Y.
Schauser, L., Christensen, L., Borg, S., and Poulsen, C. (1995). Plant Physiology (Rockville) 107, 1457-1458.
Sablowski R and Meyerowitz E M. 1998. Cell 92: 93-103.
Shpaer (1997) Methods Mol. Biol. 70: 173-187
Sjodahl et al. (1995) Planta 197: 264-271
Smalle et al (1998) Proc. Natl. Acad. Sci. USA. 95:3318-3322
Smith et al. (1992) Protein Engineering 5: 35-51
Sonnhammer et al. (1997) Proteins 28: 405-420
Spencer et al. (1994) Plant Mol. Biol. 24: 51-61
Speulman, E., and Salamini, F. (1995). Plant Science (Limerick) 106, 91-98.
Stitt (1999) Curr. Opin. Plant. Biol. 2: 178-186
Suzuki et al. (2001) Plant J. 28: 409-418
Tague, B. W., and Goodman, H. M. (1995). Plant Molecular Biology 28, 267-279.
Takada S, Hibara Ki, Ishida T, and Tasaka M. 2001. Development 128, 1127-1135.
Takatsuji, H. (1998) Cell, Mol., Life Sci. 54:582-596.
Takatsuji, H. (1998). Sciences 54, 582-596.
Taylor and Scheuring (1994) Mol. Gen. Genet. 243: 148-157
Thoma (1994) Plant Physiol. 105: 35-45
Thompson et al. (1994) Nucleic Acids Res. 22: 4673-4680
Vazquez et al. (1999) Development 126: 733-742
Vasil et al. (1992) Bio/Technol. 10:667-674
Vasil et al. (1993) Bio/Technol. 11:1553-1558
Vasil (1994) Plant Mol. Biol. 25: 925-937
Wahl and Berger (1987) Methods Enzymol. 152: 399-407
Wan and Lemeaux (1994) Plant Physiol. 104: 37-48
Wanner and Gruissem (1991) Plant Cell 3: 1289-1303
Weeks et al. (1993) Plant Physiol. 102:1077-1084
Weigel and Nilsson (1995) Nature 377: 482-500
Weissbach and Weissbach (1989) Methods for Plant Molecular Biology, Academic Press
Wu (ed.) Meth. Enzymol. (1993) vol. 217, Academic Press
Xu et al. (2001) Proc. Natl. Acad. Sci. USA 98: 15089-15094
Zhang et al. (1991) Bio/Technology 9: 996-997

All publications and patent applications mentioned in this specification are herein incorporated by reference to the same extent as if each individual publication or patent application was specifically and individually indicated to be incorporated by reference.

The present claims are not limited by the specific embodiments described herein. The instant sequences, plants, and methods now being fully described, it will be apparent to one of ordinary skill in the art that many changes and modifications can be made thereto without departing from the spirit or scope of the appended claims. Modifications that become apparent from the foregoing description and accompanying figures fall within the scope of the claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09676831B2). An electronic copy of the "Sequence Listing" will also be available from the USPTO upon request and payment of the fee set forth in 37 CFR 1.19(b)(3).

What is claimed is:

1. A transgenic poplar plant having an altered trait as compared to a control plant, wherein the transgenic plant comprises: a nucleic acid construct comprising a recombinant nucleic acid encoding a polypeptide according to SEQ ID NO: 514;
wherein expression of the polypeptide is regulated by a 35S promoter; and
wherein expression of the polypeptide confers the transgenic plant with at least one altered trait selected from the group consisting of increased growth rate, increased plant height and increased wood density.

2. A plant part or plant material derived from the transgenic plant of claim 1, wherein the plant part or plant material comprises the recombinant nucleic acid sequence.

3. Wood, pulp, or feedstock derived from the transgenic plant of claim 1, wherein the wood, pulp, or feedstock comprises the recombinant nucleic acid sequence.

4. A transgenic seed derived from the transgenic plant of claim 1, wherein the transgenic seed comprises the recombinant nucleic acid sequence.

5. A method for conferring to a poplar plant at least one altered trait selected from the group consisting of increased growth rate, increased plant height and increased wood density as compared to a control plant, the method comprising:
(a) providing a nucleic acid construct comprising a recombinant nucleic acid encoding a polypeptide according to SEQ ID NO: 514;
wherein expression of the polypeptide is regulated by a 35S promoter; and
(b) introducing said nucleic acid construct into a target plant to produce a transgenic plant wherein expression of said nucleic acid construct confers the poplar plant with at least one altered trait selected from the group consisting of increased growth rate, increased plant height and increased wood density as compared to the control plant lacking said nucleic acid construct.

6. A method of imparting at least one altered trait selected from the group consisting of increased growth rate, increased plant height and increased wood density to a poplar plant relative to a control plant by
a) crossing a first transgenic poplar plant with a second poplar plant; and
b) growing a progeny plant from the seed derived from the cross of step (a); wherein said first transgenic plant is the plant from claim 1; and wherein said progeny plant comprises the nucleic acid construct of the first plant and exhibits at least one altered trait selected from the group consisting of increased growth rate, increased plant height and increased wood density compared to the second plant.

7. A cell from the plant of claim 1.

\* \* \* \* \*